US009844582B2

(12) United States Patent
Wittrup et al.

(10) Patent No.: US 9,844,582 B2
(45) Date of Patent: Dec. 19, 2017

(54) SYNERGISTIC TUMOR TREATMENT WITH EXTENDED-PK IL-2 AND THERAPEUTIC AGENTS

(71) Applicant: Massachusetts Institute of Technology, Cambridge, MA (US)

(72) Inventors: Karl Dane Wittrup, Chestnut Hill, MA (US); Byron Hua Kwan, Boston, MA (US); Shuning Gai, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/402,889

(22) PCT Filed: May 21, 2013

(86) PCT No.: PCT/US2013/042057
§ 371 (c)(1),
(2) Date: Nov. 21, 2014

(87) PCT Pub. No.: WO2013/177187
PCT Pub. Date: Nov. 28, 2013

(65) Prior Publication Data

US 2015/0132254 A1 May 14, 2015

Related U.S. Application Data

(60) Provisional application No. 61/650,277, filed on May 22, 2012.

(51) Int. Cl.

*A61K 38/20* (2006.01)
*A61K 38/38* (2006.01)
*A61K 39/395* (2006.01)
*A61K 47/48* (2006.01)
*A61K 45/06* (2006.01)

(52) U.S. Cl.
CPC ........ *A61K 38/2013* (2013.01); *A61K 38/385* (2013.01); *A61K 39/39533* (2013.01); *A61K 45/06* (2013.01); *A61K 47/48215* (2013.01)

(58) Field of Classification Search
None
See application file for complete search history.

(56) References Cited

U.S. PATENT DOCUMENTS 4,745,180 A 5/1988 Moreland et al.
4,863,727 A * 9/1989 Zimmerman ...... A61K 38/2013 424/85.2
4,902,502 A 2/1990 Nitecki et al.
4,999,339 A 3/1991 Paradise et al.
5,126,132 A 6/1992 Rosenberg
5,206,344 A 4/1993 Katre et al.
5,349,053 A * 9/1994 Landolfi ................ C07K 14/55 424/134.1
5,645,835 A * 7/1997 Fell, Jr. ............ A61K 47/48569 424/134.1
7,402,431 B2 7/2008 Har-Noy
7,462,350 B2 * 12/2008 Gillies ................... C07K 14/55 424/85.2
8,828,381 B2 * 9/2014 Warnaar ............. A61K 38/2013 424/130.1
2002/0009427 A1 * 1/2002 Wolin ............. A61K 39/39541 424/85.2
2002/0041865 A1 * 4/2002 Austin ............ A61K 47/48238 424/85.2
2014/0242049 A1 8/2014 Choi et al.
2015/0017120 A1 1/2015 Wittrup et al.

FOREIGN PATENT DOCUMENTS

WO 87/00056 A1 1/1987
WO 8700056 A1 1/1987
WO 90/04412 A1 5/1990
WO 96/40176 A1 12/1996
WO 96/40249 A1 12/1996
WO 02/087304 A2 11/2002
WO 03/048334 A2 6/2003
WO 2005/007121 A2 1/2005
WO 2008/003473 A2 1/2008
WO 2008/045252 A2 4/2008
WO 2009/061853 A2 5/2009
WO 2009/117117 A1 9/2009
WO 2010/025177 A1 3/2010
WO WO2011001276 * 1/2011 ........... A61K 39/395
WO 2012/064658 A1 5/2012
WO 2013/151771 A1 10/2013
WO 2013/177187 A2 11/2013
WO 2014201378 A1 12/2014
WO 2016/025642 A1 2/2016
WO 2016/025645 A1 2/2016
WO 2016/025647 A1 2/2016

OTHER PUBLICATIONS

Clark et al. Interleukin-2 in cancer therapy. In Cancer Drug Discovery and Development: Immunotherapy of cancer. Chapter 20, M.L. Disis ed., Humana press Inc. Totowa, NJ, 2006.*
Asano et al., Immunostimulatory therapy with anti-cd3 monoclonal antibodies and recombinant interleukin-2: heightened in vivo expression of mRNA encoding cytotoxic attack molecules and immunoregulatory cytokines and regression of murine renal cell carcinoma. J. Urology, 157, 2396-2401, 1997.*
De Mulder, P. et al., "PEG-IL-2 and Cyclophosphamide in Advanced Cancer in the Guinea Pig," Proceedings of the American Association for Cancer Research Annual Meeting, 1994, vol. 35, No. 0, p. 521, XP1526374, & Proceedings of the 85th Annual Meeting of the American Association for Cancer Research, San Francisco, CA, USA, Apr. 10-13, 1994, ISSN: 0197-016X, abstract 3105.

(Continued)

*Primary Examiner* — Elly-Gerald Stoica
(74) *Attorney, Agent, or Firm* — Nelson Mullins Riley & Scarborough LLP; Amy E. Mandragouras, Esq.; Ariana D. Harris

(57) ABSTRACT

The present invention relates to methods of treating cancer with a combination of extended-PK IL-2 and one or more therapeutic agents, such as a therapeutic antibody. The methods of the invention are applicable across any type of cancer.

41 Claims, 18 Drawing Sheets

(56) References Cited

OTHER PUBLICATIONS

International Preliminary Report on Patentability, PCT/US2013/042057, dated Nov. 25, 2014, pp. 1-9.
International Search Report and Written Opinion, PCT/US2013/042057, dated Nov. 22, 2013, pp. 1-15.
Kim, B. et al., "Polyethylene Glycol Modified Interleukin-2 and Anti-CD3 Monoclonal Antibody Treatment of Pulmonary Metastases," Proceedings of the American Association for Cancer Research Annual Meeting & Proceedings of the 82nd Annual Meeting of the American Association for Cancer Research, Houston, TX, 1991, vol. 32, p. 249, XP1526373, ISSN: 0197-016X, abstract 1479.
Cho, H.I. et al., "A Potent Vaccination Strategy That Circumvents Lymphodepletion for Effective Antitumor Adoptive T-cell Therapy," Cancer Research, vol. 72(8): 1986-1995 (2012).
Ellis, L. et al., "VEGF-targeted therapy: mechanisms of anti-tumour Activity," Nature Reviews Cancer, vol. 8(8-3): 579-591 (2008).
International Preliminary Report on Patentability, PCT/US2014/042341, dated Dec. 15, 2015, 10 pages.
International Search Report and Written Opinion, PCT/US2014/042341, dated Nov. 10, 2014,15 pages.
International Search Report and Written Opinion, PCT/US2015/044920, dated Dec. 7, 2015, 12 pages.
International Search Report and Written Opinion, PCT/US2015/044924, dated Dec. 2, 2015, 14 pages.
International Search Report and Written Opinion, PCT/US2015/044927, dated Dec. 2, 2015, 13 pages.
Kowolik, C. M., et al., "CD28 Costimulation Provided through a CDI9-Specific Chimeric Antigen Receptor Enhances In vivo Persistence and Antitumor Efficacy of Adoptively Transferred T Cells," Cancer Research, vol. 66, No. 22, Nov. 15, 2006, pp. 10995-11004, XP055044266, ISSN: 0008-5472, 001: 1158/8888-5472. CAN-06-0160.
Ly, L. V. et al., "Effective Cooperation of Monoclonal Antibody and Peptide Vaccine for the Treatment of Mouse Melanoma," The Journal of Immunology, vol. 190(1):498-496 (2012).
Moore, S. J. et al., "Engineered knottin peptide enables noninvasive optical imaging of intracranial medulloblastoma," PNAS, vol. 110(36): 14598-14603 (2013).
Pardoll, D.M. et al., "The blockade of immune checkpoints in cancer immunotherapy," Nature Reviews Cancer, vol. 12(4): 252-264 (2012).
Zheng, Yiran, et ai, "In Vivo Targeting of Adoptively Transferred T -cells with Antibody- and Cytokine-conjugated Liposomes," Journal of Controlled Release, vol. 172, No. 2, Jun. 11, 2013, pp. 426-435, XP028759063, ISSN: 0168-3659, 001:10.1016/J.JCONREL.2013.05.037.
U.S. Appl. No. 14/304,438, filed Jun. 13, 2014, Karl Dane Wittrup.
U.S. Appl. No. 14/304,438, dated Mar. 15, 2016.
U.S. Appl. No. 14/304,438, dated Oct. 18, 2016.
Yang, JC et al., "Murine studies using polyethylene glycol-modified recombinant human interleukin 2 (PEG-IL-2): antitumor effects of PEG-IL2 alone and in combination with adoptive cellular transfer," Lymphokine Cytokine Res., vol. 10(6): 475-480(1991) (Abstract only).
Berenbaum, MC, "Synergy, additivism and antagonism in immunosuppression. A critical review," Clin exp Immunol, vol. 28(1):1-18 (1977).
Wiesenthal, "Synergy analysis of "classic" and newer drug combinations," Human Tumor Assay Journal, on-line at http://weisenthal.org/synergy1.htm, Mar. 14, 2012, 1 page.
U.S. Appl. No. 14/304,438, dated May 25, 2017.

* cited by examiner

FIGURE 1

SYNERGISTIC TUMOR TREATMENT WITH EXTENDED-PK IL-2 AND THERAPEUTIC AGENTS

CROSS-REFERENCE TO RELATED APPLICATIONS

This application is a 35 U.S.C. 371 national stage filing of International Application PCT/US2013/042057, filed May 21, 2013, which claims priority to U.S. Provisional patent application 61/650,277, filed May 22, 2012. The contents of the aforementioned applications are hereby incorporated by reference herein in their entirety.

GOVERNMENT FUNDING

This invention was made with government support under Grant No. W81XWH-10-1-0291 awarded by the Army Medical Research Command and under Grant No. R01 AI065824 awarded by the National Institutes of Health. The government has certain rights in this invention.

BACKGROUND

Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD122 in humans) and p64 (IL-2Rγ, the gamma subunit, also known as CD132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Rα is recycled to the cell surface, while IL-2 associated with the IL-2:IL-2Rβγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with IL-2 treatment is largely attributable to the activity of natural killer (NK) cells. NK cells express the intermediate-affinity receptor, IL-2R$\beta\gamma_c$, and thus are stimulated at nanomolar concentrations of IL-2, which do in fact result in patient sera during high-dose IL-2 therapy. Attempts to reduce serum concentration, and hence selectively stimulate IL-2R$\alpha\beta\gamma_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

SUMMARY

While some attempts have been made to combine IL-2 with therapeutic antibodies to effectively treat various cancers, these efforts have been largely unsuccessful. The present invention is based, in part, on the discovery that prolonging the circulation half-life of IL-2 by attaching a pharmacokinetic modifying group (hereafter referred to as "extended-pharmacokinetic (PK) IL-2") substantially increases the ability of IL-2 to control tumors in various cancer models. By prolonging circulation half-life, in vivo serum IL-2 concentrations can be maintained within a therapeutic range, which is not possible with free IL-2. As discussed infra, the methods of the present invention allow for synergistic tumor control by combining extended-PK IL-2, with one or more therapeutic agents, such as a therapeutic antibody.

In one aspect, the invention relates to a method for increasing IL-2R beta and IL-2R gamma signaling in a lymphocyte in vivo by administering an agent which stimulates IL2R$\beta\gamma_c$, such as an extended-PK interleukin (IL)-2 or a IL-15 superagonist/IL-15Rα complex or an IL-2/IL-2 antibody complex, and a therapeutic agent to the cell in an amount effective to increase IL-2R beta and IL-2R gamma signaling.

In another aspect, the invention relates to a method for treating cancer in a subject by administering an extended-PK IL-2, and a therapeutic agent in an amount effective to treat cancer. The cancer to be treated can be, e.g., melanoma, colon cancer, breast cancer, renal cancer, testicular cancer, ovarian cancer, prostate cancer, cancer of the small intestine, cancer of the esophagus, cervical cancer, lung cancer, lymphoma, and leukemia.

In another aspect, the invention relates to a method for treating cancer and reducing vascular leak syndrome associated with IL-2 therapy in a subject by administering an extended-PK IL-2, and a therapeutic antibody in an amount effective to treat cancer and reduce vascular leak syndrome associated with IL-2 therapy in the subject. In another aspect, the invention relates to a method for treating cancer and reducing pulmonary edema associated with IL-2 therapy in a subject by administering an extended-PK IL-2, and a therapeutic antibody in an amount effective to treat cancer and reduce pulmonary edema associated with IL-2 therapy in the subject.

In another aspect, the invention relates to a method of inhibiting the growth and/or proliferation of tumor cells in a subject by administering an extended-PK IL-2 and a therapeutic antibody in an amount effective to inhibit growth and/or proliferation of tumor cells in the subject. In one aspect, the methods of the invention result in a reduction in tumor size in the subject, for example, by at least 30%, at least 50%, at least 80%, or at least 90%. In one embodiment, the extended-PK IL-2 and therapeutic agent reduces tumor size to a greater extent than achieved by a combination of IL-2 and a therapeutic antibody. In another aspect, the treatment according to the invention increases the recruitment of lymphocytes to the periphery of a tumor. In one embodiment, such methods inhibit primary tumor metastasis. In yet another aspect, methods of the invention prolong the survival of a subject with a tumor, such as a mouse model of cancer, by, e.g., 25 days or more.

In another aspect, the invention relates to a method of stimulating T cells and/or NK cells in a subject by administering an extended-PK interleukin (IL)-2, and a therapeutic agent in an amount effective to stimulate T cells and/or NK cells in a subject. In one embodiment, the stimulation of T cells and/or NK cells leads to enhanced antibody-dependent cell-mediated cytotoxicity (ADCC) and/or cytotoxic T lymphocyte (CTL) responses. In another embodiment, the stimulation of T cells and/or NK cells leads to an increased number of CD8+ T cells in a subject.

The extended-PK IL-2 of the methods described above can be in the form of a fusion protein, such as an IL-2 moiety fused to an immunoglobulin fragment such as Fc, human serum albumin, or Fn3. Alternatively, the extended-PK IL-2 is conjugated to a non-protein polymer, such as PEG. When the IL-2 moiety is fused to an Fc domain, the Fc domain may be mutated to reduce binding to Fcγ receptors, complement proteins, or both, i.e., to reduce effector function. In other embodiments, the fusion protein comprises a monomer of one IL-2 moiety linked to an Fc domain as a heterodimer, or a dimer of two IL-2 moieties linked to an Fc domain as a heterodimer. In other embodiments, IL-2 is mutated such that it has higher affinity for the IL-2R alpha receptor compared to unmodified IL-2.

The therapeutic agents to be used in combination with the extended-PK IL-2 of the methods described above can be, e.g., a therapeutic antibody, a therapeutic protein, a small molecule, an antigen, or a population of cells. The extended-PK IL-2 and the therapeutic agent are administered simultaneously or sequentially. In one embodiment, the extended-PK IL-2 and the therapeutic agent are administered within three days of each other. In another embodiment, one or more additional therapeutic agents are added to the combination of extended-PK IL-2 and therapeutic agent. Such agents can be, e.g., a cytokine, a chemotherapeutic agent, and/or a population of cytotoxic T cells.

BRIEF DESCRIPTION OF THE DRAWINGS

These and other features, aspects, and advantages of the present invention will become better understood with regard to the following description, and accompanying drawings, where:

FIG. 1 depicts the sequences of high affinity CD25-binding mouse IL-2 mutants generated by error prone PCR and yeast surface display. mIL-2 depicts the sequence of murine IL-2. The locations of mutations in the IL-2 mutants are shown. The mutants with names preceded by "QQ" are those in which putative IL-2Rβ-binding mutations were reverted back to wild-type residues by site directed mutagenesis.

DETAILED DESCRIPTION

Figure 2:
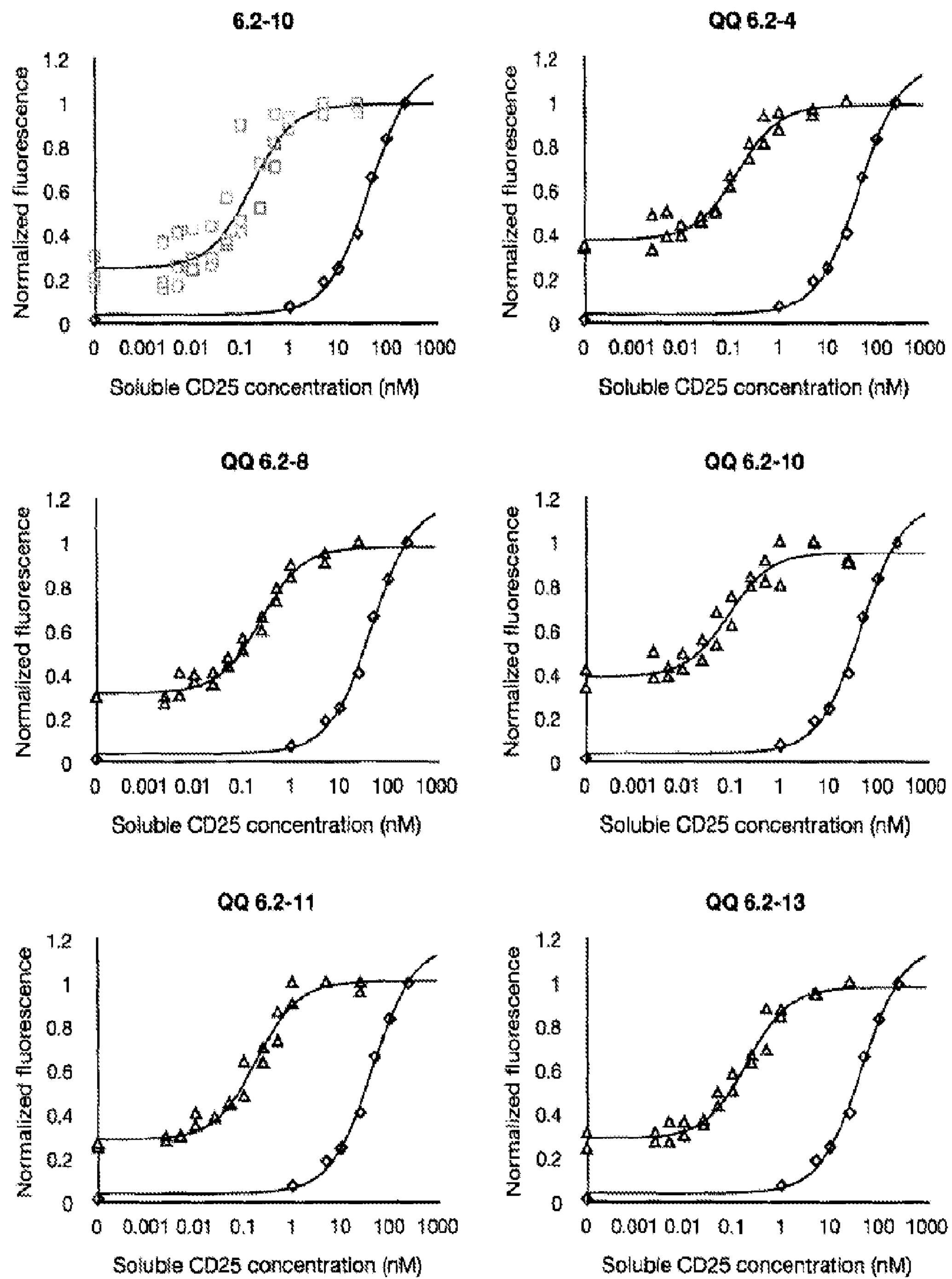
FIG. 2 is a series of graphs depicting the affinity of the indicated IL-2 mutants for soluble murine CD25. The equilibrium dissociation constant was determined as described in Chao et al. (*Nat Protocols* 2006; 1(2):755-768). Diamonds indicate wild-type murine IL-2; squares indicate IL-2 6.2-10; triangles indicate IL-2 mutants in which putative IL-2Rβ-binding mutations were reverted back to wild-type residues.

In one aspect, the present invention relates to a method of treating cancer comprising administering an extended-PK IL-2 and one or more therapeutic agents, such as a therapeutic antibody, with or without one or more additional agents, to a subject in need thereof in an amount sufficient to treat cancer, e.g., to reduce the tumor size and growth in the subject. In another aspect, the methods of the present invention prolong survival of subjects with cancer. In other aspects, extended-PK IL-2 and one or more therapeutic agents synergizes to exert potent tumor growth suppression.

Definitions

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

“Nucleic acid” refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene. Polynucleotides of the present invention can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. “Modified” bases include, for example, tritylated bases and unusual bases such as inosine. A variety of modifications can be made to DNA and RNA; thus, “polynucleotide” embraces chemically, enzymatically, or metabolically modified forms.

As used herein, the term “PK” is an acronym for “pharmacokinetic” and encompasses properties of a compound including, by way of example, absorption, distribution, metabolism, and elimination by a subject. As used herein, an “extended-PK group” refers to a protein, peptide, or moiety that increases the circulation half-life of a biologically active molecule when fused to or administered together with the biologically active molecule. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US2012/094909), human serum albumin, Fc or Fc fragments and variants thereof, and sugars (e.g., sialic acid). Other exemplary extended-PK groups are disclosed in Kontermann et al., *Current Opinion in Biotechnology* 2011; 22:868-876, which is herein incorporated by reference in its entirety. As used herein, an “extended-PK IL-2” refers to an IL-2 moiety in combination with an extended-PK group. In one embodiment, the extended-PK IL-2 is a fusion protein in which an IL-2 moiety is linked or fused to an extended-PK group. An exemplary fusion protein is a Fc/IL-2 fusion in which one or more IL-2 moieties are linked to an immunoglobulin Fc domain (e.g., an IgG1 Fc domain).

Figure 1:
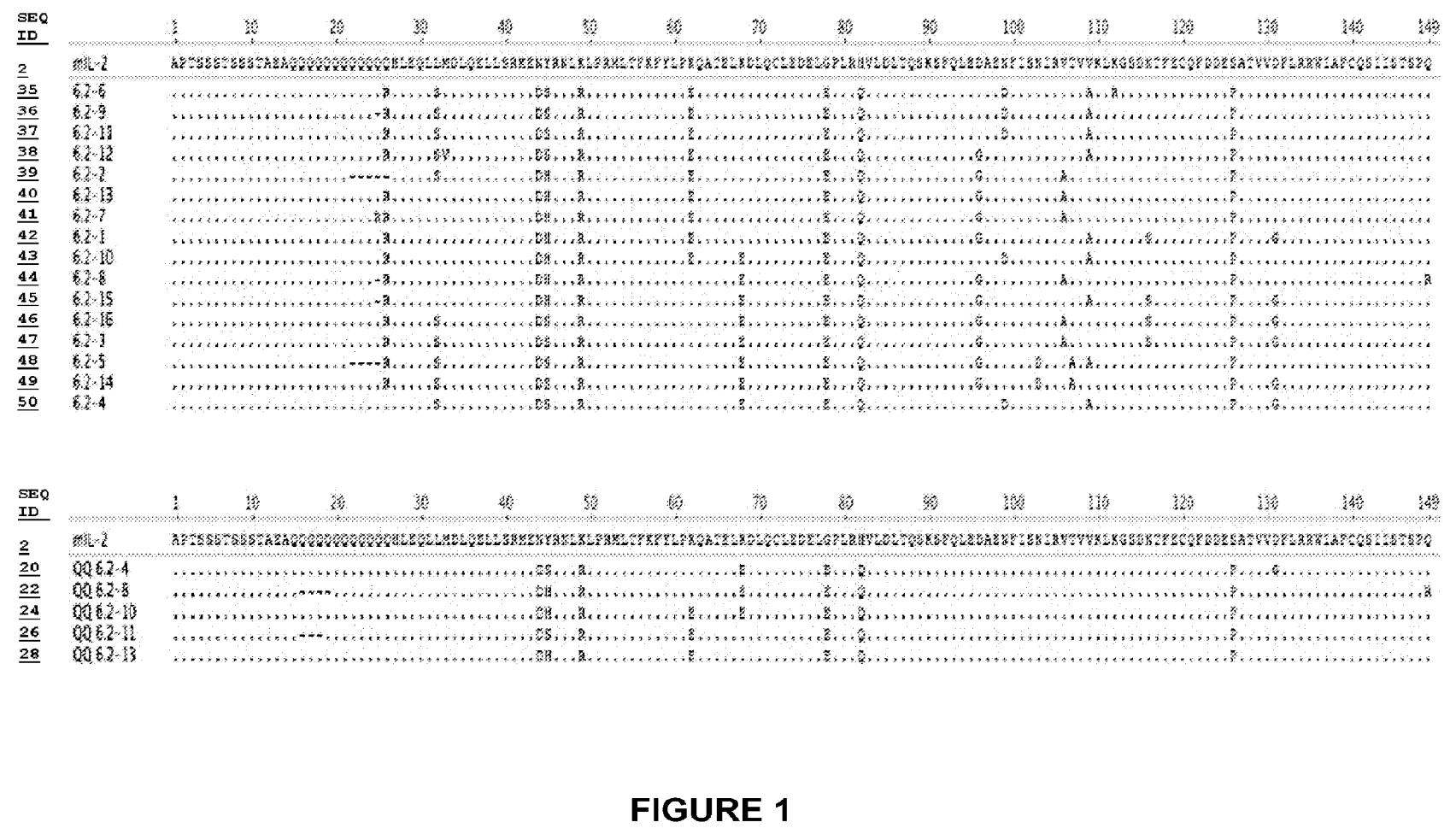

The term “extended-PK IL-2” is also intended to encompass IL-2 mutants with mutations in one or more amino acid residues that enhances the affinity of IL-2 for one or more of its receptors, for example, CD25. In one embodiment, the IL-2 moiety of extended-PK IL-2 is wild-type IL-2. In another embodiment, the IL-2 moiety is a mutant IL-2 which exhibits greater affinity for CD25 than wild-type IL2, such as one of the IL-2 mutants depicted in FIG. 1. When a particular type of extended-PK group is indicated, such as PEG-IL-2, it should be understood that this encompasses both PEG conjugated to a wild-type IL-2 moiety or a PEG conjugated to a mutant IL-2 moiety.

In certain aspects, the extended-PK IL-2 of the invention can employ one or more “linker domains,” such as polypeptide linkers. As used herein, the term “linker domain” refers to a sequence which connects two or more domains (e.g., the PK moiety and IL-2) in a linear sequence. As used herein, the term “polypeptide linker” refers to a peptide or polypeptide sequence (e.g., a synthetic peptide or polypeptide sequence) which connects two or more domains in a linear amino acid sequence of a polypeptide chain. For example, polypeptide linkers may be used to connect an IL-2 moiety to an Fc domain. Preferably, such polypeptide linkers can provide flexibility to the polypeptide molecule. In certain embodiments the polypeptide linker is used to connect (e.g., genetically fuse) one or more Fc domains and/or IL-2.

As used herein, the terms “linked,” “fused”, or “fusion”, are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, the term “Fc region” shall be defined as the portion of a native immunoglobulin formed by the respective Fc domains (or Fc moieties) of its two heavy chains. As used herein, the term “Fc domain” refers to a portion of a single immunoglobulin (Ig) heavy chain wherein the Fc domain does not comprise an Fv domain. As such, Fc domain can also be referred to as “Ig” or “IgG.” In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and in Table 5 (i.e., SEQ ID NO: 33). The Fc domain of human IgG1 can be found in Table 5 (i.e., SEQ ID NO: 34). The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., *Sequences of Proteins of Immunological Interest* (Table of Contents, Introduction and Constant Region Sequences sections), 5th edition, Bethesda, Md.:NIH vol. 1:647-723 (1991); Kabat et al., "Introduction" *Sequences of Proteins of Immunological Interest*, US Dept of Health and Human Services, NIH, 5th edition, Bethesda, Md. vol. 1:xiii-xcvi (1991); Chothia & Lesk, *J. Mol. Biol.* 196:901-917 (1987); Chothia et al., *Nature* 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain has reduced effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting IL-2 molecule. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide of the invention consists of, consists essentially of, or comprises an amino acid sequence selected from SEQ ID NOs: 2, 4, 6, 8, 12, 14, 16, 18, 20, 22, 24, 26, 28, 30, and 32. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID NOs: 2, 4, 6, 8, 12, 14, 16, 18, 20, 22, 24, 26, 28, 30, and 32. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID NOs: 2, 4, 6, 8, 12, 14, 16, 18, 20, 22, 24, 26, 28, 30, and 32. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID NOs: 2, 4, 6, 8, 12, 14, 16, 18, 20, 22, 24, 26, 28, 30, and 32.

In an embodiment, the peptides of the invention are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like. In an embodiment, the nucleotide sequence of the invention comprises, consists of, or consists essentially of, a nucleotide sequence selected from SEQ ID NOs: 1, 3, 5, 7, 11, 13, 15, 17, 19, 21, 23, 25, 27, 29, and 31. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID NOs: 1, 3, 5, 7, 11, 13, 15, 17, 19, 21, 23, 25, 27, 29, and 31. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID NOs: 1, 3, 5, 7, 11, 13, 15, 17, 19, 21, 23, 25, 27, 29, and 31. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID NOs: 1, 3, 5, 7, 11, 13, 15, 17, 19, 21, 23, 25, 27, 29, and 31.

It will also be understood by one of ordinary skill in the art that the extended-PK IL-2 of the invention may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The IL-2 and Fc molecules of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The term "ameliorating" refers to any therapeutically beneficial result in the treatment of a disease state, e.g., cancer, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser($Gly_4$Ser)n. In one embodiment, n=1. In one embodiment, n=2. In another embodiment, n=3, i.e., Ser($Gly_4$Ser)3. In another embodiment, n=4, i.e., Ser ($Gly_4$Ser)4. In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises the amino acid sequence ($Gly_4$Ser)n. In one embodiment, n=1. In one embodiment, n=2. In a preferred embodiment, n=3. In another embodiment, n=4. In another embodiment, n=5. In yet another embodiment, n=6. Another exemplary gly-ser polypeptide linker comprises the amino acid sequence ($Gly_3$Ser)n. In one embodiment, n=1. In one embodiment, n=2. In a preferred embodiment, n=3. In another embodiment, n=4. In another embodiment, n=5. In yet another embodiment, n=6.

As used herein, the terms "linked," "fused", or "fusion" are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "half-life" refers to the time taken for the serum or plasma concentration of a polypeptide to reduce by 50%, in vivo, for example due to degradation and/or clearance or sequestration by natural mechanisms. The extended-PK IL-2 of the present invention is stabilized in vivo and its half-life increased by, e.g., fusion to an Fc region, through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound of the invention to a subject; collecting blood samples or other samples from said subject at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

A "therapeutic antibody" is an antibody, fragment of an antibody, or construct that is derived from an antibody, and can bind to a cell-surface antigen on a target cell to cause a therapeutic effect. Such antibodies can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in combination therapy with extended-PK IL-2 of the present invention. Therapeutic antibodies may be monoclonal antibodies or polyclonal antibodies. In preferred embodiments, the therapeutic antibodies target cancer antigens.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, a "small molecule" is a molecule with a molecular weight below about 500 Daltons.

As used herein, "therapeutic protein" refers to any polypeptide, protein, protein variant, fusion protein and/or fragment thereof which may be administered to a subject as a medicament. An exemplary therapeutic protein is an interleukin, e.g., IL-7.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect, e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regiment that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy. As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Overview

In one aspect, the present invention relates to methods of treating cancer in a subject comprising administering an extended-pharmacokinetic (PK) interleukin (IL)-2, and a therapeutic agent, e.g., a therapeutic antibody, in an amount effective to treat cancer. In some aspects, the extended-PK IL-2 comprises a fusion protein, wherein the fusion comprises an IL-2 moiety and another moiety, such as an immunoglobulin fragment, a conjugated non-protein polymer, human serum albumin, or Fn3. In a preferred embodiment, the non-IL-2 moiety of the fusion is an Fc domain, preferably the Fc region from human IgG1. In some aspects, the Fc domain is mutated so as to reduce binding to Fcγ receptors, complement proteins, or both. Such Fc domains exhibit reduced effector functions. One such mutant is an Fc region in which the aspartic acid residue at position 265 is mutated to alanine. In some embodiments, the fusion protein comprises a monomer of one IL-2 moiety linked to an Fc domain as a heterodimer. In other embodiments, the fusion protein comprises a dimer of two IL-2 moieties linked to an Fc domain as a heterodimer (i.e., bivalent IL-2). The invention also relates to novel IL-2 mutants that exhibit high affinity binding to the IL-2R alpha receptor (i.e., CD25). These IL-2 mutants are suited for use in the methods of the present invention.

The therapeutic agent to be used in conjunction with extended-PK IL-2 can be, for example, a therapeutic antibody, a therapeutic protein, a small molecule, an antigen, or a population of cells (e.g., a population of ex vivo expanded CD8+ T cells). In a preferred embodiment, the therapeutic agent is a therapeutic antibody. In some embodiments, more than one therapeutic agent can be included in the combination therapy with extended PK-IL2. Extended-PK IL-2 and the therapeutic agent can be administered simultaneously or sequentially. In some embodiments, the extended-PK IL-2 and the therapeutic agent are administered within three days of each other.

IL-2 signals through a receptor complex consisting of IL-2Rα, IL-2Rβ, and IL-2Rγ. The signaling events resulting from IL-2 stimulation are initiated by ligand-induced oligomerization of these receptor subunits. In particular, the α, β, and $\gamma_c$ chains recognize distinct sites on IL-2 and associate with IL-2 in a stepwise manner, with IL-2Rα binding IL-2 leading to subsequent recruitment of IL-2Rβ and $\gamma_c$ and downstream signaling. This signaling promotes proliferation and cell survival. Accordingly, in one embodiment, the present invention relates to a method of increasing IL-2Rβ and IL-2Rγ gamma signaling in a lymphocyte by administering a therapeutic agent or agents in an amount effective for stimulating the IL-2Rβγ complex. In one embodiment, the therapeutic agent is an extended-PK IL-2.

Figure 18:
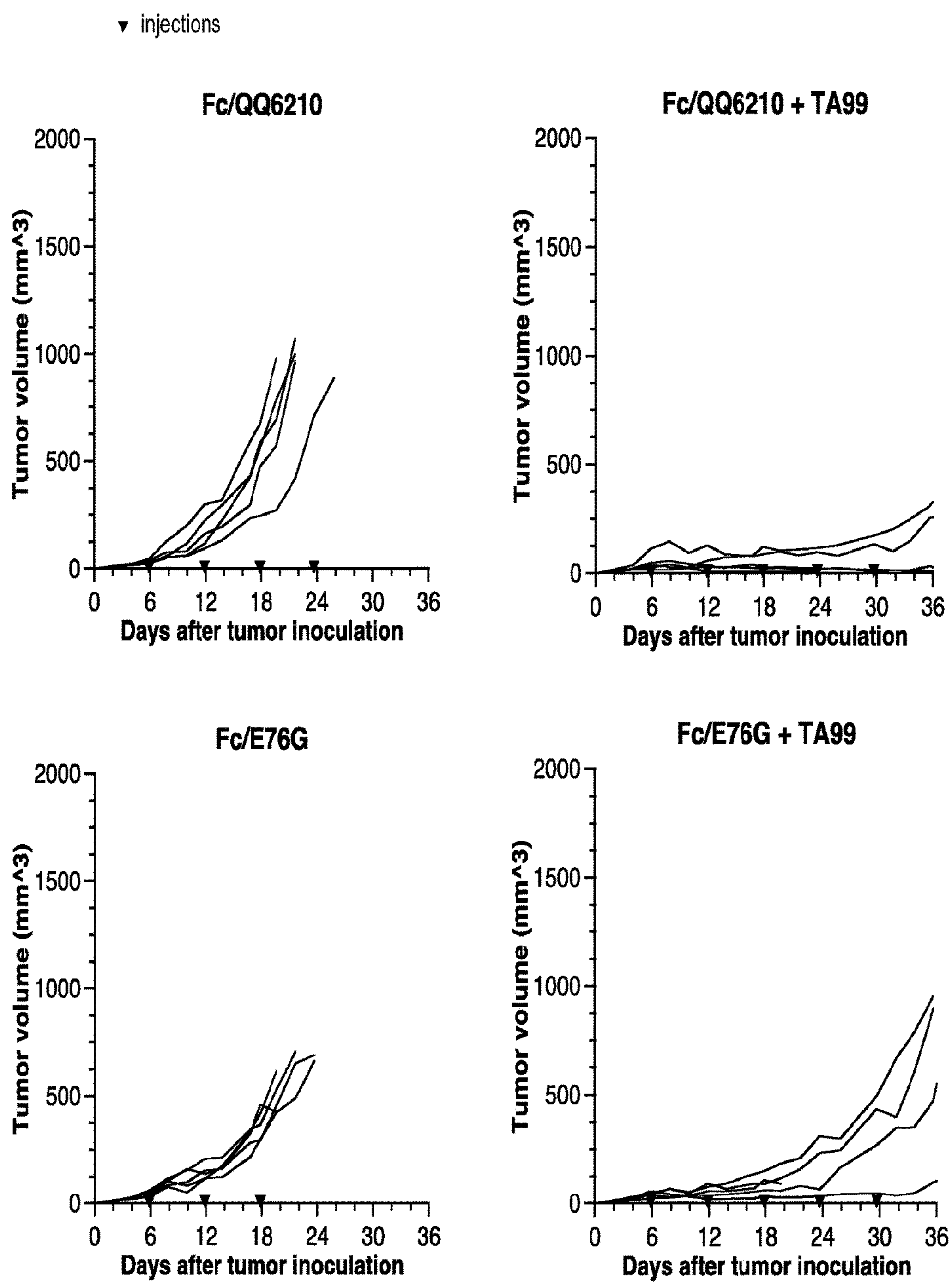
FIG. 18 is a series of graphs demonstrating that CD25 binding affinity is required for maximal Fc/IL-2+TA99 combination therapy. C57BL/6 mice (n=5 mice/group) were injected subcutaneously with $10^6$ B16-F10 melanoma cells. Six days after tumor inoculation, mice were injected intravenously with 25 μg Fc/QQ6210 or Fc/E76G, alone or with 100 μg TA99. Subsequent doses were administered every 6 days. Each individual line represents one mouse and inverted triangles represent an injection of the indicated regimen.

In another embodiment, the therapeutic agent is a IL-15 superagonist/IL-15Rα complex (IL-15 shares IL-2Rβγ subunits with IL-2 for downstream signaling), such as that disclosed in Rubinstein et al. (*PNAS,* 2006; 103:9166-71). The IL-15 superagonist/IL-15Rα complex alone may have prolonged serum half-life given its bulky size, thereby allowing for prolonged IL-2Rβγ signaling. Indeed, as described in the Examples, extended-PK IL-2 that does not bind to IL-2Rα exerted a therapeutic benefit against tumor growth, suggesting that an agent(s) that promotes IL-2Rβγ signaling will also likely have a therapeutic effect in the treatment of cancer. As shown in FIG. 18, extended-PK IL-2 variants lacking CD25 binding still exert some therapeutic effect, albeit less than when capable of CD25 binding.

In yet another embodiment, the therapeutic agent is an IL-2/anti-IL-2 antibody complex that specifically activates IL-2Rβγ signaling (such as that disclosed in Krieg et al.

(*PNAS* 2010; 107:11906-11)) in combination with another therapeutic antibody. While CD25 binding is not required for the therapeutic effects of the therapeutic agents of the present invention, in preferred embodiments, the agent(s) have CD25 binding ability.

The methods of the invention are also useful for reducing tumor growth or size in a subject. In one embodiment, extended-PK IL-2 in combination with one or more therapeutic antibodies, with or without one or more additional agents, is administered to a subject with established tumors in an amount sufficient to reduce tumor growth or size in the subject. In some embodiments, tumor growth or size is decreased by about 30%, about 50%, about 70%, or about 90% compared to the size of the tumor prior to the combination therapy.

In another embodiment, the methods of the present invention are useful for inhibiting the growth and/or proliferation of tumor cells in a subject by administering an extended-PK IL-2 and a therapeutic antibody in an amount effective to inhibit growth and/or proliferation of tumor cells in the subject. In one embodiment, the combination therapy of extended-PK IL-2 and a therapeutic antibody results in enhanced or increased suppression of tumor or tumor cell growth as compared to unmodified IL-2 (e.g., recombinant human IL-2).

In other embodiments, the methods of the present invention are useful for prolonging the survival of a subject with a tumor by administering an extended-PK IL-2, and a therapeutic antibody in an amount effective to prolong survival in the subject. In one embodiment, the survival of the subject, e.g., a mouse model of cancer, is extended by 5 days or more, 10 days or more, 15 days or more, 20 days or more, 25 days or more, 30 days or more, 35 days or more, 40 days or more, or 45 days or more. In another embodiment, the methods of the invention are useful for inhibiting the metastasis of tumors by administering a therapeutically effective amount of extended-PK IL-2 and one or more therapeutic agents to a subject with established tumors. Preferably, the extended-PK IL-2 and therapeutic antibody reduces tumor size to a greater extent than that achieved by a combination of IL-2 and one or more therapeutic agents.

In another embodiment, the methods of the invention relate to increasing recruitment of lymphocytes to the periphery of a tumor in a subject by administering an extended-PK IL-2 and a therapeutic antibody in an amount effective to increase recruitment of lymphocytes to the periphery of the tumor.

In yet another embodiment, the methods of the present invention are useful for stimulating T cell and/or NK cell activity and/or proliferation in a subject by administering an extended-PK IL-2, and a therapeutic antibody in an amount effective to stimulate T cells and/or NK cells in a subject. In another embodiment, the methods of the present invention are useful for enhancing antibody-dependent cell-mediated cytotoxicity (ADCC) and/or cytotoxic T lymphocyte (CTL) responses in a subject comprising administering an extended-PK IL-2, and a therapeutic antibody in an amount effective to enhance ADCC and/or CTL in the subject. In yet another embodiment, the methods of the invention are useful for increasing the number of CD8+ T cells in a subject by administering an extended-PK IL-2, and a therapeutic antibody in an amount effective to increase the number of CD8+ T cells in the subject. In yet another embodiment, the methods of the invention are useful for increasing the number of NK cells in a subject by administering an extended-PK IL-2, and a therapeutic antibody in an amount effective to increase the number of NK cells in the subject. In some embodiments the number of CD8+ T cells and/or NK cells are increased by 2-fold or more, 3-fold or more, 4-fold or more, or 5-fold or more.

In yet another embodiment, the methods of the present invention are useful for treating cancer and reducing vascular leak syndrome associated with IL-2 therapy in a subject by administering an extended-PK IL-2, and a therapeutic antibody in an amount effective to treat cancer and reduce vascular leak syndrome associated with IL-2 therapy in the subject. In another embodiment, the methods of the present invention are useful for treating cancer and reducing pulmonary edema associated with IL-2 therapy in a subject by administering an extended-pharmacokinetic (PK) interleukin (IL)-2, and a therapeutic antibody in an amount effective to treat cancer and reduce pulmonary edema associated with IL-2 therapy in the subject.

IL-2 Mutants

Site-directed mutagenesis was used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In one embodiment, the invention features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants of the present invention which are high affinity binders include those shown in FIG. 1, such as those with amino acid sequences set forth in SEQ ID NOs: 4, 20, 22, 24, 26, and 28. Further exemplary IL-2 mutants with increased affinity for CD25 are disclosed in U.S. Pat. No. 7,569,215, the contents of which are incorporated herein by reference. In one embodiment, the IL-2 mutant is does not bind to CD25, e.g., those with amino acid sequences set forth in SEQ ID NOs: 6 and 8.

IL-2 mutants include an amino acid sequence that is at least 80% identical to SEQ ID NO:30 and that bind CD25. For example, an IL-2 mutant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586) of SEQ ID NO: 29; amino acid sequence (accession: P60568) of SEQ ID NO: 30) or human IL-2 without the signal peptide (nucleic acid sequence of SEQ ID NO: 31; amino acid sequence of SEQ ID NO: 32). Accordingly, in preferred embodiments, the IL-2 moiety of the extended-PK IL-2 is human IL-2. In other embodiments, the IL-2 moiety of the extended-PK IL-2 is a mutant human IL-2.

IL-2 mutants can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO:30 is a polypeptide that includes a sequence that is identical to the reference sequence except for the inclusion of up to five alterations of the reference amino acid of SEQ ID NO:30. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

In general, the polypeptides used in the practice of the instant invention will be synthetic, or produced by expression of a recombinant nucleic acid molecule. In the event the polypeptide is an extended-PK IL-2 (e.g., a fusion protein containing at least IL-2 and a heterologous polypeptide, such as a hexa-histidine tag or hemagglutinin tag or an Fc region or human serum albumin), it can be encoded by a hybrid nucleic acid molecule containing one sequence that encodes IL-2 and a second sequence that encodes all or part of the heterologous polypeptide.

The techniques that are required to make IL-2 mutants are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of IL-2 mutants). Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating IL-2 mutants via expression of nucleic acid molecules that have been altered by recombinant molecular biological techniques, IL-2 mutants can be chemically synthesized. Chemically synthesized polypeptides are routinely generated by those of skill in the art.

As noted above, IL-2 can also be prepared as fusion or chimeric polypeptides that include IL-2 and a heterologous polypeptide (i.e., a polypeptide that is not IL-2). The heterologous polypeptide can increase the circulating half-life of the chimeric polypeptide in vivo, and may, therefore, further enhance the properties of IL-2. As discussed in further detail infra, the polypeptide that increases the circulating half-life may be a serum albumin, such as human serum albumin, or the Fc region of the IgG subclass of antibodies that lacks the IgG heavy chain variable region. The Fc region can include a mutation that inhibits effector functions such as complement fixation and Fc receptor binding.

In other embodiments, the chimeric polypeptide can include IL-2 and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

Chimeric polypeptides can be constructed using no more than conventional molecular biological techniques, which are well within the ability of those of ordinary skill in the art to perform.

Nucleic Acid Molecules Encoding IL-2 Mutants

IL-2, either alone or as a part of a chimeric polypeptide, such as those described above, can be obtained by expression of a nucleic acid molecule. Thus, nucleic acid molecules encoding polypeptides containing an IL-2 mutant are considered within the scope of the invention, such as those with nucleic acid sequences set forth in SEQ ID NOs: 1, 3, 5, 7, 11, 13, 15, 17, 19, 21, 23, 25, 27, 29, and 31. Just as IL-2 mutants can be described in terms of their identity with wild-type IL-2, the nucleic acid molecules encoding them will necessarily have a certain identity with those that encode wild-type IL-2. For example, the nucleic acid molecule encoding an IL-2 mutant can be at least 50%, at least 65%, preferably at least 75%, more preferably at least 85%, and most preferably at least 95% (e.g., 99%) identical to the nucleic acid encoding full length wild-type IL-2 (e.g., SEQ ID NO:29) or wild-type IL-2 without the signal peptide (e.g., SEQ ID NO: 31).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules of the invention can include fragments not found as such in the natural state. Thus, the invention encompasses recombinant molecules, such as those in which a nucleic acid sequence (for example, a sequence encoding an IL-2 mutant) is incorporated into a vector (e.g., a plasmid or viral vector) or into the genome of a heterologous cell (or the genome of a homologous cell, at a position other than the natural chromosomal location).

As described above, IL-2 mutants of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include .beta.-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids of the invention (and the polypeptides they encode) can be those of a mouse, rat, guinea pig, cow, sheep, horse, pig, rabbit, monkey, baboon, dog, or cat. Typically, the nucleic acid molecules will be those of a human.

Expression of IL-2 Mutants

The nucleic acid molecules described above can be contained within a vector that is capable of directing their expression in, for example, a cell that has been transduced with the vector. Accordingly, in addition to IL-2 mutants, expression vectors containing a nucleic acid molecule encoding an IL-2 mutant and cells transfected with these vectors are among the preferred embodiments.

Vectors suitable for use in the present invention include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an IL-2 mutant are also features of the invention. A cell of the invention is a transfected cell, i.e., a cell into which a nucleic acid molecule, for example a nucleic acid molecule encoding an IL-2 mutant, has been introduced by means of recombinant DNA techniques. The progeny of such a cell are also considered within the scope of the invention.

The precise components of the expression system are not critical. For example, an IL-2 mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Extended-PK Groups

As described supra, IL-2 or mutant IL-2 is fused to an extended-PK group, which increases circulation half-life. Non-limiting examples of extended-PK groups are described infra. It should be understood that other PK groups that increase the circulation half-life of IL-2, or variants thereof, are also applicable to the present invention. In a preferred embodiment, the extended-PK group is a Fc domain.

In some embodiments, the serum half-life of extended-PK IL-2 is increased relative to IL-2 alone (i.e., IL-2 not fused to an extended-PK group). In certain embodiments, the serum half-life of extended-PK IL-2 is at least 20, 40, 60, 80, 100, 120, 150, 180, 200, 400, 600, 800, or 1000% longer relative to the serum half-life of IL-2 alone. In other embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of IL-2 alone. In some embodiments, the serum half-life of the extended-PK IL-2 is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

Fc Domains

In some embodiments, an extended-PK IL-2 includes an Fc domain, such as that with an amino acid sequences set forth in SEQ ID NO: 34. It will be understood by those in the art that epitope tags corresponding to 6× his tag on these extended-PK IL-2 with Fc domains are optional. The Fc domain does not contain a variable region that binds to antigen. Fc domains useful for producing the extended-PK IL-2 of the present invention may be obtained from a number of different sources. In preferred embodiments, an Fc domain of the extended-PK IL-2 is derived from a human immunoglobulin. In a preferred embodiment, the Fc domain is from a human IgG1 constant region (SEQ ID NO: 33). The Fc domain of human IgG1 is set forth in SEQ ID NO:

34. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some aspects, an extended-PK IL-2 includes a mutant Fc domain. In some aspects, an extended-PK IL-2 includes a mutant, IgG1 Fc domain. In some aspects, a mutant Fc domain comprises one or more mutations in the hinge, CH2, and/or CH3 domains. In some aspects, a mutant Fc domain includes a D265A mutation.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. *Biochem Biophys Res Commun* 1989; 160:1250). The cloning of antibody sequences is further described in Newman et al., U.S. Pat. No. 5,658,570, filed Jan. 25, 1995, which is herein incorporated by reference.

Extended-PK IL-2 of the invention may comprise one or more Fc domains (e.g., 2, 3, 4, 5, 6, 7, 8, 9, 10, or more Fc domains). In one embodiment, the Fc domains may be of different types. In one embodiment, at least one Fc domain present in the extended-PK IL-2 comprises a hinge domain or portion thereof. In another embodiment, the extended-PK IL-2 of the invention comprises at least one Fc domain which comprises at least one CH2 domain or portion thereof. In another embodiment, the extended-PK IL-2 of the invention comprises at least one Fc domain which comprises at least one CH3 domain or portion thereof. In another embodiment, the extended-PK IL-2 of the invention comprises at least one Fc domain which comprises at least one CH4 domain or portion thereof. In another embodiment, the extended-PK IL-2 of the invention comprises at least one Fc domain which comprises at least one hinge domain or portion thereof and at least one CH2 domain or portion thereof (e.g, in the hinge-CH2 orientation). In another embodiment, the extended-PK IL-2 of the invention comprises at least one Fc domain which comprises at least one CH2 domain or portion thereof and at least one CH3 domain or portion thereof (e.g, in the CH2-CH3 orientation). In another embodiment, the extended-PK IL-2 of the invention comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, extended-PK IL-2 comprises at least one complete Fc region derived from one or more immunoglobulin heavy chains (e.g., an Fc domain including hinge, CH2, and CH3 domains, although these need not be derived from the same antibody). In other embodiments, extended-PK IL-2 comprises at least two complete Fc domains derived from one or more immunoglobulin heavy chains. In preferred embodiments, the complete Fc domain is derived from a human IgG immunoglobulin heavy chain (e.g., human IgG1).

In another embodiment, the extended-PK IL-2 of the invention comprises at least one Fc domain comprising a complete CH3 domain. In another embodiment, the extended-PK IL-2 of the invention comprises at least one Fc domain comprising a complete CH2 domain. In another embodiment, the extended-PK IL-2 of the invention comprises at least one Fc domain comprising at least a CH3 domain, and at least one of a hinge region, and a CH2 domain. In one embodiment, the extended-PK IL-2 of the invention comprises at least one Fc domain comprising a hinge and a CH3 domain. In another embodiment, the extended-PK IL-2 of the invention comprises at least one Fc domain comprising a hinge, a CH2, and a CH3 domain. In preferred embodiments, the Fc domain is derived from a human IgG immunoglobulin heavy chain (e.g., human IgG1).

The constant region domains or portions thereof making up an Fc domain of the extended-PK IL-2 of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, the extended-PK IL-2 can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In one embodiment, the extended-PK IL-2 of the invention lacks one or more constant region domains of a complete Fc region, i.e., they are partially or entirely deleted. In certain embodiments, the extended-PK IL-2 of the invention will lack an entire CH2 domain. In certain embodiments, the extended-PK IL-2 of the invention comprise CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

Changes to Fc Amino Acids

In certain embodiments, an Fc domain employed in the extended-PK IL-2 of the invention is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the extended-PK IL-2 of the invention comprise an Fc variant comprising more than one amino acid substitution. The extended-PK IL-2 of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In some aspects, an Fc domain includes changes in the region between amino acids 234-238, including the sequence LLGGP at the beginning of the CH2 domain. In some aspects, an Fc variant alters Fc mediated effector function, particularly ADCC, and/or decrease binding avidity for Fc receptors. In some aspects, sequence changes closer to the CH2-CH3 junction, at positions such as K322 or P331 can eliminate complement mediated cytotoxicity and/or alter avidity for FcR binding. In some aspects, an Fc domain incorporates changes at residues P238 and P331, e.g., changing the wild type prolines at these positions to serine. In some aspects, alterations in the hinge region at one or more of the three hinge cysteines, to encode CCC, SCC, SSC, SCS, or SSS at these residues can also affect FcR binding and molecular homogeneity, e.g., by elimination of unpaired cysteines that may destabilize the folded protein.

Other amino acid mutations in the Fc domain are contemplated to reduce binding to the Fc gamma receptor and Fc gamma receptor subtypes. For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety.

Further mutations contemplated for use include, e.g., those described in U.S. Pat. App. Pub. No. 2006/0235208, published Oct. 19, 2006 and incorporated herein by reference in its entirety. This publication describes Fc variants that exhibit reduced binding to Fc gamma receptors, reduced antibody dependent cell-mediated cytotoxicity, or reduced complement dependent cytotoxicity, that comprise at least one amino acid modification in the Fc region, including 232G, 234G, 234H, 235D, 235G, 235H, 236I, 236N, 236P, 236R, 237K, 237L, 237N, 237P, 238K, 239R, 265G, 267R, 269R, 270H, 297S, 299A, 299I, 299V, 325A, 325L, 327R, 328R, 329K, 330I, 330L, 330N, 330P, 330R, and 331L (numbering is according to the EU index), as well as double mutants 236R/237K, 236R/325L, 236R/328R, 237K/325L, 237K/328R, 325L/328R, 235G/236R, 267R/269R, 234G/235G, 236R/237K/325L, 236R/325L/328R, 235G/236R/237K, and 237K/325L/328R. Other mutations contemplated for use as described in this publication include 227G, 234D, 234E, 234G, 234I, 234Y, 235D, 235I, 235S, 236S, 239D, 246H, 255Y, 258H, 260H, 2641, 267D, 267E, 268D, 268E, 272H, 272I, 272R, 281D, 282G, 283H, 284E, 293R, 295E, 304T, 324G, 324I, 327D, 327A, 328A, 328D, 328E, 328F, 328I, 328M, 328N, 328Q, 328T, 328V, 328Y, 330I, 330L, 330Y, 332D, 332E, 335D, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 297 and 298, an insertion of A between positions 297 and 298, an insertion of S between positions 297 and 298, an insertion of D between positions 297 and 298, an insertion of G between positions 326 and 327, an insertion of A between positions 326 and 327, an insertion of T between positions 326 and 327, an insertion of D between positions 326 and 327, and an insertion of E between positions 326 and 327 (numbering is according to the EU index). Additionally, mutations described in U.S. Pat. App. Pub. No. 2006/0235208 include 227G/332E, 234D/332E, 234E/332E, 234Y/332E, 234I/332E, 234G/332E, 235I/332E, 235S/332E, 235D/332E, 235E/332E, 236S/332E, 236A/332E, 236S/332D, 236A/332D, 239D/268E, 246H/332E, 255Y/332E, 258H/332E, 260H/332E, 264I/332E, 267E/332E, 267D/332E, 268D/332D, 268E/332D, 268E/332E, 268D/332E, 268E/330Y, 268D/330Y, 272R/332E, 272H/332E, 283H/332E, 284E/332E, 293R/332E, 295E/332E, 304T/332E, 324I/332E, 324G/332E, 324I/332D, 324G/332D, 327D/332E, 328A/332E, 328T/332E, 328V/332E, 328I/332E, 328F/332E, 328Y/332E, 328M/332E, 328D/332E, 328E/332E, 328N/332E, 328Q/332E, 328A/332D, 328T/332D, 328V/332D, 328I/332D, 328F/332D, 328Y/332D, 328M/332D, 328D/332D, 328E/332D, 328N/332D, 328Q/332D, 330L/332E, 330Y/332E, 330I/332E, 332D/330Y, 335D/332E, 239D/332E, 239D/332E/330Y, 239D/332E/330L, 239D/332E/330I, 239D/332E/268E, 239D/332E/268D, 239D/332E/327D, 239D/332E/284E, 239D/268E/330Y, 239D/332E/268E/330Y, 239D/332E/327A, 239D/332E/268E/327A, 239D/332E/330Y/327A, 332E/330Y/268 E/327A, 239D/332E/268E/330Y/327A, Insert G>297-298/332E, Insert A>297-298/332E, Insert S>297-298/332E, Insert D>297-298/332E, Insert G>326-327/332E, Insert A>326-327/332E, Insert T>326-327/332E, Insert D>326-327/332E, Insert E>326-327/332E, Insert G>235-236/332E, Insert A>235-236/332E, Insert S>235-236/332E, Insert T>235-236/332E, Insert N>235-236/332E, Insert D>235-236/332E, Insert V>235-236/332E, Insert L>235-236/332E, Insert G>235-236/332D, Insert A>235-236/332D, Insert S>235-236/332D, Insert T>235-236/332D, Insert N>235-236/332D, Insert D>235-236/332D, Insert V>235-236/332D, and Insert L>235-236/332D (numbering according to the EU index) are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. In a preferred embodiment, the mutation is D265A in human IgG1.

In certain embodiments, the extended-PK IL-2 of the invention comprises an amino acid substitution to an Fc domain which alters the antigen-independent effector functions of the antibody, in particular the circulating half-life of the antibody.

In other embodiments, the extended-PK IL-2 of the invention comprises an Fc variant comprising an amino acid substitution which alters the antigen-dependent effector functions of the polypeptide, in particular ADCC or complement activation, e.g., as compared to a wild type Fc region. Such extended-PK IL-2 exhibit decreased binding to FcR gamma when compared to wild-type polypeptides and, therefore, mediate reduced effector function. Fc variants with decreased FcR gamma binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation.

In one embodiment, the extended-PK IL-2 exhibits altered binding to an activating FcγR (e.g. FcγI, FcγIIa, or FcγRIIIa). In another embodiment, the extended-PK IL-2 exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

The extended-PK IL-2 of the invention may also comprise an amino acid substitution which alters the glycosylation of the extended-PK IL-2. For example, the Fc domain of the extended-PK IL-2 may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the extended-PK IL-2 has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, which are incorporated by reference herein.

In other embodiments, the extended-PK IL-2 of the invention comprises at least one Fc domain having engineered cysteine residue or analog thereof which is located at the solvent-exposed surface. In preferred embodiments, the extended-PK IL-2 of the invention comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the extended-PK IL-2 of the invention may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the extended-PK IL-2 of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the extended-PK IL-2 of the invention may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

PEGylation

In some embodiments, an extended-PK IL-2 of the present invention includes a polyethylene glycol (PEG) domain. PEGylation is well known in the art to confer increased circulation half-life to proteins. Methods of PEGylation are well known and disclosed in, e.g., U.S. Pat. No. 7,610,156, U.S. Pat. No. 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$, where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462, both of which are hereby incorporated by reference. One form of PEGs includes two PEG side-chains (PEG2) linked via the primary amino groups of a lysine (Monfardini et al., *Bioconjugate Chem* 1995; 6:62-9).

In one embodiment, pegylated IL-2 is produced by site-directed pegylation, particularly by conjugation of PEG to a cysteine moiety at the N- or C-terminus. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252:3582, and Harris et. al., in: Poly(ethylene glycol) Chemistry: Biotechnical and Biomedical Applications; (J. M. Harris ed.) Plenum Press: New York, 1992; Chap. 21 and 22).

A variety of molecular mass forms of PEG can be selected, e.g., from about 1,000 Daltons (Da) to 100,000 Da (n is 20 to 2300), for conjugating to IL-2. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the pegylated IL-2 will be used therapeutically, the desired dosage, circulation time, resistance to proteolysis, immunogenicity, and other considerations. For a discussion of PEG and its use to enhance the properties of proteins, see N. V. Katre, *Advanced Drug Delivery Reviews* 1993; 10:91-114.

In one embodiment of the invention, PEG molecules may be activated to react with amino groups on IL-2 such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In one embodiment, carbonate esters of PEG are used to form the PEG-IL-2 conjugates. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of IL-2 can be performed according to the methods of the state of the art, for example by reaction of IL-2 with electrophilically active PEGs (Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69).

In another embodiment, PEG molecules may be coupled to sulfhydryl groups on IL-2 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. No. 6,610,281 and U.S. Pat. No. 5,766,897 describe exemplary reactive PEG species that may be coupled to sulfhydryl groups.

In some embodiments where PEG molecules are conjugated to cysteine residues on IL-2 the cysteine residues are native to IL-2 whereas in other embodiments, one or more cysteine residues are engineered into IL-2. Mutations may be introduced into the coding sequence of IL-2 to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In another embodiment, pegylated IL-2 comprise one or more PEG molecules covalently attached to a linker.

In one embodiment, IL-2 is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5):1005-1009.

Monopegylation of IL-2 can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of IL-2 to activated PEG in the conjugation reaction can be from about 1:0.5 to 1:50, between from about 1:1 to 1:30, or from about 1:5 to 1:15. Various aqueous buffers can be used to catalyze the covalent addition of PEG to IL-2, or variants thereof. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated IL-2, such as size exclusion (e.g. gel filtration) and ion exchange chromatography. Products may also be separated using SDS-PAGE. Products that may be separated include mono-, di-, tri-poly- and un-pegylated IL-2 as well as free PEG. The percentage of mono-PEG conjugates can be controlled by pooling broader fractions around the elution peak to increase the percentage of mono-PEG in the composition.

In one embodiment, PEGylated IL-2 of the invention contain one, two or more PEG moieties. In one embodiment, the PEG moiety(ies) are bound to an amino acid residue which is on the surface of the protein and/or away from the surface that contacts CD25. In one embodiment, the combined or total molecular mass of PEG in PEG-IL-2 is from about 3,000 Da to 60,000 Da, optionally from about 10,000 Da to 36,000 Da. In one embodiment, PEG in pegylated IL-2 is a substantially linear, straight-chain PEG.

In one embodiment, pegylated IL-2 of the invention will preferably retain at least 25%, 50%, 60%, 70%, 80%, 85%, 90%, 95% or 100% of the biological activity associated with the unmodified protein. In one embodiment, biological activity refers to the ability to bind CD25.

The serum clearance rate of PEG-modified IL-2 may be decreased by about 10%, 20%, 30%, 40%, 50%, 60%, 70%, 80%, or even 90%, relative to the clearance rate of the unmodified IL-2. PEG-modified IL-2 may have a circulation half-life ($t_{1/2}$) which is enhanced relative to the half-life of unmodified IL-2. The half-life of PEG-IL-2, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of unmodified IL-2. In some embodiments, the protein half-life is determined in vitro, such as in a buffered saline solution or in serum. In other embodiments, the protein half-life is an in vivo circulation half-life, such as the half-life of the protein in the serum or other bodily fluid of an animal.

Other Extended-PK Groups

In some embodiments, the extended-PK group is a serum albumin, or fragments thereof. Methods of fusing serum albumin to proteins are disclosed in, e.g., US2010/0144599, US2007/0048282, and US2011/0020345, which are herein incorporated by reference in their entirety. In some embodiments, the extended-PK group is human serum albumin. In some embodiments, the extended-PK group is transferrin.

In some embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

In some embodiments, the extended-PK group is a serum immunoglobulin binding protein such as those disclosed in US2007/0178082, which is herein incorporated by reference in its entirety.

In some embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

Linkers

In some embodiments, the extended-PK group is optionally fused to IL-2 via a linker. Linkers suitable for fusing the extended-PK group to IL-2 are well known in the art, and are disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In a preferred embodiment, the linker is a gly-ser polypeptide linker, i.e., a peptide that consists of glycine and serine residues.

Exemplary gly-ser polypeptide linkers comprise the amino acid sequence Ser($Gly_4$Ser)n. In one embodiment, n=1. In one embodiment, n=2. In another embodiment, n=3, i.e., Ser($Gly_4Ser)_3$. In another embodiment, n=4, i.e., Ser ($Gly_4$Ser)4. In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises the amino acid sequence Ser ($Gly_4$Ser)n. In one embodiment, n=1. In one embodiment, n=2. In a preferred embodiment, n=3. In another embodiment, n=4. In another embodiment, n=5. In yet another embodiment, n=6. Another exemplary gly-ser polypeptide linker comprises ($Gly_4$Ser)n. In one embodiment, n=1. In one embodiment, n=2. In a preferred embodiment, n=3. In another embodiment, n=4. In another embodiment, n=5. In yet another embodiment, n=6. Another exemplary gly-ser polypeptide linker comprises ($Gly_3$Ser)n. In one embodiment, n=1. In one embodiment, n=2. In a preferred embodiment, n=3. In another embodiment, n=4. In another embodiment, n=5. In yet another embodiment, n=6.

Therapeutic Agents

The extended-PK IL-2 of the present invention can be used in conjunction with one or more therapeutic agents. In one embodiment, the therapeutic agent is a therapeutic antibody. In another embodiment, the therapeutic agent is a therapeutic protein. In another embodiment, the therapeutic agent is a small molecule. In another embodiment, the therapeutic agent is an antigen. In another embodiment, the therapeutic agent is a population of cells. In a preferred embodiment, the therapeutic agent is a therapeutic antibody.

Therapeutic Antibodies

In one embodiment, the methods of the invention can be performed with extended-PK IL-2 together with a therapeutic antibody.

Methods of producing antibodies, and antigen-binding fragments thereof, are well known in the art and are disclosed in, e.g., U.S. Pat. No. 7,247,301, US2008/0138336, and U.S. Pat. No. 7,923,221, all of which are herein incorporated by reference in their entirety.

Therapeutic antibodies that can be used in the methods of the present invention include, but are not limited to, any of the art-recognized anti-cancer antibodies that are approved for use, in clinical trials, or in development for clinical use. In some embodiments, more than one anti-cancer antibody can be included in the combination therapy of the present invention.

Non-limiting examples of anti-cancer antibodies include the following, without limitation:

trastuzumab (HERCEPTIN™. by Genentech, South San Francisco, Calif.), which is used to treat HER-2/neu positive breast cancer or metastatic breast cancer;

bevacizumab (AVASTIN™ by Genentech), which is used to treat colorectal cancer, metastatic colorectal cancer, breast cancer, metastatic breast cancer, non-small cell lung cancer, or renal cell carcinoma;

rituximab (RITUXAN™ by Genentech), which is used to treat non-Hodgkin's lymphoma or chronic lymphocytic leukemia;

pertuzumab (OMNITARG™ by Genentech), which is used to treat breast cancer, prostate cancer, non-small cell lung cancer, or ovarian cancer;

cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer;

IMC-1C11 (ImClone Systems Incorporated), which is used to treat colorectal cancer, head and neck cancer, as well as other potential cancer targets;

tositumomab and tositumomab and iodine $I^{131}$ (BEXXAR™ by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy;

$In^{111}$ ibirtumomab tiuxetan; $Y^{90}$ ibirtumomab tiuxetan; $I^{111}$ ibirtumomab tiuxetan and $Y^{90}$ ibirtumomab tiuxetan (ZEVALIN™ by Biogen Idec, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma;

EMD 7200 (EMD Pharmaceuticals, Durham, N.C.), which is used for treating for treating non-small cell lung cancer or cervical cancer;

SGN-30 (a genetically engineered monoclonal antibody targeted to CD30 antigen by Seattle Genetics, Bothell, Wash.), which is used for treating Hodgkin's lymphoma or non-Hodgkin's lymphoma;

SGN-15 (a genetically engineered monoclonal antibody targeted to a Lewisγ-related antigen that is conjugated to doxorubicin by Seattle Genetics), which is used for treating non-small cell lung cancer;

SGN-33 (a humanized antibody targeted to CD33 antigen by Seattle Genetics), which is used for treating acute myeloid leukemia (AML) and myelodysplastic syndromes (MDS);

SGN-40 (a humanized monoclonal antibody targeted to CD40 antigen by Seattle Genetics), which is used for treating multiple myeloma or non-Hodgkin's lymphoma;

SGN-35 (a genetically engineered monoclonal antibody targeted to a CD30 antigen that is conjugated to auristatin E by Seattle Genetics), which is used for treating non-Hodgkin's lymphoma;

SGN-70 (a humanized antibody targeted to CD70 antigen by Seattle Genetics), that is used for treating renal cancer and nasopharyngeal carcinoma;

SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present invention are not limited to those described supra. For example, the following approved therapeutic antibodies can also be used in the methods of the invention: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chromic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies for use in the present invention can also target molecules expressed by immune cells, such as, but not limited to, tremelimumab (CP-675,206) and ipilimumab (MDX-010) which targets CTLA4 and has the effect of tumor rejection, protection from rechallenge, and enhanced tumor-specific T cell responses; OX86 which targets OX40 and increases antigen-specific CD8+ T cells at tumor sites and enhances tumor rejection; CT-011 which targets PD 1 and has the effect of maintaining and expanding tumor specific memory T cells and activates NK cells; BMS-663513 which targets CD137 and causes regression of established tumors, as well as the expansion and maintenance of CD8+ T cells, and daclizumab (ZENAPAX™) which targets CD25 and causes transient depletion of CD4+ CD25+FOXP3+Tregs and enhances tumor regression and increases the number of effector T cells. A more detailed discussion of these antibodies can be found in, e.g., Weiner et al., Nature Rev. Immunol 2010; 10:317-27.

The therapeutic antibody can be a fragment of an antibody; a complex comprising an antibody; or a conjugate comprising an antibody. The antibody can optionally be chimeric or humanized or fully human.

Therapeutic Proteins

In one embodiment, the methods of the invention include administration of an extended-PK IL-2 and a therapeutic protein. Therapeutic proteins that are effective in treating cancer are well known in the art, and are disclosed in, e.g., Dranoff et al., *Nature Reviews Cancer* 2004; 4:11-22. In one embodiment, the therapeutic protein is IL-7. In another embodiment, the therapeutic protein is GM-CSF.

The heterologous nucleic acid sequence generally encodes a diagnostic or therapeutic polypeptide. In specific embodiments, the therapeutic polypeptide or protein is a "suicide protein" that causes cell death by itself or in the presence of other compounds. A representative example of such a suicide protein is thymidine kinase of the herpes simplex virus. Additional examples include thyrnidine kinase of varicella zoster virus, the bacterial gene cytosine deaminase (which converts 5-fluorocytosine to the highly toxic compound 5-fluorouracil), p450 oxidoreductase, carboxypeptidase G2, beta-glucuronidase, penicillin-V-amidase, penicillin-G-amidase, beta-lactamase, nitroreductase, carboxypeptidase A, linamarase (also referred to as .beta.-glucosidase), the *E. coli* gpt gene, and the *E. coli* Deo gene, although others are known in the art. In some embodiments, the suicide protein converts a prodrug into a toxic compound. As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-.beta.-D-arabinofuranosyl)-5-iod-ouracil) for thymidine kinase; ifosfamide for oxidoreductase; 6-methoxypurine arabinoside for VZV-TK; 5-fluorocytosine for cytosine deaminase; doxorubicin for beta-glucuronidase; CB 1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug.

In some embodiments, a therapeutic protein or polypeptide, is a cancer suppressor, for example p53 or Rb, or a nude acid encoding such a protein or polypeptide. Of course, those of skill know of a wide variety of such cancer suppressors and how to obtain them and/or the nucleic acids encoding them.

Other examples of therapeutic proteins or polypeptides include pro-apoptotic therapeutic proteins and polypeptides, for example, p15, p16, or $p21^{WAF-1}$.

Cytokines, and nucleic acid encoding them may also be used as therapeutic proteins and polypeptides. Examples include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL-1), Interleukin-Beta (IL-beta), Interleukin-2 (IL-2), Interleukin-4 (IL-4), Interleukin-5 (IL-5), Interleukin-6 (IL-6), Interleukin-7 (IL-7), Interleukin-8 (IL-8), Interleukin-10 (IL-10), Interleukin-12 (IL-12), Interleukin-13 (IL-13), Interleukin-14 (IL-14), Interleukin-15 (IL-15), Interleukin-16 (IL-16), Interleukin-18 (IL-18), Interleukin-23 (IL-23), Interleukin-24 (IL-24), although other embodiments are known in the art. In a preferred embodiment, the therapeutic protein is IL-7.

Additional examples of cytocidal genes includes, but is not limited to, mutated cyclin G1 genes. By way of example, the cytocidal gene may be a dominant negative mutation of the cyclin G1 protein (e.g., WO/01/64870).

It should be understood that the examples listed above are non-limiting, and that the methods of the present invention can be performed in conjunction with any art-recognized therapeutic protein that is effective for treating cancer when used alone or as adjunctive therapy.

Small Molecules

In one embodiment, the methods of the invention include administration of an extended-PK IL-2 and a small molecule. Small molecules that are effective in treating cancer are well known in the art, and include antagonists of factors that are involved in tumor growth, such as EGFR, ErbB2 (also known as Her2) ErbB3, ErbB4, or TNF. Non-limiting examples include small molecule receptor tyrosine kinase inhibitors (RTKIs) that target one or more tyrosine kinase receptors, such as VEGF receptors, FGF receptors, EGF receptors and PDGF receptors. Many therapeutic small molecule RTKIs are known in the art, including, but are not limited to, vatalanib (PTK787), erlotinib (TARCEVA™), OSI-7904, ZD6474 (ZACTIMA™), ZD6126 (ANG453), ZD1839, sunitinib (SUTENT™), semaxanib (SU5416), AMG706, AG013736, Imatinib (GLEEVEC™), MLN-518, CEP-701, PKC-412, Lapatinib (GSK572016), VELCADE™, AZD2171, sorafenib (NEXAVAR™), XL880, and CHIR-265. Small molecule protein tyrosine phosphatase inhibitors, such as those disclosed in Jiang et al., *Cancer Metastasis Rev.* 2008; 27:263-72 are also useful for practicing the methods of the invention. Such inhibitors can target, e.g., HSP2, PRL, PTP1B, or Cdc25 phosphatases. Small molecules that target Bcl-2/Bcl-XL, such as those disclosed in US2008/0058322, are also useful for practicing the methods of the present invention. Further exemplary small molecules for use in the present invention are disclosed in Zhang et al. Nature Reviews: Cancer 2009; 9:28-39. In particular, chemotherapeutic agents that lead to immunogenic cell death such as anthracyclins (Kepp et al., *Cancer and Metastasis Reviews* 2011; 30:61-9) will be well suited for synergistic effects with extended-PK IL-2.

It should be understood that the examples listed above are non-limiting, and that the methods of the present invention can be performed in conjunction with any art-recognized small molecule that is effective for treating cancer when used alone or as adjunctive therapy.

Cancer Antigens

In another embodiment, the methods of the invention include administration of an extended-PK IL-2 and a cancer antigen, e.g., for use as a cancer vaccine (see, e.g., Overwijk et al. *Journal of Experimental Medicine* 2008; 198:569-80). Other cancer antigens that can be used in vaccinations include, but are not limited to, (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In another embodiment, the cancer antigen is a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen. It should be understood that the described cancer antigens are only exemplary and that any cancer antigen can be targeted in the present invention.

In another embodiment, the cancer antigen is a mucin-1 protein or peptide (MUC-1) that is found on all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extra-cellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In another embodiment, the cancer antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5):1595-1599).

In one embodiment, the cancer antigen is a human epidermal growth factor receptor-2 (HER-2/neu) antigen. Cancers that have cells that overexpress HER-2/neu are referred to as HER-2/neu$^+$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK™. Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™. Accession No. AAA58637. Based on these sequences, one skilled in the art could develop HER-2/neu antigens using known assays to find appropriate epitopes that generate an effective immune response. Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [$9_{754}$]; and the like.

In one embodiment, the cancer antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR cancers. Exemplary EGFR cancers include lung cancer, head and neck cancer, colon cancer, colorectal cancer, breast cancer, prostate cancer, gastric cancer, ovarian cancer, brain cancer and bladder cancer.

In one embodiment, the cancer antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

In one embodiment the cancer antigen is prostate-specific antigen (PSA) and/or prostate-specific membrane antigen (PSMA) that are prevalently expressed in androgen-independent prostate cancers.

In another embodiment, the cancer antigen is Gp-100 Glycoprotein 100 (gp 100) is a tumor-specific antigen associated with melanoma.

In one embodiment, the cancer antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

In one embodiment, the cancer antigen is carbohydrate antigen 10.9 (CA 19.9). CA 19.9 is an oligosaccharide related to the Lewis A blood group substance and is associated with colorectal cancers.

In another embodiment, the cancer antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In one embodiment, the cancer antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In another embodiment of the invention, the cancer antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

The cancer antigen can be a cell, a protein, a peptide, a fusion protein, DNA encoding a peptide or protein, RNA encoding a peptide or protein, a glycoprotein, a lipoprotein, a phosphoprotein, a carbohydrate, a lipopolysaccharide, a lipid, a chemically linked combination of two or more thereof, a fusion or two or more thereof, or a mixture of two or more thereof. In another embodiment, the cancer antigen is a peptide comprising about 6 to about 24 amino acids; from about 8 to about 20 amino acids; from about 8 to about 12 amino acids; from about 8 to about 10 amino acids; or from about 12 to about 20 amino acids. In one embodiment, the cancer antigen is a peptide having a MHC Class I binding motif or a MHC Class II binding motif. In another embodiment, the cancer antigen comprises a peptide that corresponds to one or more cytotoxic T lymphocyte (CTL) epitopes.

It should be understood that the examples listed above are non-limiting, and that the methods of the present invention can be performed in conjunction with any art-recognized cancer antigen that is known to be effective, e.g., as a cancer vaccine, when used alone or as adjunctive therapy.

Cell Therapy

In yet another embodiment, the methods of the invention include administration of an extended-PK IL-2 and a cell therapy. Cell therapies that are useful for treating cancer are well known and are disclosed in, e.g., U.S. Pat. No. 7,402,431. In a preferred embodiment, the cell therapy is T cell transplant. In a preferred method, T cells are expanded ex vivo with IL-2 prior to transplantation into a subject. Methods for cell therapies are disclosed in, e.g., U.S. Pat. No. 7,402,431, US2006/0057121, U.S. Pat. No. 5,126,132, U.S. Pat. No. 6,255,073, U.S. Pat. No. 5,846,827, U.S. Pat. No. 6,251,385, U.S. Pat. No. 6,194,207, U.S. Pat. No. 5,443,983, U.S. Pat. No. 6,040,177, U.S. Pat. No. 5,766,920, and US2008/0279836.

It should be understood that the examples listed above are non-limiting, and that the methods of the present invention can be performed in conjunction with any art-recognized cell therapy that is effective for treating cancer when used alone or as adjunctive therapy.

Methods of Making Extended-PK IL-2 Proteins

In some aspects, the extended-PK IL-2 proteins of the invention are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Pharmaceutical Compositions and Modes of Administration

In certain embodiments, extended-PK IL-2 is administered together (simultaneously or sequentially) with one or more therapeutic agents, such as a therapeutic antibody. In certain embodiments, extended-PK IL-2 is administered prior to the administration of one or more therapeutic agents, such as a therapeutic antibody. In certain embodiments, extended-PK IL-2 is administered concurrent with the administration of one or more therapeutic agents, such as a therapeutic antibody. In certain embodiments, extended-PK IL-2 is administered subsequent to the administration of one or more therapeutic agents, such as a therapeutic antibody. In certain embodiments, the extended-PK IL-2 and one or more therapeutic agents, such as a therapeutic antibody, are administered simultaneously. In other embodiments, the extended-PK IL-2 and one or more therapeutic agents, such as a therapeutic antibody, are administered sequentially. In yet other embodiments, the extended-PK IL-2 and one or more therapeutic agents, such as a therapeutic antibody, are administered within one, two, or three days of each other.

The one or more therapeutic agents may be those that serve as adjunctive therapy for cancer, such as cytokines, chemotherapeutic agents, small molecules, antigens, or therapeutic antibodies, and are well known in the art and discussed supra. Additional non-limiting examples of additional agents include GM-CSF (expands monocyte and neutrophil population), IL-7 (important for generation and survival of memory T-cells), interferon alpha, tumor necrosis factor alpha, IL-12, and therapeutic antibodies, such as anti-PD-1, anti-PD-L, anti-CTLA4, anti-CD40, anti-OX45, and anti-CD137 antibodies. In some embodiments, the subject receives extended-PK IL-2 and one or more therapeutic agents during a same period of prevention, occurrence of a disorder, and/or period of treatment.

Pharmaceutical compositions of the invention can be administered in combination therapy, i.e., combined with other agents. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for separate pharmaceutical compositions comprising extended-PK IL-2 with a pharmaceutically acceptable diluent, carrier, solubilizer, emulsifier, preservative and/or adjuvant and another pharmaceutical composition comprising one or more therapeutic agents, such as a therapeutic antibody, with a pharmaceutically acceptable diluent, carrier, solubilizer, emulsifier, preservative and/or adjuvant.

In certain embodiments, the invention provides for pharmaceutical compositions comprising extended-PK IL-2 and one or more therapeutic agents, such as a therapeutic antibody, and a therapeutically effective amount of at least one additional therapeutic agent, together with a pharmaceutically acceptable diluent, carrier, solubilizer, emulsifier, preservative and/or adjuvant, and another pharmaceutical composition comprises one or more therapeutic agents, e.g., a therapeutic antibody, together with a pharmaceutically acceptable diluent, carrier, solubilizer, emulsifier, preservative and/or adjuvant. In some embodiments, each of the agents, e.g., extended-PK IL-2, therapeutic antibody, and the additional therapeutic agent can be formulated as separate compositions.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of extended-PK IL-2 and one or more therapeutic agents.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising extended-PK IL-2 and one or more therapeutic antibodies, with or without one or more therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising extended-PK IL-2 and one or more therapeutic antibodies, with or without one or more therapeutic agents, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired extended-PK IL-2 and one or more therapeutic agents, such as a therapeutic antibody, in a pharmaceutically acceptable vehicle. In certain embodiments, a vehicle for parenteral injection is sterile distilled water in which extended-PK IL-2 and one or more therapeutic agents, such as a therapeutic antibody, are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, extended-PK IL-2 and one or more therapeutic agents, such as a therapeutic antibody, can be formulated as a dry powder for inhalation. In certain embodiments, an inhalation solution comprising extended-PK IL-2 and one or more therapeutic agents, such as a therapeutic antibody, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, extended-PK IL-2 and one or more therapeutic agents, such as a therapeutic antibody, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of extended-PK IL-2 and one or more therapeutic agents, such as a therapeutic antibody. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of extended-PK IL-2 and one or more therapeutic agents, such as a therapeutic antibody, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving extended-PK IL-2 and one or more therapeutic agents, such as a therapeutic antibody, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising extended-PK IL-2 and one or more pharmaceutical compositions comprising therapeutic agents, such as a therapeutic antibody, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which extended-PK IL-2 and one or more therapeutic agents such as a therapeutic antibody, are being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 μg/kg to up to about 100 mg/kg or more, depending on the factors mentioned above. In certain embodiments, the dosage can range from 0.1 μg/kg up to about 100 mg/kg; or 1 μg/kg up to about 100 mg/kg; or 5 μg/kg up to about 100 mg/kg.

In certain embodiments, the frequency of dosing will take into account the pharmacokinetic parameters of extended-PK IL-2 and one or more therapeutic agents, such as a therapeutic antibody, in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising extended-PK IL-2 and one or more therapeutic agents, such as a therapeutic antibody in an ex vivo manner. In such instances, cells, tissues and/or organs that have been removed from the patient are exposed to a pharmaceutical composition comprising extended-PK IL-2 and one or more therapeutic agents, such as a therapeutic antibody, after which the cells, tissues and/or organs are subsequently implanted back into the patient.

In certain embodiments, extended-PK IL-2 and one or more therapeutic agents, such as a therapeutic antibody, can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

A kit can include extended-PK IL-2 and one or more therapeutic agents, such as a therapeutic antibody, disclosed herein and instructions for use. The kits may comprise, in a suitable container, extended-PK IL-2 and one or more therapeutic agents, such as a therapeutic antibody, one or more controls, and various buffers, reagents, enzymes and other standard ingredients well known in the art.

The container can include at least one vial, well, test tube, flask, bottle, syringe, or other container means, into extended-PK IL-2 and one or more therapeutic agents, such as a therapeutic antibody, may be placed, and in some instances, suitably aliquoted. Where an additional component is provided, the kit can contain additional containers into which this component may be placed. The kits can also include a means for containing extended-PK IL-2 and one or more therapeutic agents, such as a therapeutic antibody, and any other reagent containers in close confinement for commercial sale. Such containers may include injection or blow-molded plastic containers into which the desired vials are retained. Containers and/or kits can include labeling with instructions for use and/or warnings.

Methods of Treatment

The extended-PK IL-2 and one or more therapeutic agents, such as a therapeutic antibody, and/or nucleic acids expressing them, are useful for treating a disorder associated with abnormal apoptosis or a differentiative process (e.g., cellular proliferative disorders or cellular differentiative disorders, such as cancer). Non-limiting examples of cancers that are amenable to treatment with the methods of the present invention are described below. Extended-PK IL-2, wherein the IL-2 moiety is wild-type IL-2, is the preferred molecule for use in the methods of the invention.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions of the present invention (e.g., extended-PK IL-2 and one or more therapeutic agents, such as a therapeutic antibody and/or the nucleic acid molecules that encode them) can be administered to a patient who has cancer. Extended-PK IL-2 and one or more therapeutic agents, such as a therapeutic antibody, can be used to treat a patient (e.g., a patient who has cancer) prior to, or simultaneously with, the administration of ex vivo expanded T cells.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for each of the extended-PK IL-2 and the one or more therapeutic agents, such as a therapeutic antibody, that are sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

It will be appreciated by those skilled in the art that reference herein to treatment extends to prophylaxis as well as the treatment of the noted cancers and symptoms.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3rd Ed. (Plenum Press) Vols A and B (1992). Moreover, while the examples below employ extended-PK IL-2 of mouse origin, it should be understood that corresponding human extended-PK IL-2 can be readily generated by those of ordinary skill in the art using methods described supra, and used in the methods of the present invention.

Example 1

Materials and Methods

Model of Mouse IL-2/IL-2R Complex

The homology model of the mouse IL-2/IL-2 receptor complex was built using SWISS-MODEL (Schwede et al., Nucleic Acids Research 2003; 31:3381-5), by threading the mouse protein sequences into the crystal structure the human IL-2/IL-2 receptor complex (Wang et al., *Science* 2005; 310:1159-63).

IL-2 Affinity Maturation

A plasmid containing the coding sequence of murine IL-2, pORF-mIL2, was purchased from InvivoGen. The IL-2 coding sequence was amplified by PCR using primers with flanking NheI and BamHI restriction sites and cloned into pCTCON2 by ligation. The resulting plasmid, pCT-mIL2, was transformed into EBY100 using the Frozen-EZ Yeast Transformation II Kit (Zymo Research) according to the manufacturer's instructions. IL-2 display was verified using biotinylated rat anti-HA, clone 3F10, (Roche) and chicken anti-c-myc (Invitrogen). Proper IL-2 folding was confirmed by labeling with His-tagged recombinant mouse IL-2Rα/CD25 (R&D Systems) and rabbit polyclonal anti-6×His tag antibody (Abcam) fluorescently labeled using the Alexa Fluor 647 Monoclonal Antibody Labeling Kit (Invitrogen).

In general, affinity maturation of IL-2 was performed as previously described (Chao et al. *Nat Protocols* 2006 1:755-768; Rao et al., *Mol Pharmacol* 2004; 66:864-9; U.S. Pat. No. 7,569,215; U.S. Pat. No. 7,953,610). Briefly, the IL-2 coding sequence was mutagenized by error-prone PCR under conditions predicted to yield predominantly mutants with one or two amino acid changes per protein. Library inserts and digested pCTCON2 backbone were transformed into competent EBY100 by electroporation. Maximal library diversity was determined by plating serial dilutions of the library immediately after YPD outgrowth onto SD-CAA plates. Plasmids were retrieved from libraries using the Zymoprep Yeast Plasmid Miniprep I Kit (Zymo Research); single clones were obtained after transformation into *E. coli* strain XL1-Blue (Strategene).

FACS screening of libraries 1.0 to 5.2 were conducted at near-equilibrium labeling with soluble CD25 (decreasing from 25 to 1 nM) in PBS with 0.1 wt % BSA. FACS screening of libraries 6.0 and 6.1 were conducted with kinetic competition, using library 5.2 mutants generated by reducing the disulfide bond between Aga1p and Aga2p on the surface of displaying yeast with TCEP.

Selective-reversion mutants of library 6.2 clones were created by site-directed mutagenesis using oligonucleotides (Integrated DNA Technologies) containing the desired mutations.

The equilibrium dissociation constant of any particular clone was determined essentially as described (75). The number of cells and volume per sample were selected to ensure at least 10-fold excess of CD25 relative to yeast-displayed IL-2 or mutant. For picomolar affinity mutants of library 6.2, non-displaying EBY100 cells were spiked in at 90:10 to facilitate pelleting the low numbers of displaying cells. The equilibrium dissociation constant $K_d$ was determined by fitting CD25 concentration and flow cytometry fluorescence data to the monovalent binding isotherm:

$$MFU_{tot}=MFU_{min}+(MFU_{range}\times[CD25])/([CD25]+K_d)$$

where $MFU_{tot}$=total mean fluorescence,

[CD25]=concentration of CD25, and $MFU_{min}$, $MFU_{range}$, and $K_d$ are constants Flow Cytometry DNA encoding IL-2 and QQ 6.2-10 were each subcloned into a pRS316-based secretion plasmid containing the galactose-inducible GAL 1-10 promoter, the engineered secretion leader αpp8 (77), and a C-terminal FLAG tag. Each secretion plasmid was co-transformed with pRS314 into yeast strain YVH10 (78). After growth to mid-log phase ($OD_{600}$~5) at 30° C. in SD-SCAA, protein expression was induced by medium change to SG-SCAA, with BSA as carrier. Cell culture supernatants were harvested 3 days post induction and concentrated by ultrafiltration using Ultracel YM-10 membranes (Millipore). IL-2 and QQ 6.2-10 were purified by immunoaffinity chromatography using anti-FLAG M2 Affinity Gel (Sigma) and size exclusion chromatography using a Superdex 200 column (Amersham Biosciences). Protein purity was verified by silver staining of SDS-PAGE gels using SilverXpress Silver Staining Kit (Invitrogen) and western blotting using anti-FLAG M2 peroxidase conjugate (Sigma-Aldrich). Protein concentrations were determined by quantitative western blotting, using Amino-terminal FLAG-BAP Fusion Protein (Sigma-Aldrich) as standard.

Protein Production and Purification

DNA encoding IL-2 and QQ 6.2-10 were each subcloned into a pRS316-based secretion plasmid containing the galactose-inducible GAL 1-10 promoter, the engineered secretion leader αpp8 (77), and a C-terminal FLAG tag. Each secretion plasmid was co-transformed with pRS314 into yeast strain YVH10 (78). After growth to mid-log phase ($OD_{600}$~5) at 30° C. in SD-SCAA, protein expression was induced by medium change to SG-SCAA, with BSA as carrier. Cell culture supernatants were harvested 3 days post induction and concentrated by ultrafiltration using Ultracel YM-10 membranes (Millipore). IL-2 and QQ 6.2-10 were purified by immunoaffinity chromatography using anti-FLAG M2 Affinity Gel (Sigma) and size exclusion chromatography using a Superdex 200 column (Amersham Biosciences). Protein purity was verified by silver staining of SDS-PAGE gels using SilverXpress Silver Staining Kit (Invitrogen) and western blotting using anti-FLAG M2 peroxidase conjugate (Sigma-Aldrich). Protein concentrations were determined by quantitative western blotting, using Amino-terminal FLAG-BAP Fusion Protein (Sigma-Aldrich) as standard.

Cell Culture

CTLL-2 cells were cultured in RPMI-1640 supplemented with FBS, L-glutamine, penicillin streptomycin (Invitrogen). For maintenance, cells were passaged every other day to 100,000 cells/ml in media supplemented with 100 pM wild-type mouse IL-2 (R&D Systems). For surface persistence and viability assays, cells were passaged to 200,000 cells/ml and cultured in cytokine-free medium for 12 hours prior to pulse with yeast-secreted IL-2 or QQ 6.2-10. Thirty minutes after IL-2 or QQ 6.2-10 addition, cells were pelleted and resuspended in cytokine-free medium. Cell-surface cytokine levels were determined by labeling with M2 mouse anti-FLAG antibody (Sigma-Aldrich). Cell culture viability was determined using the CellTiter-Glo Luminescent Cell Viability Assay (Promega), according to manufacturer's instructions.

Design and Characterization of Non-CD25 Binding IL-2 Mutants

Mutations at amino acid positions 76, 82, and 121 of IL-2 were introduced into pCT-mIL2 by PCR using oligonucleotides (Integrated DNA Technologies) containing the desired mutations. EBY100 yeast harboring each of these clones were grown and induced as described (Chao et al. *Nat Protocols* 2006; 1(2):755-768). CD25 binding capacity was determined by labeling induced yeast with 50 nM soluble murine CD25 (R&D Systems). Proper protein folding was determined by labeling yeast displaying IL-2 variants before and after thermal denaturation with anti-mouse IL-2 antibodies. Yeast displayed IL-2 variants were thermally denatured by incubating induced yeast at 85° C. for 30 minutes. Anti-mouse IL-2 antibodies used were S4B6 (gift of Jianzhu Chen Lab, MIT), JES6-1A12, and JES6-5H4 (eBioscience).

Antibody binding both before and after thermal denaturation of IL-2 mutant indicates antibody is non-conformation specific (JES6-1A12). Loss of antibody binding after thermal denaturation indicates antibody is conformation-specific (S4B6 and JES6-5H4). IL-2 variants E76A and E76G were detected by S4B6 before but not after thermal denaturation, suggesting they are properly folded proteins that lack CD25 binding capacity. Proper folding of E76A and E76G is further validated by their stimulation of CTLL-2 growth in vitro as well as E76G's stimulation CD8+ T cell and NK cell expansion in vivo.

Pharmacokinetics

Fc/IL-2 fusions were labeled with IRDye 800CW (LI-COR Biosciences) according to manufacturer's instructions. Unreacted dye was removed using Zeba desalting columns (Thermo Scientific). Labeled proteins, 50 μg in 100 μl PBS per dose, were administered intravenously by retro-orbital injection. At time=0, 0.5, 1, 3, 5, 8, 24, 48, and 96 hours after injection, blood samples were collected from the tip of the tail into heparin-coated capillary tubes (VWR International). Samples were stored at 4° C., protected from light, until analysis.

On day of analysis, blood samples were centrifuged (15 min at 12000 rpm at 4° C.) to remove cellular components. The plasma was transferred to fresh capillary tubes and scanned using an Odyssey Infrared Imaging System (L1-COR Biosciences). Signal was acquired in the 800 nm channel, which corresponds to serum levels of Fc/IL-2 fusions. Using the image processing program ImageJ (US National Institutes of Health), each sample was approximated as a line of width 2 and the mean intensity along was line was determined. The mean fluorescence intensities were then fit to a biexponential:

$$\mathrm{MFI}(t)=Ae^{-\alpha t}+Be^{-\beta t}$$

where MFI=mean fluorescence intensity, t=time, and

A, α, B, and β are constants

Fc/IL-2 fusion proteins were administered intravenously by retro-orbital injection. Four days post injection, animals were euthanized by CO2 asphyxiation. Animals were weighted on a scale.

Pulmonary Wet Weight

Lungs from mice injected with Fc/IL-2 fusions were extracted and placed into scintillation vials. Samples were weighed, frozen in liquid nitrogen, and lyophilized for 48 hours at room temperature under vacuum. Pulmonary wet weight was calculated by subtracting the sample weight after lyophilization from the initial sample weight.

Flow Cytometry

Single-cell suspensions of spleen were prepared by rubbing spleens between two frosted microscope slides. Red blood cells were lysed with ammonium chloride and passed through mesh filters to remove hair and debris. Antibodies against CD3, CD4, CD8, CD25, NK1.1, Foxp3, CellTrace Calcein Violet (Invitrogen) were used.

Samples were analyzed using a LSR II flow cytometer using FACS Diva software (BD Biosciences). Flow cytometry data was analyzed using FlowJo software (Tree Star, Inc.). Total cell number per spleen was calculated based on number of cells processed by cytometer and fraction of splenocyte suspension analyzed.

Histology

Kidneys, livers, lungs, and spleens were fixed in 10% formalin overnight, embedded in paraffin, sectioned at 6 μm, and stained with hematoxylin and eosin. Tumors were cut in half: one half was fixed and stained as organs above; the other was embedded in O.C.T. media, and frozen in isopentane in liquid nitrogen, and sectioned at 6 μm.

Example 2

Generation of High Affinity CD25-Binding IL-2 Mutants

Mouse IL-2 was affinity matured with error-prone PCR and yeast surface display to obtain high affinity CD25-binding IL-2 mutants. The mutagenesis approach and affinity maturation progress was determined by referencing a model of the mouse IL-2/IL-2R complex based on the crystal structure of the human IL-2/IL-2R complex. Error-prone PCR conditions (nucleotide analogue concentration and amplification cycle number) were chosen such as to produce one to two amino acid mutations per gene, distributed throughout the entire IL-2 gene.

A yeast surface display library was labeled with soluble CD25 and screened six times for higher affinity clones by FACS. Sequences from a selection of clones indicated accumulation of mutants that encode proline or threonine at position 126, which is serine in wild-type mouse IL-2. Notably, position 126 is proline or threonine in many other animal species. According to the model of the IL-2/IL-2 receptor complex, this position locates to the interface with CD25. Further affinity maturation of S126P and S126T IL-2, which bound to CD25 with an affinity 2 to 3-fold higher than wild-type IL-2, led to the generation of IL-2 mutants with 500-fold affinity improvement over wild-type IL-2. When these mutants were sequenced, their mutations were found to locate to two difference faces of IL-2, that in potential contact with CD25 and that in potential contact with IL-2Rβ.

To avoid disrupting the interaction with IL-2Rβ, putative IL-2Rβ-binding mutations were mutated so as to revert the mutations back to the wild-type amino acid residues by site-directed mutagenesis. The mutants and their sequences are shown in FIG. 1. These reversion mutants retained high CD25 binding affinity (FIG. 2). For convenience, high-affinity CD25-binding QQ 6.2-10 ("QQ6210") was used in further experiments.

Example 3

Generation of a Non-CD25-Binding IL-2 Mutant

Figure 3:
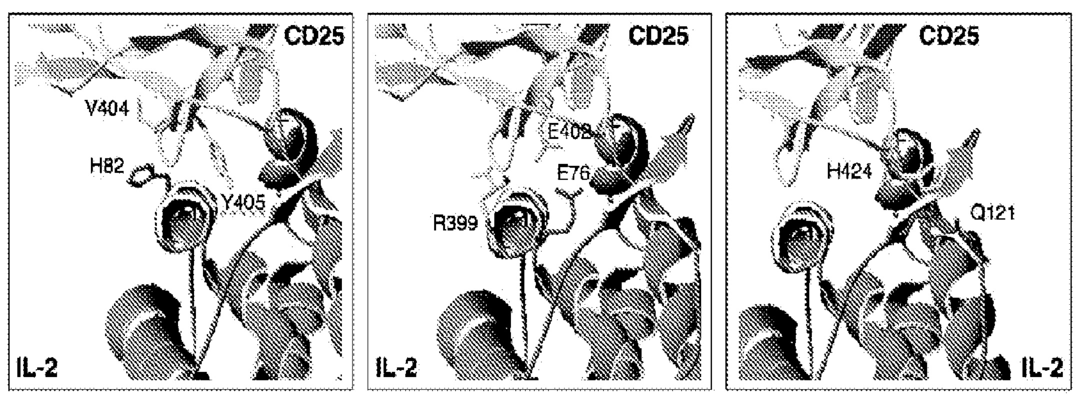
FIG. 3 is a three dimensional model of murine IL-2 bound to murine CD25 generated using SWISS-MODEL (Schwede et al., *Nucleic Acids Research* 2003; 31:3381-5). Residues E76, H82, and Q121 are in close contact with CD25.

Inspection of the mouse IL-2/IL-2 receptor complex revealed three amino acid residues in intimate contact with CD25: E76, H82, and Q121 (FIG. 3). To disrupt CD25 binding, each of these residues was mutated to one of four alternative amino acids that differ from the wild-type in size, hydrophobicity, or charge. These 12 mutants were displayed on the surface of yeast and tested for CD25 binding by labeling with 5 or 50 nM soluble CD25.

TABLE 1

| Mutations |
|---|
| E76 --> R, F, A, G |
| H82 --> E, S, A, G |
| Q121 --> R, S, A, G |

Figure 4:
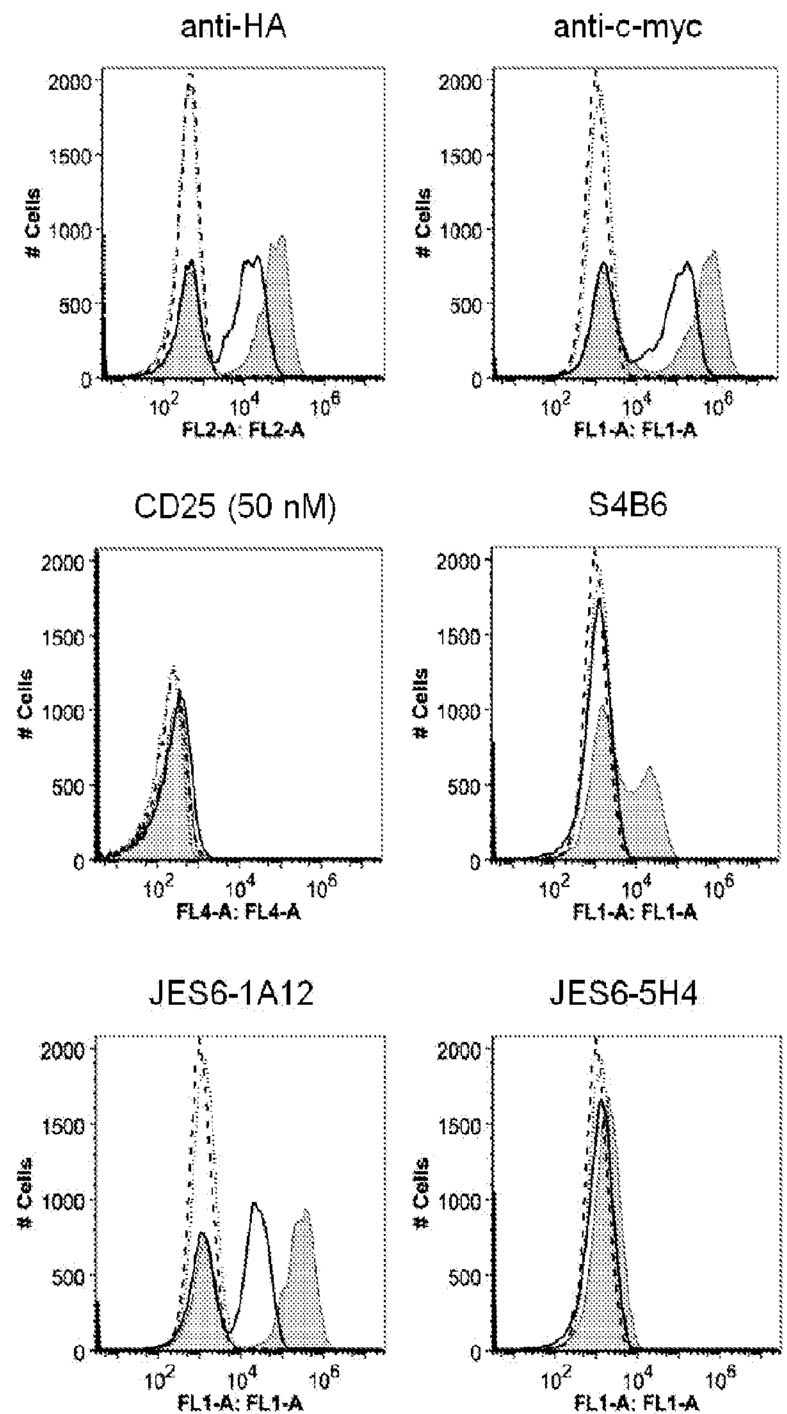
FIG. 4 is a series of flow cytometry histograms showing the display of E76A IL-2 on the surface of yeast (as determined by anti-HA and anti-c-myc staining), its lack of detectable binding to soluble murine CD25 at 50 nM, and its proper folding (as detected by anti-IL-2 antibodies S4B6, JES6-1A12, and JESA-5H4 before and after thermal denaturation).

While all H82 and Q121 mutants retained CD25 binding, no CD25 binding was detected for E76 mutants (FIG. 4). Labeling of E76 mutants with conformation-specific anti-mouse IL-2 antibodies, with or without thermal denaturation, suggested that E76A and E76G are well-folded proteins with no detectable binding at 50 nM soluble CD25 (FIG. 4).

Example 4

Fc/IL-2 and Mutants

A vector encoding the heavy chain of a mouse IgG2a from C57BL/6 mice was provided by J. Ravetch (The Rockefeller University). A fragment encoding the hinge, $C_H2$, and $C_H3$ domains was cloned into the gWIZ vector (Genlantis) from PstI to SalI sites. Mouse IL-2 with a 6×His tag was subsequently cloned into the vector C-terminal to Fc. To enable expression of monovalent Fc/IL-2, a vector encoding the Fc with a FLAG tag was also constructed. Notably, a D265A mutation was introduced into the Fc coding sequence to reduce effector function (i.e., to reduce ADCC and CDC) as disclosed in Baudino et al. (*J Immunol* 2008; 181:6664-9). DNA sequences were confirmed by DNA sequencing. Plasmid DNA was transformed into XL1-Blue for amplification. DNA was purified from cells using PureLink HiPure Maxiprep Kit (Invitrogen) and sterile filtered.

HEK293 cells (Invitrogen) were cultured according to manufacturer's instructions. gWIZ vectors encoding D265A Fc fused with IL-2 (nucleic acid sequence: SEQ ID NO: 11; amino acid sequence: SEQ ID NO: 12), QQ6210 (nucleic acid sequence: SEQ ID NO: 13; amino acid sequence: SEQ ID NO: 14), E76A IL-2 (nucleic acid sequence: SEQ ID NO: 15; amino acid sequence: SEQ ID NO: 16), or E76G IL-2 (nucleic acid sequence: SEQ ID NO: 17; amino acid sequence: SEQ ID NO: 18) were co-transfected with gWIZ D265A Fc FLAG, encoding D265AFc/flag (nucleic acid sequence: SEQ ID NO: 9; amino acid sequence: SEQ ID NO: 10), into HEK293 cells using PEI in FreeStyle 293 media supplemented with OptiPro (Invitrogen). Seven days post transfection, culture supernatants were harvested by centrifugation (30 min at 15,000×g, 4° C.) and the supernatant sterilized by filtration through 0.22 μm filters.

Monovalent Fc/IL-2 fusions were purified by sequential TALON His-tag metal affinity purification (Clontech) and anti-FLAG affinity chromatography (Sigma-Aldrich) following manufacturer's instructions. Elution fractions were concentrated using 15-ml 30-kDa Amicon Ultra Centrifugal Devices (Millipore) and buffered exchanged into PBS. Protein concentration was determined by the Beer-Lambert Law:

$$A=\epsilon lc,$$

where A=absorbance at 280 nm,

ε=extinction coefficient, l=path length, and c=concentration

Absorbance at 280 nm was measured using a NanoDrop 2000c (Thermo Scientific). The molecular weights and extinction coefficients of Fc/IL-2 fusion proteins were estimated from their amino acid sequences. Fc/IL-2 fusions were secreted using HEK293 cells and purified by sequential TALON resin and anti-FLAG affinity chromatography.

Figure 5:
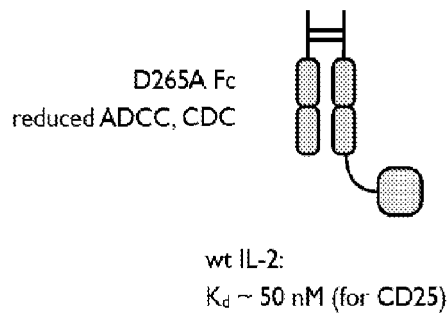
FIG. 5 is a schematic of D265AFc/IL-2 (hereafter referred to as "Fc/IL-2"). IL-2 is monovalent and has a $K_D$ of about 50 nM for mouse CD25. The beta half-life of Fc/IL-2 is about 15 hours.

All Fc/IL-2 fusions used in the Examples described infra all have the D265A mutation in the Fc moiety (to reduce effector function, i.e., ADCC and CDC) and are in monovalent form (to separate any effects observed from that caused by IL-2 bivalency) (FIG. 5). Fc/IL-2 fusions need not be limited to the monovalent form, but can also be used in the bivalent form. The beta half-life of Fc/IL-2 is approximately 15 hours.

Example 5

Effects of Fc/IL-2 Fusions on Cell Proliferation of a Cytotoxic T Cell Line

To determine the effects of CD25 binding affinity on cell proliferation, the effects of an affinity series of mouse IL-2, consisting of Fc-fused high-affinity CD25-binding QQ 6.2-10 ("Fc/QQ6210"), wild-type IL-2 ("Fc/IL-2"), and a non-CD25 binding IL-2 mutant named E76G ("Fc/E76G") were tested for the ability to stimulate cell proliferation. As described supra, these three Fc/IL-2 fusions have the D265A mutation in the Fc moiety.

| Protein | Extinction coefficient, $\epsilon$ ($M^{-1}$ $cm^{-1}$) | Molecular weight (g/mol) |
|---|---|---|
| Fc/IL-2 | 69870 | 72514.5 |
| Fc/QQ6210 | 68380 | 72592.4 |
| Fc/E76G | 69870 | 72442.4 |

Figure 6:
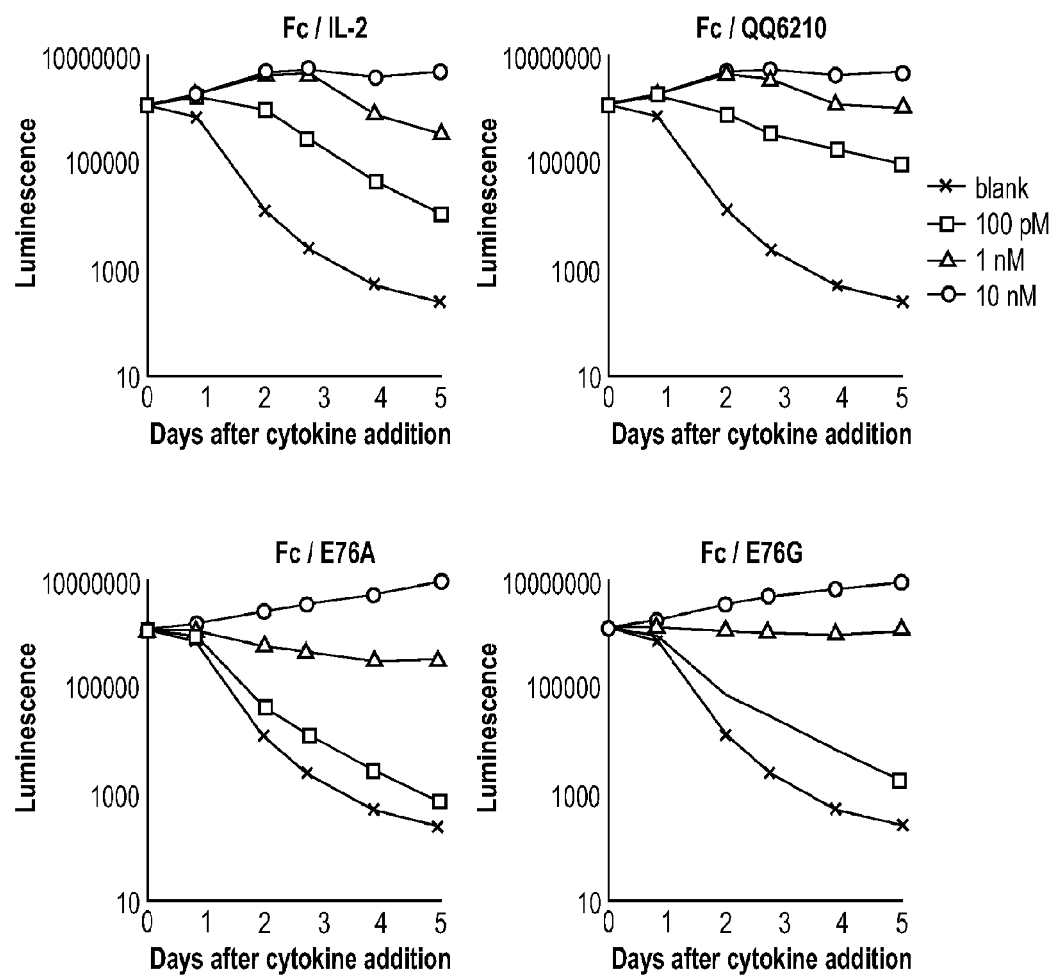
FIG. 6 is a series of graphs depicting the viability of CTLL-2 cells stimulated with the indicated Fc/IL-2 and mutants. CTLL-2 cells were stimulated with Fc/IL-2, Fc/QQ6210, Fc/E76A, or Fc/E76G for 30 minutes, then resuspended in cytokine-free medium. At indicated times after cytokine withdrawal, culture aliquots were used to measure culture viability as determined by cellular ATP content, which was assayed through stimulation of ATP-dependent luciferase activity using the CellTiter-Glo Luminescent Viability Assay (Promega).

To verify that Fc/IL-2, Fc/QQ6210, Fc/E76A, and Fc/E76G were functional, they were assayed for their ability to stimulate the growth of CTLL-2 cells, a murine cytotoxic T cell line. Under static conditions, all Fc/IL-2 proteins support CTLL-2 growth at 100 pM, 1 nM, and 10 nM (FIG. 6). The different growth kinetics resulting from stimulation with Fc/E76A and Fc/E76G likely reflects the lack of CD25 binding. For convenience, Fc/E76G was selected for further characterization in vivo.

Example 6

Fc/IL-2 Fusions Thereof Exhibit Extended Circulation Half-Life In Vivo

IL-2 has a very short systemic half-life, with an initial clearance phase with an alpha half-life of 12.9 min followed by a slower phase with a beta half-life of 85 min (Konrad et al., *Cancer Res* 1990; 50:2009-17). Thus, one of the difficulties associated with IL-2 therapy is the maintenance of therapeutic concentrations of IL-2 (1-100 pM) for a sustained period. To this end, the in vivo circulation half-lives of Fc/IL-2, Fc/QQ6210, and Fc/E76G were determined.

Each Fc/IL-2 fusion was labeled with IRDye 800 and injected intravenously into C57BL/6 mice as a 50 μg bolus. Blood samples were collected over four days. Serum levels of Fc/IL-2 fusions, as determined by the 800 nm signal within blood samples, was fitted to the biexponential decay equation $MFI(t)=Ae^{-\alpha t}+Be^{-\beta t}$, where MFI is the mean fluorescence intensity of the blood sample, t is time, and A, B, $\alpha$, and $\beta$ are pharmacokinetic parameters to be fitted. As shown in Table 2, all Fc/IL-2 fusions exhibit substantially prolonged in vivo persistence compared to non-Fc fused IL-2.

TABLE 2

| Protein | A | B | $\alpha$ ($hr^{-1}$) | $\beta$ ($hr^{-1}$) | $t_{1/2,\alpha}$ (hr) | $t_{1/2,\beta}$ (hr) |
|---|---|---|---|---|---|---|
| Fc/IL-2 | 0.50 ± 0.15 | 0.70 ± 0.53 | 0.12 ± 0.08 | 0.05 ± 0.01 | 1.9 ± 0.9 | 16.4 ± 3.6 |
| Fc/QQ6210 | 0.44 ± 0.11 | 0.07 ± 0.02 | 0.19 ± 0.01 | 0.02 ± 0.00 | 3.6 ± 0.2 | 34.3 ± 3.2 |
| Fc/E76G | 0.71 ± 0.05 | 0.16 ± 0.02 | 0.25 ± 0.06 | 0.03 ± 0.00 | 3.0 ± 0.7 | 25.4 ± 1.8 |

Example 7

Fc/IL-2 and Mutants Induce Splenomegaly and Alter T Cell and NK Cell Composition To determine the effects of Fc/IL-2, Fc/QQ6210, and Fc/E76G on T cell and NK cell composition in vivo, C57BL/6 mice were injected intravenously once with 5 or 25 μg Fc/IL-2, Fc/QQ6210, or Fc/E76G. Four days later, spleens were photographed and splenocytes analyzed for T and NK cell composition by FACS.

Figure 7:
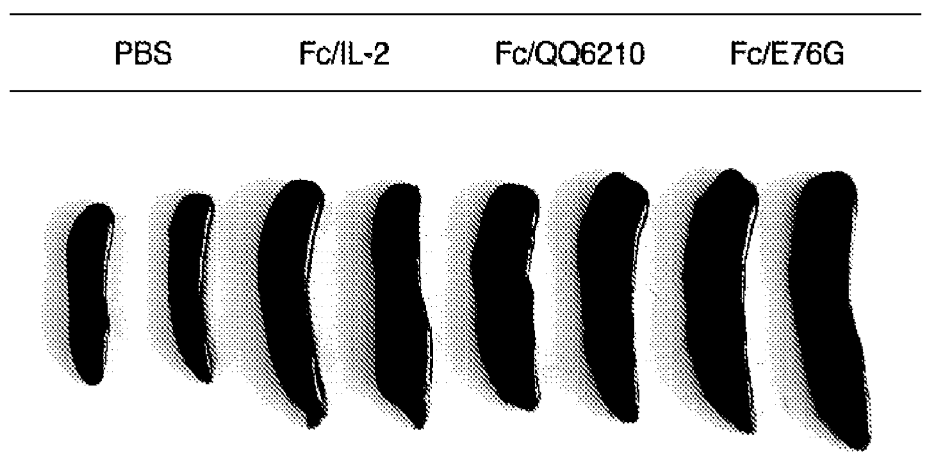
FIG. 7 is a photograph of spleens isolated from C57BL/6 mice (n=3/group) injected intravenously with PBS or 25 μg Fc/IL-2, Fc/QQ6210, or Fc/E76G. Spleens were isolated 4 days after treatment. Two representative spleens per group are shown.
Figure 8:
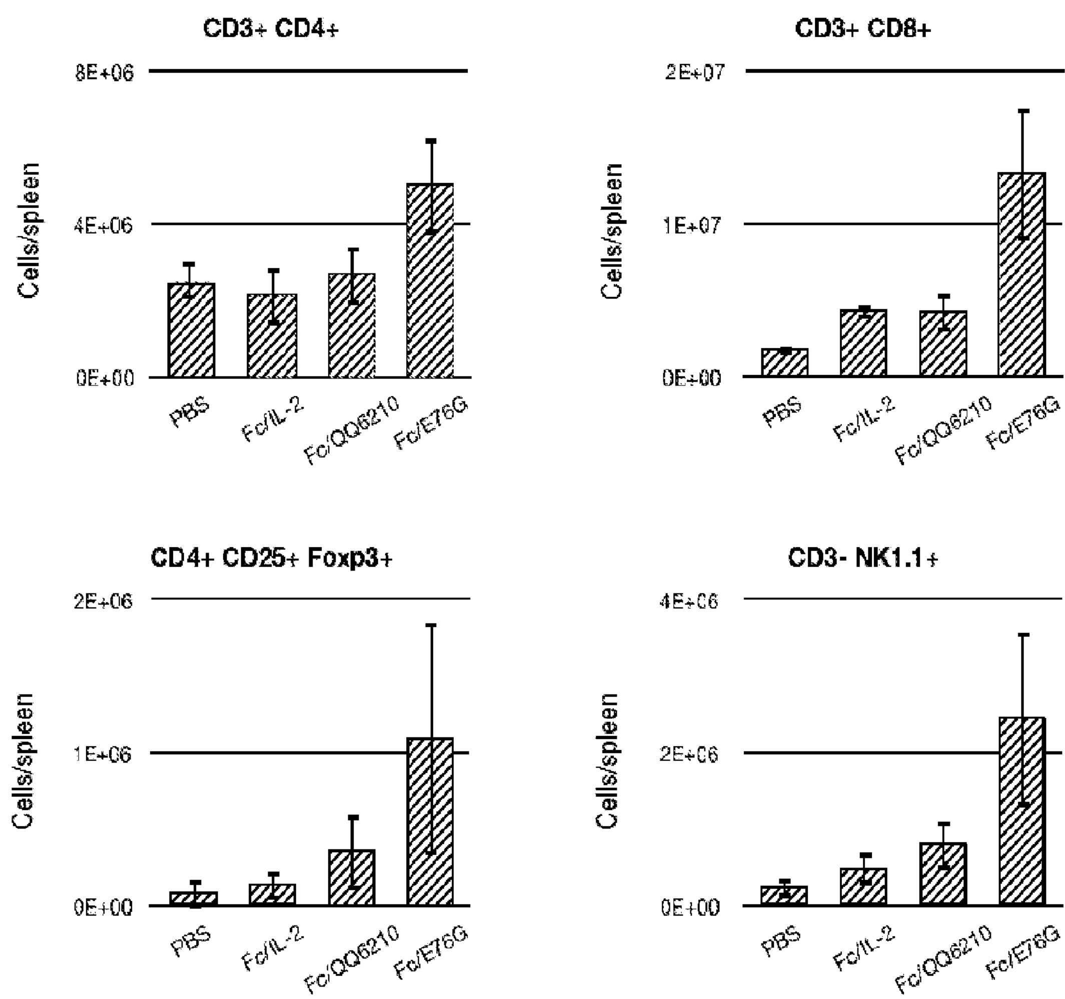
FIG. 8 is a series of graphs depicting various lymphocyte populations in spleens isolated from mice treated under the conditions described in FIG. 7. Populations of cell types are as indicated. CD3+CD8+ depicts CD8+ T cells, and CD3− NK1.1+ depicts natural killer (NK) cells. Error bars represent standard deviation for measurements of three samples.

Both doses of Fc/IL-2 fusions increased spleen size compared to PBS-treated controls (FIG. 7). With respect to CD8+ T cell and NK cell composition, Fc/IL-2 and Fc/QQ6210 expanded CD8+ T cell and NK cells approximately 2-fold, while Fc/E76G expanded these populations up to 5-fold compared to PBS-treated controls (FIG. 8). The notable expansion of CD8+ T and NK cells by Fc/E76G validates the functional signaling of this mutant through IL-2R$\beta$ and $\gamma_c$.

Example 8

Toxicity of Fc/IL-2 Fusions

Total animal weight was used as a proxy for toxicity, and lung wet weight was used as an indicator for pulmonary edema and vascular leak syndrome, which are often associated with IL-2 therapy.

Figure 9:
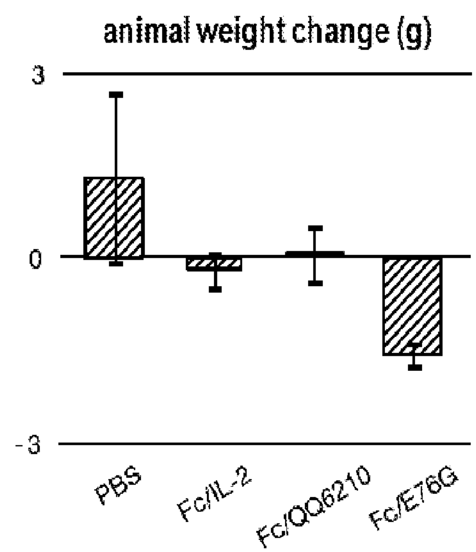
FIG. 9 is a graph depicting total weight change (grams), which is used as a proxy for toxicity, in C57BL/6 mice injected with PBS, Fc/IL-2, Fc/QQ6210, or Fc/E76G as described in FIG. 7.

As shown in FIG. 9, Fc/IL-2 and Fc/QQ6210 were well tolerated at the two doses tested (5 μg and 25 μg), whereas Fc/E76G was highly toxic at 25 μg, likely because it strongly promoted CD8+ T cell and NK cell growth as described in Example 7. Fc/E76G was well tolerated at the lower dose of 5 μg.

Figure 10:
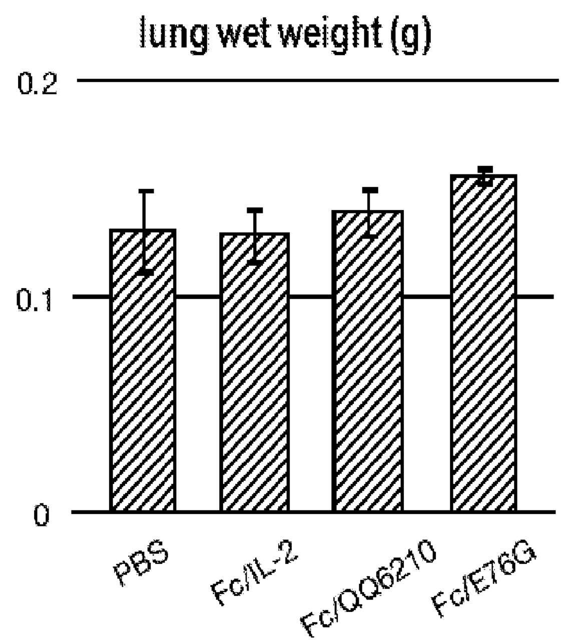
FIG. 10 is a graph depicting total lung wet weight (grams), which is used as an indicator of pulmonary edema and vascular leak syndrome. C57BL/6 mice injected with PBS, Fc/IL-2, Fc/QQ6210, or Fc/E76G as described in FIG. 7.

Fc/IL-2 fusions did not significantly affect pulmonary wet weight compared to PBS-treated controls (FIG. 10). In contrast to a previous study by Krieg et al. (*PNAS* 2010; 107:11906-11), CD25 binding did not drive IL-2 toxicity in the lung, as demonstrated by the similar wet lung wet weight of mice injected with all three Fc/IL-2 fusions and the PBS control.

Example 9

Synergistic Tumor Control by Fc/IL-2 Fusions and a Therapeutic Antibody in Melanoma While a number of reports on combination therapy with IL-2 and therapeutic antibodies in the treatment of cancer exist, the results have been largely unsuccessful, with most studies reporting no or limited clinical benefit (Mani et al., *Breast cancer research and treatment* 2009; 117; 83-9; Khan et al. Clinical Cancer Research 2006; 12:7046-53). To determine whether the limited effects of previous combination therapies could be overcome by increasing the serum half-life of IL-2, Fc/IL-2 fusions, in combination with a therapeutic antibody, were tested for the ability to reduce the size of established tumors. To this end, an art-recognized highly aggressive mouse model of melanoma (i.e., B16 murine melanoma) was used. This model was derived from a spontaneous tumor in a C57BL/6 mouse. B16 melanoma is poorly immunogenic, with no MHC class II expression and very low expression levels of MHC class I. Moreover, the sub-line B16-F10 has been specifically selected for high metastatic potential.

The mouse melanoma cell line B16-F10 was a gift of Darrell J. Irvine (MIT). Cells were cultured in DMEM supplemented with FBS, L-glutamine, and pen-strep at 37° C. with 5% $CO_2$. At approximately 70% confluency, cells were lifted off of plates using 0.035% trypsin and EDTA. Digestion was quenched with media and the cells pelleted by centrifugation at 1000 rpm. For passaging, cells were resuspended in media to $10^6$ cells per 10 ml. For tumor inoculation, cells were resuspended in PBS to $10^6$ cells per 50 μl. Cells were verified to be mycoplasma-free by PCR amplification and staining with antibody TA99. C57BL/6 mice (The Jackson Laboratory) were used at 8 to 10 weeks of age.

On the day of tumor inoculation, mice were anesthetized with isoflurane and patches of fur were shaved from the left or right flanks to expose skin. $1\times10^6$ cells in 50 μl PBS were injected subcutaneously using a 27G1/2 syringe and needle. Every other day following tumor inoculation, mice were weighed and their tumors measured using digital calipers. Tumor volumes were calculated using the modified ellipsoid volume formula:

$$\text{tumor volume}=\tfrac{1}{2} l\, w^2,$$

wherein l=longest dimension of tumor, and w=longest dimension of tumor perpendicular to l.

Given the documented toxicity of IL-2 therapy, dosing regimens were optimized for the Fc/IL-2 fusions. Therapy was initiated at the time of tumor inoculation ("early treatment") or six days after tumor inoculation, when tumor nodules were visible and palpable ("late treatment"). 50 μg of Fc/IL-2 fusions per dose, which had previously been found to be tolerable in single-dose pharmacokinetics studies, were administered, with subsequent doses administered every 3 days. Under this treatment regimen, Fc/IL-2 was lethal upon the fourth or third dose, for early and late treatment, respectively; Fc/QQ6210 was well-tolerated; while Fc/E76G was extremely toxic, being lethal upon the second dose for both therapy initiation times. Toxicity was reduced when Fc/IL-2 fusions were administered at 25 μg once a week. At this dose, Fc/IL-2 fusions were well tolerated. The results of these toxicity studies, and the resulting dosing regimen, is analogous to similar experiments reported previously with PEG-IL-2 (Zimmerman et al., Cancer Research 1989; 49:6521-8).

Antibody TA99 was used as the therapeutic antibody for the combination therapy. TA99 is a murine IgG2a antibody that recognizes the melanosome antigen tyrosinase-related protein-1 (Tyrp-1) and is of identical specificity as an antibody originally isolated from the serum of a melanoma patient (Houghton et al., *Prog Clin Biol Res* 1983; 119:199-205). Tolerable and effective dosing regiments were also determined for Fc/IL-2 fusions in combination with 100 μg antibody TA99. As described above, 25 μg Fc/E76G with TA99 once every three days was lethal upon the second dose, while reducing the frequency to once weekly was well-tolerated.

Having established a tolerable dosing regimen for Fc/IL-2 fusions with TA99, the efficacy of Fc/IL-2 fusions alone or in combination with TA99 were tested for controlling subcutaneous B16-F10 tumors. C57BL/6 mice (n=5/group) were injected subcutaneously with B16-F10 melanoma cells and tumors were allowed to establish for six days. With tumor nodules visible and palpable, mice were treated with 25 μg Fc/IL-2 or 25 μg Fc/IL-2 in combination with 100 μg TA99, with subsequent doses administered every six days. As controls, B16-F10 tumor-bearing mice were treated with PBS, 6 μg free IL-2 (this corresponds to a stoichiometrically equivalent amount to each of the Fc/IL-2 fusions used), 100 μg TA99, or 6 μg free IL-2 with 100 μg TA99.

Figure 11:
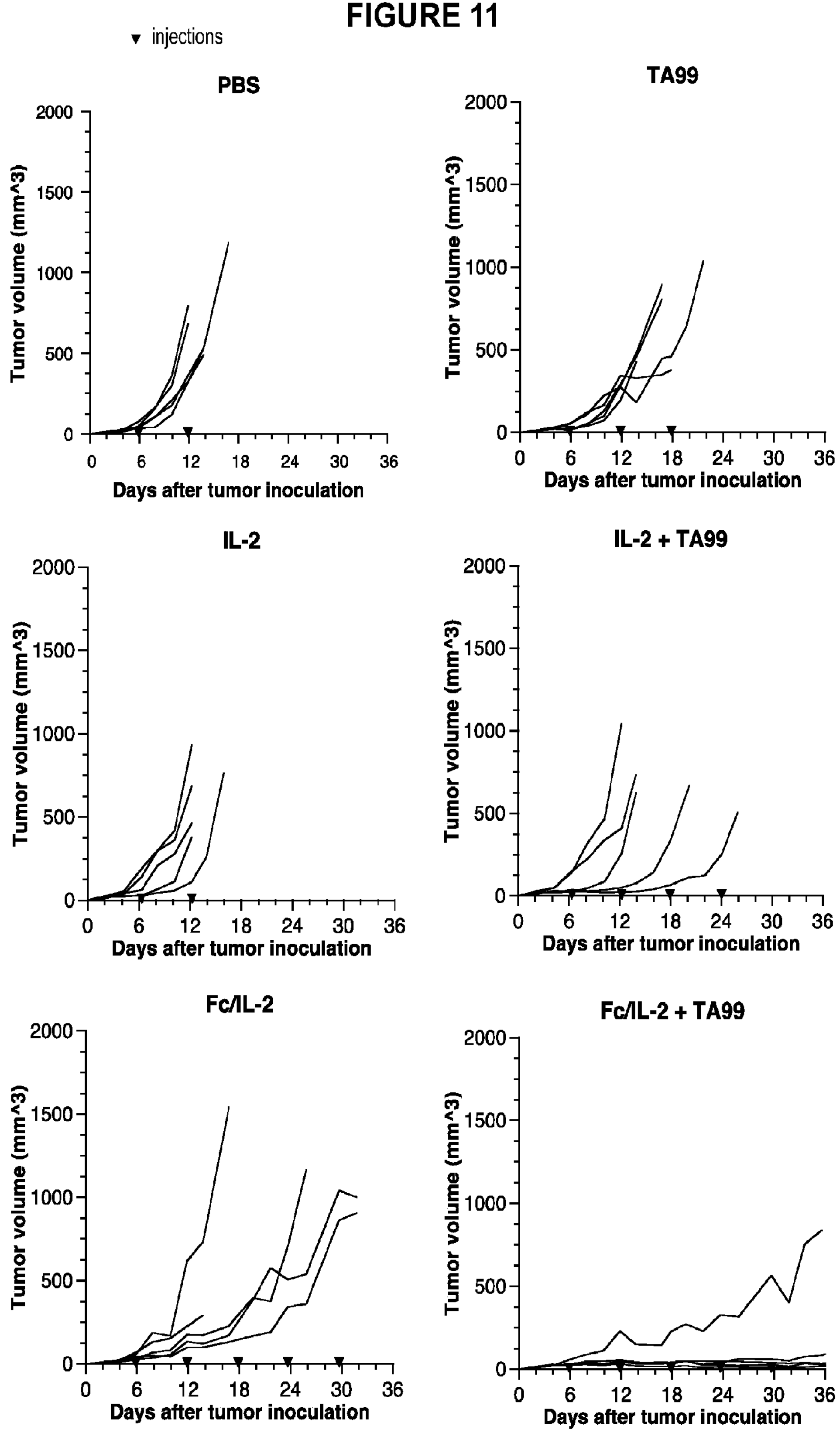
FIG. 11 is a series of graphs depicting the anti-tumor effects of Fc/IL-2 and TA99 antibody. C57BL/6 mice (n=5/group) were injected subcutaneously with $10^6$ B16-F10 melanoma cells. Six days after tumor inoculation mice were injected intravenously with PBS, 6 μg IL-2, 25 μg Fc/IL-2, 100 μg TA99, IL-2 (6 μg)+TA99 (100 μg), or Fc/IL-2 (25 μg)+TA99 (100 μg). Subsequent doses were administered every 6 days. Each individual line represents one mouse and inverted triangles represent an injection of the indicated regimen.
Figure 12:
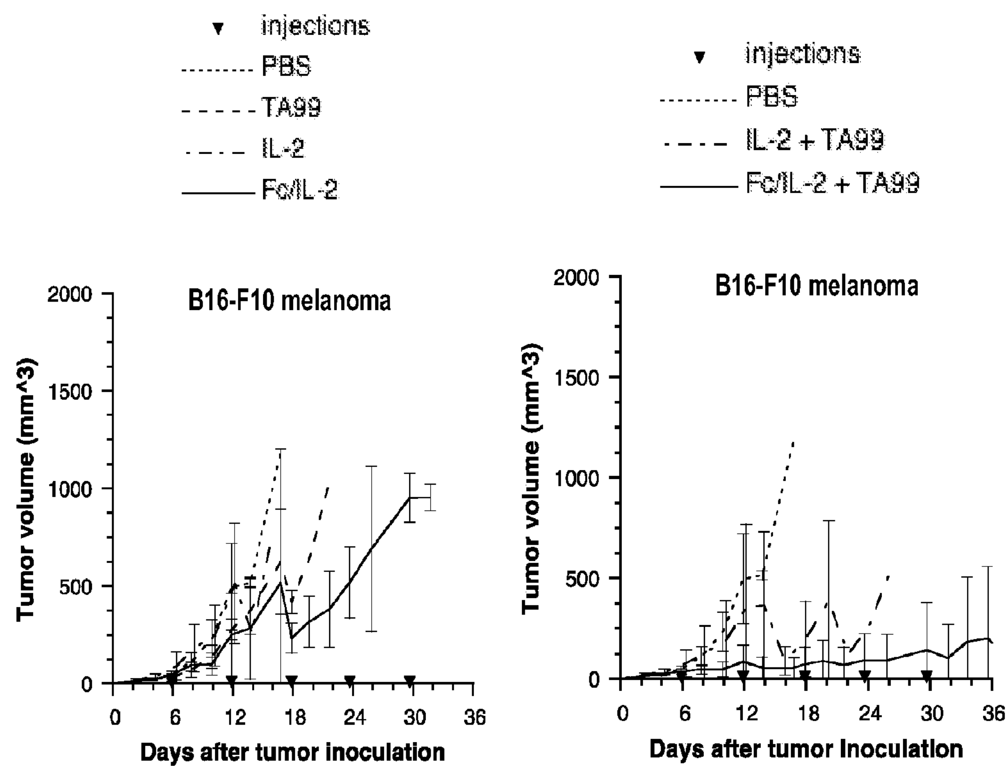
FIG. 12 is a series of graphs depicting the average tumor volume of each treatment group shown in FIG. 11. Bars represent standard deviation.

As expected for B16-F10 tumors, all PBS-treated mice required euthanasia due to tumor size within two weeks of tumor inoculation. Consistent with previous reports, IL-2 or TA99 alone was insufficient to delay B16-F10 growth (FIG. 11). IL-2 in combination with TA99 delayed tumor progression to a limited degree in some mice (FIG. 11). However, all tumors in mice treated with IL-2 and TA99 reached euthanasia criteria within the course of therapy. Fc/IL-2 alone, by contrast, significantly reduced tumor burden, and Fc/IL-2 in combination with TA99 exerted synergistic tumor control, as evidenced by the complete lack of tumor growth in 4 of 5 mice over the course of 30 days (FIG. 11). Relative to PBS-treated controls, a single dose of Fc/IL-2 reduced average tumor volume on day 12 by 50%; a single treatment with Fc/IL-2 in combination with TA99 reduced average tumor volume on day 12 by 83%. Continuing therapy with Fc/IL-2 delayed tumors from reaching a volume of 500 $mm^3$ by 7 days. For Fc/IL-2 and TA99 combination therapy, four of five tumors remained below 85 $mm^3$ during treatment. Only one of five tumors progressed to reach 500 $mm^3$, although growth was significantly delayed by 16.7 days relative to PBS-treated controls. This series of treatments was also plotted as average tumor volumes for each group with standard deviations (FIG. 12). These data confirm the limited efficacy of IL-2 and TA99 alone compared to Fc/IL2 alone, and confirm the synergistic effect conferred by the Fc/IL-2+TA99 group compared to Fc/IL or TA99 alone, and the marked survival benefit conferred by the Fc/IL-2 and TA99 combination therapy over IL-2 and TA99 combination therapy. Statistics are shown below.

TABLE 3

P values for Fc/IL-2 + TA99 treatment vs. indicated groups at different days after tumor inoculation (unpaired t-test using data from FIG. 12)

| Days after turmor inoculation | PBS | IL-2 | Fc/IL-2 | TA99 | IL-2 + TA99 |
|---|---|---|---|---|---|
| 10 | 0.0038 | 0.0243 | 0.1190 | 0.0204 | 0.1588 |
| 12 | 0.0047 | 0.0174 | 0.1387 | 0.0023 | 0.1879 |
| 14 | | | 0.1414 | | 0.0702 |

TABLE 3-continued

P values for Fc/IL-2 + TA99 treatment vs. indicated groups at different days after tumor inoculation (unpaired t-test using data from FIG. 12)

| Days after turmor inoculation | PBS | IL-2 | Fc/IL-2 | TA99 | IL-2 + TA99 |
|---|---|---|---|---|---|
| 17 | | | 0.1678 | | 0.0407 |
| 18 | | | 0.0385 | | |

Figure 13:
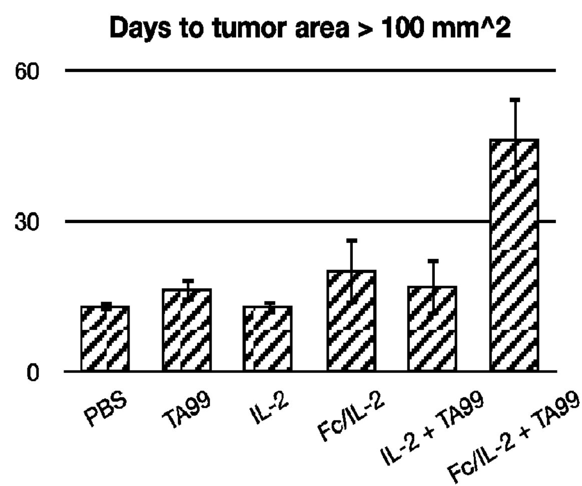
FIG. 13 is a graph depicting the number of days it took for tumors in each treatment group shown in FIG. 11 to reach an area >100 $mm^2$. Tumor area was calculated as l×w, wherein l=longest dimension of the tumor and w=longest dimension perpendicular to 1.

The synergistic control of Fc/IL-2 in combination with TA99 was further demonstrated when the data were plotted as the number of days it took for tumor area to become >100 $mm^2$. Euthanasia criteria was tumor area >100 $mm^2$, and tumor area was calculated as l×w, wherein l=longest dimension of the tumor and w=longest dimension perpendicular to 1. As shown in FIG. 13, while Fc/IL-2 treated mice took somewhat longer to achieve a tumor area >100 $mm^2$ than PBS-treated controls, IL-2, TA99, and IL2+TA99 groups, the duration required for tumors in the Fc/IL-2+TA99 group to achieve a tumor area >100 $mm^2$ was more than double that of any of the other groups (n=5 mice/group) (Table 4).

TABLE 4

Average number of days (±standard deviation) to tumor area >100 $mm^2$

| PBS | Fc/IL-2 | TA99 | FC/IL-2 + TA99 | IL-2 | IL-2 + TA99 |
|---|---|---|---|---|---|
| 13.00 ± 0.92 | 20.13 ± 6.56 | 16.35 ± 2.31 | 46.18 ± 8.61 | 12.94 ± 1.50 | 16.83 ± 5.58 |

These data further support the synergistic tumor controlling effect exerted by Fc/IL-2 and TA99 combination therapy, as well as the synergistic effect of the combination therapy on prolonging survival.

Figure 14:
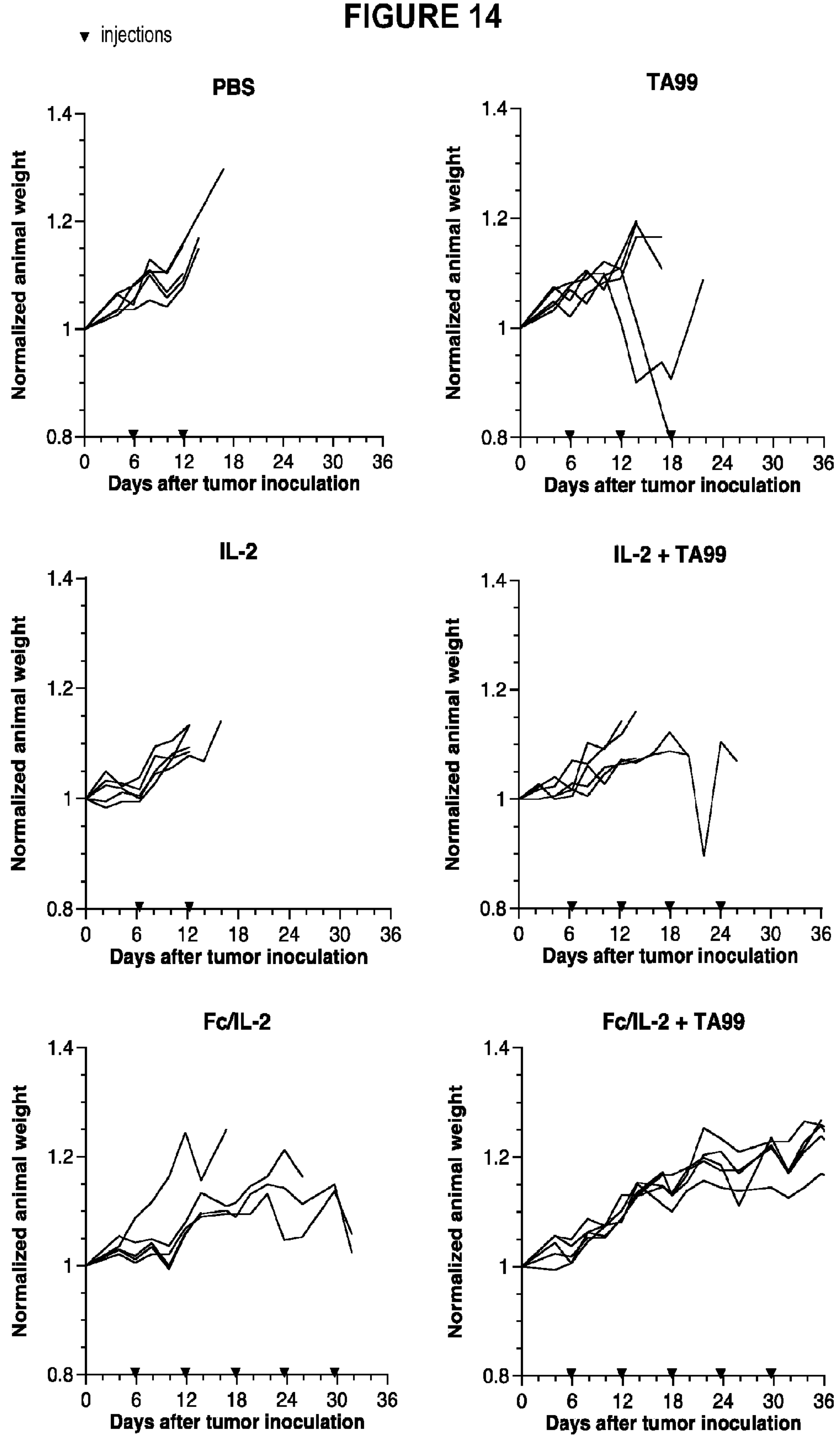
FIG. 14 is a series of graphs depicting animal weight (grams) in mice treated as described for FIG. 11. Shown is animal weight normalized to initial weight at time of tumor inoculation.

The weight of animals treated with all therapies tracked with PBS-treated controls, suggesting these therapies were well-tolerated by the mice (FIG. 14). These findings collectively demonstrate that while Fc/IL-2 can delay tumor progression, the combination of Fc/IL-2 with TA99 exerted synergistic tumor control and potently suppressed tumor growth. Moreover, the results also indicate that Fc/IL-2 and TA99 combination therapy increased lifespan.

Example 10

Separate Administration of Fc/IL-2 and TA99 Retains Therapeutic Efficacy

To determine whether simultaneous administration of Fc/IL-2 and TA99 is required or optimal for therapeutic efficacy, the administration of the two agents were separated by intervals ranging from 0 to 3 days. C57BL/6 mice were injected subcutaneously with $10^6$ B16-F10 melanoma cells, and tumors were allowed to establish for 6 days. With tumor nodules visible and palpable, mice were treated with a single dose each of 25 μg Fc/IL-2 and 100 μg TA99, separated by approximately 0, 6, 12, 18, 24, 48, or 72 hours.

Figure 15:
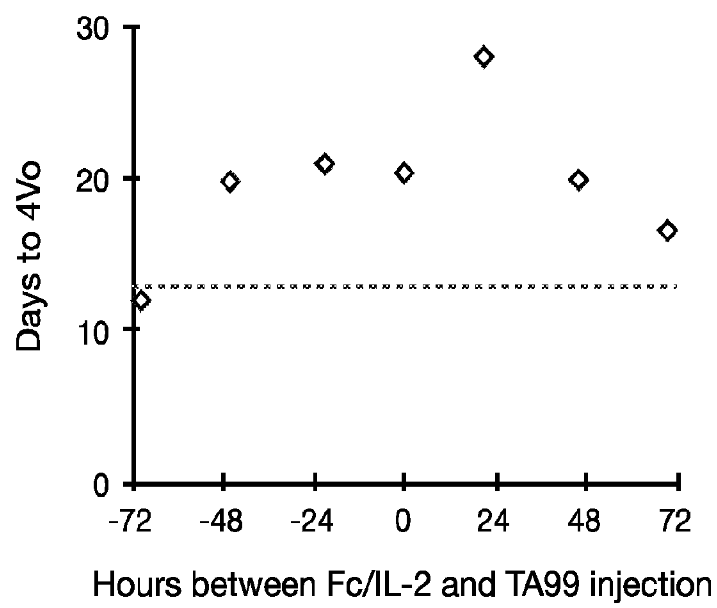
FIG. 15 is a graph depicting the time for tumor volume to double twice from its value at initial treatment based on the degree of time separation between Fc/IL-2 and TA99 injection. C57BL/6 mice were injected subcutaneously with 106 B16-F10 melanoma cells. Six days after tumor inoculation, mice were injected intravenously with PBS (dashed lines), or a single dose each of 25 μg Fc/IL-2 and 100 μg TA99 (diamonds). The y-axis represents the time for tumor volume to double twice from its value at the initiation of treatment, $V_0$. The x-axis represents the time separation between Fc/IL-2 and TA99 injection, where the time of Fc/IL-2 injection has been set as the reference, t=0. Data shown for two independent experiments.
Figure 15:
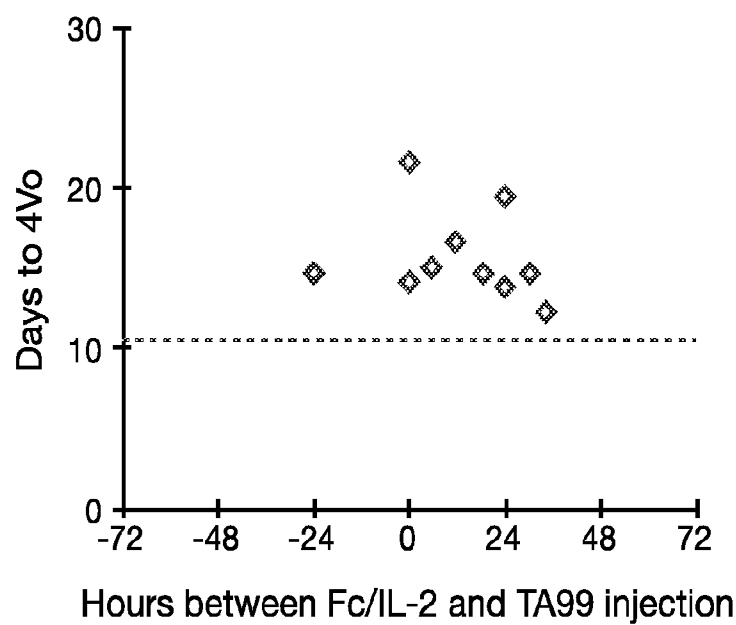

While none of these single-dose treatments cured the mice, all delayed exponential tumor growth. To compare their efficacy quantitatively, we devised the metric $4V_0$, representing the time for tumor volume to double twice (FIG. 15). This quantity captures the delayed growth due to treatment as well as the variability in initial tumor volume. Separating administration of the two agents by up to two days did not significantly affect efficacy, while separating the two agents by three days reduced tumor control effects. These data suggest that Fc/IL-2 and TA99 do not need to be administered simultaneously, but can be separated by up to 3 days and retain tumor controlling effects.

Example 11

Figure 16:
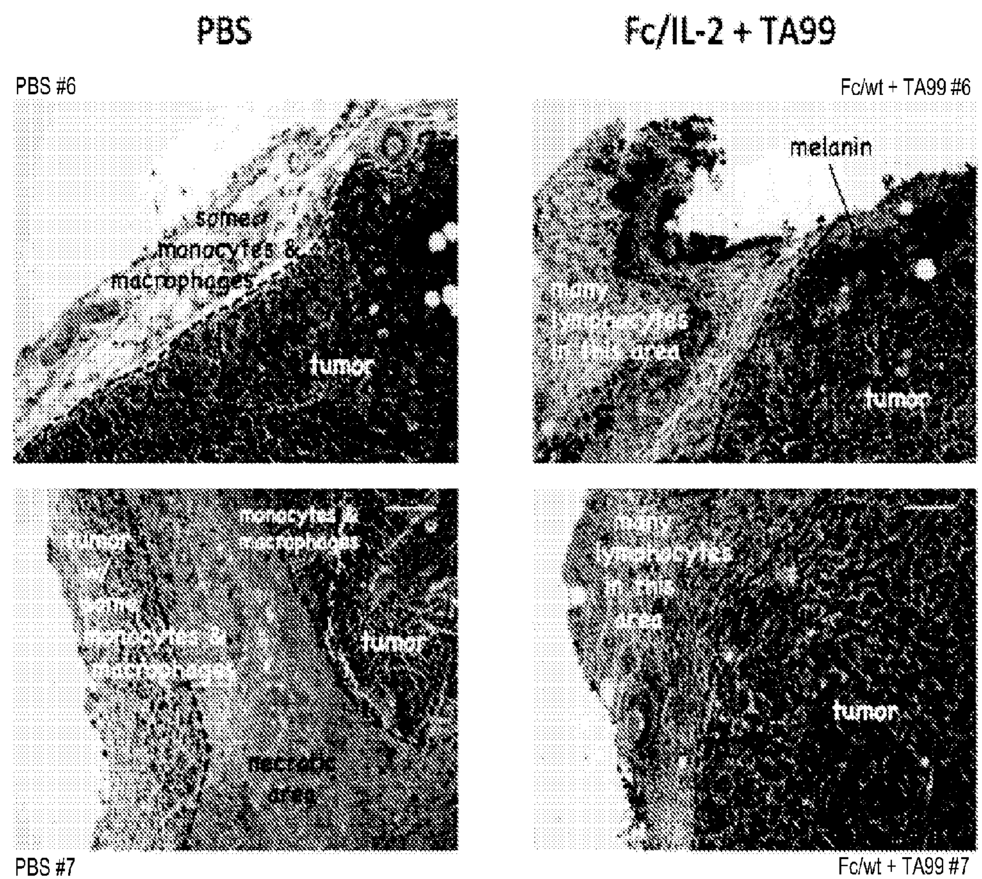
FIG. 16 is a series of photomicrographs depicting the recruitment of lymphocytes to the periphery of tumors. Hematoxylin and eosin stained sections of subcutaneous B16-F10 tumors four days after a single dose of PBS or 25 μg Fc/IL-2 and 100 μg TA99 at 10× magnification. Images are representative of two independent experiments.

Fc/IL-2 in Combination with TA99 Promotes Lymphocyte Recruitment to the Periphery of Tumors The effects of combination therapy with Fc/IL-2 and the TA99 antibody on lymphocyte recruitment to the periphery of tumors were assessed. C57BL/6 mice were injected subcutaneously with B16-F10 melanoma cells (1×$10^6$ cells) and tumors were allowed to establish for 8 days. Mice were then administered either PBS or 25 μg of Fc/IL-2 and 100 μg of TA99 antibody. Four days after single-dose therapy, tumor tissue was harvested, fixed in formalin, and stained with hematoxylin and eosin. As shown in FIG. 16, Fc/IL-2+TA99 showed significant recruitment of lymphocytes to the periphery of tumors, whereas only few lymphocytes were observed in the periphery of tumors in PBS treated mice.

Example 12

Combination Therapy of Fc/IL-2 and TA99 Suppresses Secondary Tumor Formation While combination therapy with Fc/IL-2 and TA99 effectively controls tumor growth as discussed supra, it is unclear whether the combination therapy promotes an anti-tumor memory response. Protection against a secondary tumor challenge reflects the development of a systemic anti-tumor immune response, which would also indicate a potential protective effect against tumor metastasis. To address this possibility, C57BL/6 mice were injected subcutaneously with B16-F10 melanoma cells (1×$10^5$) and tumors were allowed to establish for 6 days. After five doses of Fc/IL-2 (25 μg) and TA99 (100 μg), treatment was stopped to assess the duration of the therapeutic effect and the development of any anti-tumor memory responses.

Figure 17:
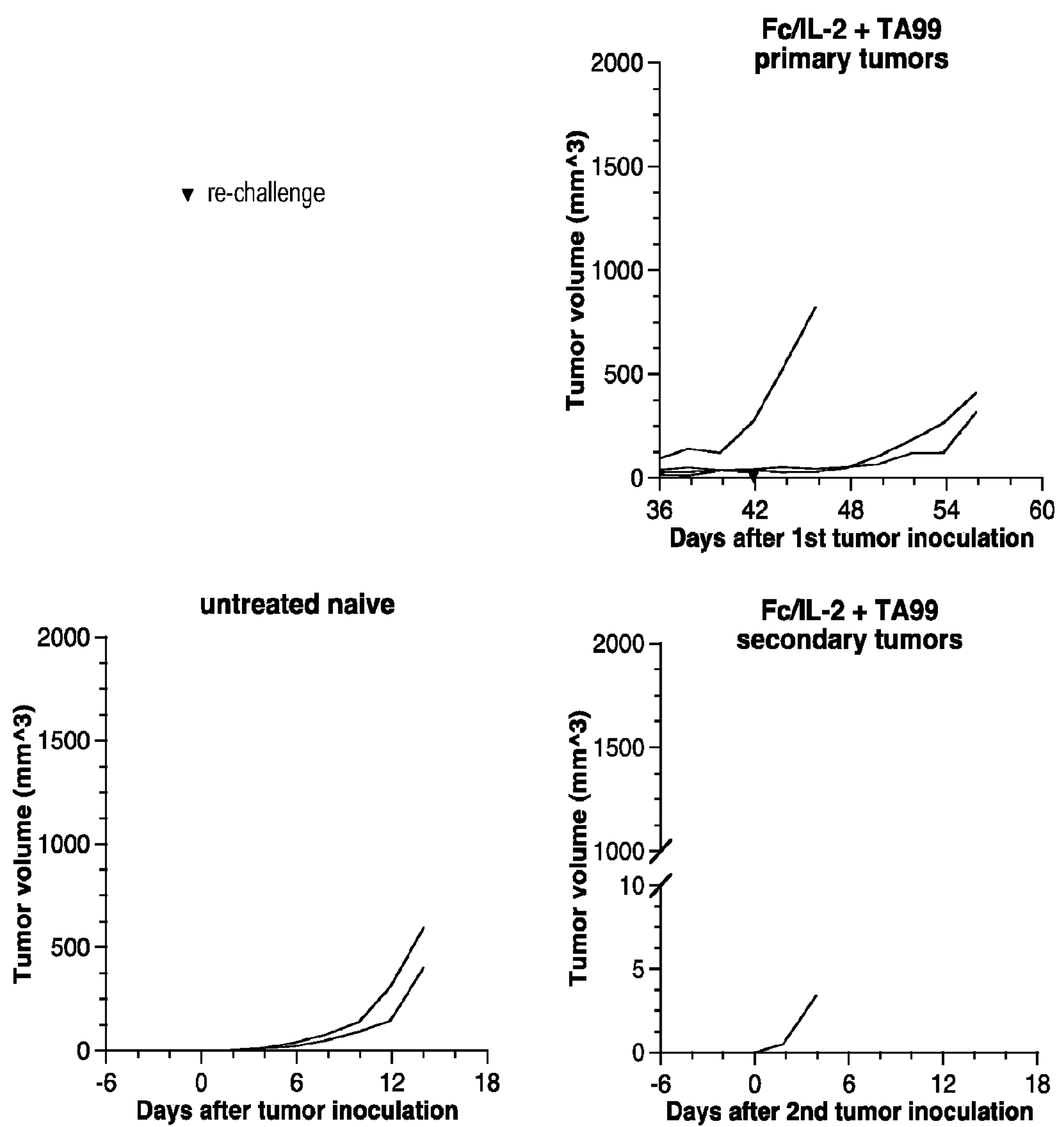
FIG. 17 is a series of graphs depicting the protection conferred by Fc/IL-2 and TA99 combination therapy against secondary tumor challenge. C57BL/6 mice bearing B16-F10 tumors were treated with five doses of 25 μg Fc/IL-2 and 100 μg TA99 (n=3). These mice were injected subcutaneously with $10^5$ B16-F10 melanoma cells in the opposite flank twelve days after the last treatment. Untreated naive C57BL/6 mice (n=2) were also injected subcutaneously with $10^5$ B16-F10 melanoma cells. Each individual line represents one mouse and inverted triangles represent a re-challenge with $10^5$ B16-F10 melanoma cells.

Twelve days after the last treatment, corresponding to 42 days after tumor inoculation, the three remaining mice of this treatment group were re-challenged with $10^5$ B16-F10 cells subcutaneously in the opposite flank. Two naive C57BL/6 mice were similarly inoculated with $10^5$ B16-F10 cells as controls. All three primary tumors eventually entered exponential growth and required euthanasia by day 26 after the last treatment. However, at the time of euthanasia, 14 days after re-challenge, two of three Fc/IL-2 and TA99 treated mice remained tumor-free at the secondary challenge site (FIG. 17). These data suggest that Fc/IL-2 and TA99 combination therapy induced an anti-tumor memory response and prevented the establishment of new tumors upon re-challenge with cancer cells.

Example 13

CD25 Binding Affinity Required for Maximal Therapeutic Effect of Combination Therapy with Fc/IL-2 and TA99

To determine whether CD25 binding affinity is required for the efficacy of combination therapy with Fc/IL-22 and TA99, Fc/IL-2 fusions were tested for their tumor controlling effects. C57BL/6 mice were injected subcutaneously with B16-F10 melanoma cells ($1\times10^6$) and tumors were allowed to establish for six days. With tumor nodules visible and palpable, mice were treated with 25 μg Fc/QQ610 (high affinity CD25-binding IL-2) or 25 μg Fc/E76G (non-CD25 binding IL-2), alone or in combination with 100 μg TA99, with subsequent doses administered every six days.

Similar to Fc/IL-2, both Fc/QQ6210 and Fc/E76G alone delayed tumor progression compared to PBS-treated controls and IL-2 (FIGS. 11 and 18), although mice treated with Fc/E76G alone reached euthanasia criteria within the course of therapy. When combined with TA99, Fc/QQ6210 exerted similar tumor growth suppressing effects than Fc/IL-2, whereas tumors resumed exponential growth with Fc/E76G+TA99 (FIG. 18). These data suggest that CD25 binding is required for the full therapeutic efficacy of the Fc/IL-2 and TA99 combination therapy, and that CD25+ cells are key effectors of the Fc/IL-2 effect.

Example 14

CD8+ T Cells and NK Cells Contribute to Therapeutic Effect

Figure 19:
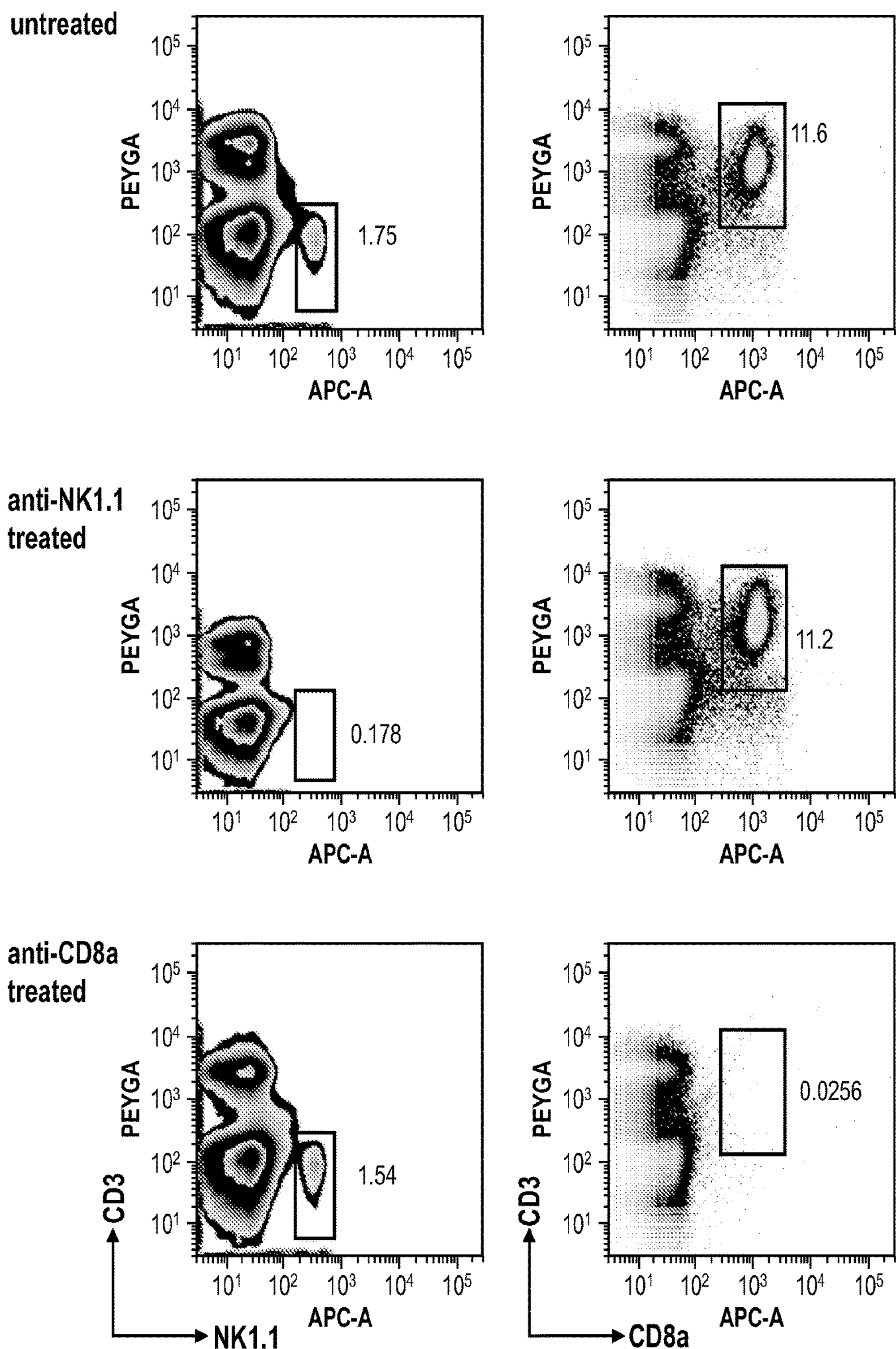
FIG. 19 depicts the fluorescence activated cell sorting (FACS)-mediated confirmation of NK cell or CD8+ cell depletion by anti-NK1.1 or anti-CD8a antibody, respectively. C57BL/6 mice (n=1 mouse/group) were injected subcutaneously with $10^6$ B16-F10 melanoma cells. Four days after tumor inoculation, mice were injected intraperitoneally with 400 μg anti-NK1.1 or 400 μg anti-CD8a antibody. Two days after antibody injection, single-cell suspensions were prepared from spleens and stained with calcein violet AM, PE-conjugated anti-CD3, and APC-conjugated anti-NK1.1 or Alexa Fluor 647-conjugated anti-CD8a. Untreated controls did not receive tumor inoculation or antibody injection. Cells were gated by forward scatter and calcein violet AM. The internal box in the panels on the left reflect NK cells, and the internal box in the panels on the right reflect CD8+ T cells.

Selective cell depletion was performed to determine which cell types were responsible for the therapeutic efficacy of the Fc/IL-2 and TA99 combination therapy. NK and CD8+ T cells were likely candidates, given their ability to mediate ADCC, cytotoxic abilities, and receive stimulation by IL-2. Anti-NK1.1 antibody (Bio X Cell, West Lebanon, N.H.; clone PK136) was used to deplete NK and NKT cells, and anti-CD8a antibody (Bio X Cell, West Lebanon, N.H.; clone 2.43) was used to deplete CD8+ cells. C57 BL/6 mice (n=5/group) were injected subcutaneously with $10^6$ B16F10 melanoma cells. Four days post tumor inoculation, and every 4 days afterward, 400 μg of antibody in 100 μl PBS were injected intra-peritoneally. Cell depletion was confirmed by flow cytometry of splenocytes (FIG. 19). Six days after tumor inoculation, mice were injected intravenously with PBS or 25 μg Fc/IL-2 and 100 μg TA99. Subsequent doses were administered every 6 days.

Figure 20:
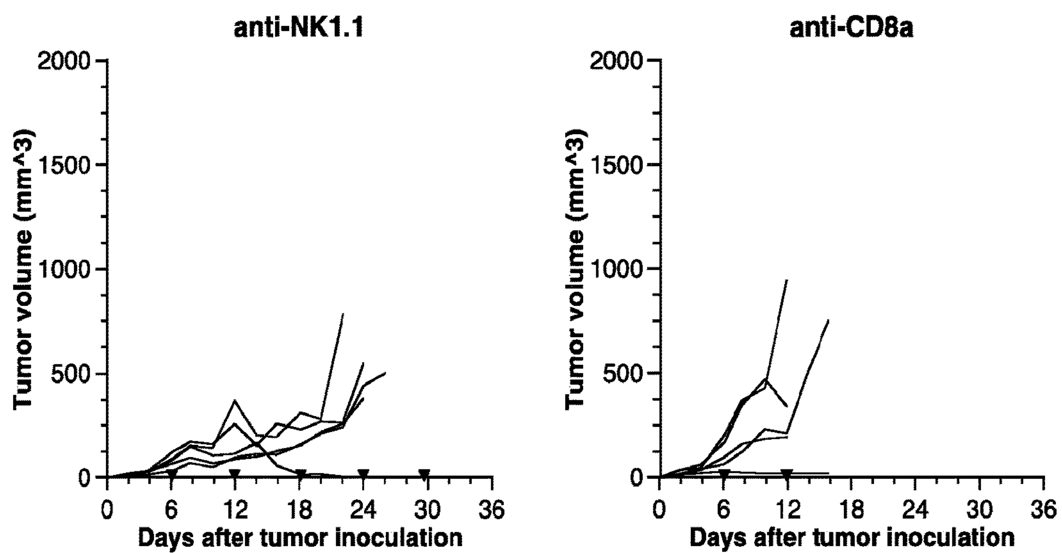
FIG. 20 is a series of graphs demonstrating that NK and CD8+ T cells contribute to the anti-tumor effects of Fc/IL-2+TA99 combination therapy. C57BL/6 mice (n=5 mice per group) were injected subcutaneously with $10^6$ B16-F10 melanoma cells. Four days after tumor inoculation, mice were injected intraperitoneally with 400 μg anti-NK1.1 or 400 μg anti-CD8a antibody; subsequent doses were administered every four days. Six days after tumor inoculation, mice were injected intravenously with PBS, 25 μg Fc/IL-2 and 100 μg TA99; subsequent doses were administered every 6 days. Each individual line represents one mouse and inverted triangles represent an injection of Fc/IL-2+TA99.

As shown in FIG. 20, the suppressive effects of Fc/IL-2 and TA99 combination therapy were lost in the absence of CD8+ T cells, suggesting that CD8+ T cells are required and are a major component of the efficacy of this combination therapy. Moreover, depletion of NK cells partially decreased tumor progression, suggesting that NK cells also play a role in the efficacy of this combination therapy. These findings are in contrast to notion that therapeutic antibodies exert their effects mainly via ADCC by NK cells.

Example 15

Tumor Control by Fc/IL-2 Fusions and a Therapeutic Antibody in Colon Cancer

Given the efficacy of the Fc/IL-2 and TA99 combination therapy, it is likely that Fc/IL-2 would synergize with other anti-tumor antibodies as well. Thus, the generalizability of the pronounced effects of extended-PK IL-2 and therapeutic antibody combination therapy were also tested in a mouse model of colon cancer.

Figure 21:
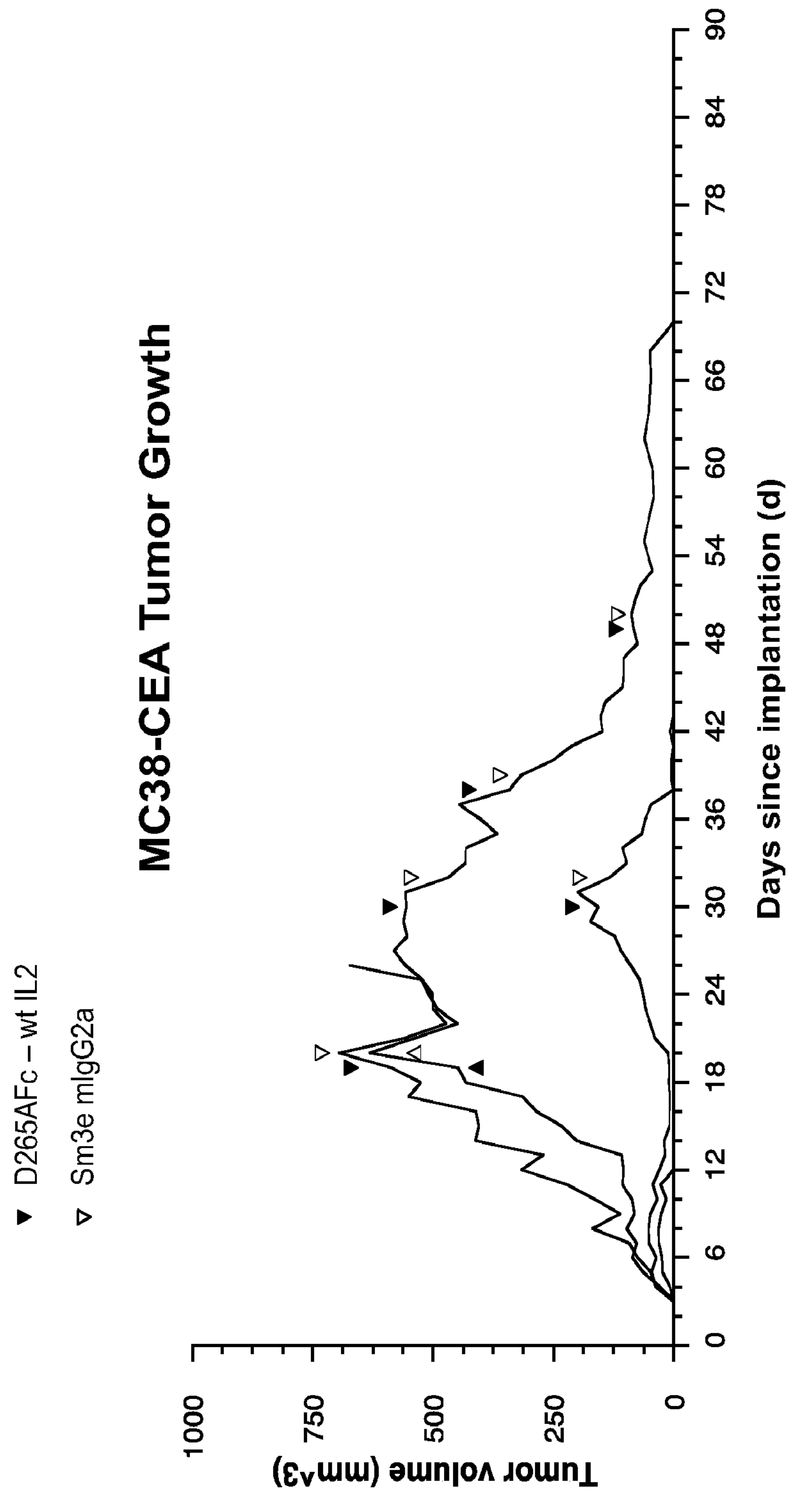
FIG. 21 is a graph depicting the effects of Fc/IL-2 and sm3E anti-CEA antibody in controlling tumor growth in a mouse model of colon cancer. MC38-CEA cells ($1\times10^6$), a colon cancer cell line that was engineered to transgenically express CEA, were injected into the flank of four C57 BL/6 J mice to induce tumor establishment. Fc-IL-2 was injected at a dosage of 25 μg/mouse retroorbitally. Sm3E anti-CEA antibody was injected at a dosage of 200 μg/mouse retroorbitally. Tumor volume was assessed as described in Example 9.

MC38-CEA cells ($1\times10^6$), a colon cancer cell line, were injected into the flank of four C57 BL/6 J mice to induce tumor establishment. Fc-IL-2 was injected at 25 μg/mouse retroorbitally. Sm3E anti-CEA antibody, a humanized IgG1 antibody with extremely high affinity for soluble and membrane-bound CEA ($K_D$=20 pM) (Graff et al., *Protein Eng Des Sel* 2004; 17:293-304), was injected at a dosage of 200 μg/mouse retroorbitally as shown in FIG. 21. Tumor volume was assessed as described in Example 7.

Pronounced decreases in tumor volume were observed in mice immediately after injection of Fc/IL-2 and the sm3e anti-CEA antibody (FIG. 21). Notably, tumors were eradicated in mouse 2 and 3 upon repeated or single combination therapy, respectively. Mouse 1 was euthanized at day 26 due to an ulcerated tumor. Mouse 2 was injected again with MC38-CEA cells in the left flank on day 24 after primary tumor implantation, but no subsequent tumors were formed. These findings demonstrate the generalizability of the pronounced therapeutic effects exerted by the combination of an extended-PK IL-2 and therapeutic antibody.

Example 16

Tumor Control by Other Types of Extended-PK IL-2 and Therapeutic Antibodies

Bivalent Fc/IL-2, PEG-IL-2, HSA-IL-2, Fn3(HSA)-IL-2 in combination with TA99 antibody or sm3e anti-CEA antibody are tested for tumor controlling effects as described in Examples 9 and 15, respectively.

Example 17

Control of Other Types of Cancer with Extended-PK IL-2 and Therapeutic Agents

Fc-IL-2, PEG-IL-2, HSA-IL-2, and Fn3(HSA)-IL-2 are tested in other mouse models of cancer in combination with therapeutic antibodies that target the particular cancer being tested. Various mouse models of cancer are known in the art. For example, $Kras^{LSL-G12D/+}$; $p53^{Flox/Flox}$ (KP) mice ("KP mice") (Xue et al., *Cancer Discovery* 2011; 1:236-47; Winslow et al., *Nature* 2011; 473; 101-4) can be made to express human CEA as a surface antigen using Cre recombinase vector, allowing for testing the efficacy of a combination therapy comprising extended-PK IL-2 and an anti-CEA antibody. The KP mice can also be used to test the efficacy of a combination therapy comprising extended-PK IL-2 and a therapeutic agent, such as the small molecule inhibitors gefitinib and erlotinib.

TABLE 5

| SEQ ID NO | DESCRIPTION | SEQUENCE |
| --- | --- | --- |
| 1 | Mouse IL-2 (nucleic acid sequence) | GCACCCACTTCAAGCTCCACTTCAAGCTCTACAGCGGAAGCACAGCAGCAGCAG CAGCAGCAGCAGCAGCAGCAGCAGCACCTGGAGCAGCTGTTGATGGACCTACAG GAGCTCCTGAGCAGGATGGAGAATTACAGGAACCTGAAACTCCCCAGGATGCTC ACCTTCAAATTTTACTTGCCCAAGCAGGCCACAGAATTGAAAGATCTTCAGTGC CTAGAAGATGAACTTGGACCTCTGCGGCATGTTCTGGATTTGACTCAAAGCAAA AGCTTTCAATTGGAAGATGCTGAGAATTTCATCAGCAATATCAGAGTAACTGTT GTAAAACTAAAGGGCTCTGACAACACATTTGAGTGCCAATTCGATGATGAGTCA GCAACTGTGGTGGACTTTCTGAGGAGATGGATAGCCTTCTGTCAAAGCATCATC TCAACAAGCCCTCAA |
| 2 | Mouse IL-2 (amino acid sequence) | APTSSSTSSSTAEAQQQQQQQQQQQQHLEQLLMDLQELLSRMENYRNLKLPRML TFKFYLPKQATELKDLQCLEDELGPLRHVLDLTQSKSFQLEDAENFISNIRVTV VKLKGSDNTFECQFDDESATVVDFLRRWIAFCQSIISTSPQ |
| 3 | QQ6210 (nucleic acid sequence) | GCACCCACTTCAAGCTCCACTTCAAGCTCTACAGCGGAAGCACAACAGCAGCAG CAGCAGCAGCAGCAGCAGCAGCAGCACCTGGAGCAGCTGTTGATGGACCTACAG GAACTCCTGAGTAGGATGGAGGATCACAGGAACCTGAGACTCCCCAGGATGCTC ACCTTCAAATTTTACTTGCCCGAGCAGGCCACAGAATTGGAAGATCTTCAGTGC CTAGAAGATGAACTTGAACCACTGCGGCAAGTTCTGGATTTGACTCAAAGCAAA AGCTTTCAATTGGAAGATGCTGAGAATTTCATCAGCAATATCAGAGTAACTGTT GTAAAACTAAAGGGCTCTGACAACACATTTGAGTGCCAATTCGACGATGAGCCA GCAACTGTGGTGGACTTTCTGAGGAGATGGATAGCCTTCTGTCAAAGCATCATC TCAACAAGCCCTCAA |
| 4 | QQ6210 (amino acid sequence) | APTSSSTSSSTAEAQQQQQQQQQQQQHLEQLLMDLQELLSRMEDHRNLRLPRML TFKFYLPEQATELEDLQCLEDELEPLRQVLDLTQSKSFQLEDAENFISNIRVTV VKLKGSDNTFECQFDDEPATVVDFLRRWIAFCQSIISTSPQ |
| 5 | E76A (nucleic acid sequence) | GCACCCACTTCAAGCTCCACTTCAAGCTCTACAGCGGAAGCACAGCAGCAGCAG CAGCAGCAGCAGCAGCAGCAGCAGCACCTGGAGCAGCTGTTGATGGACCTACAG GAGCTCCTGAGCAGGATGGAGAATTACAGGAACCTGAAACTCCCCAGGATGCTC ACCTTCAAATTTTACTTGCCCAAGCAGGCCACAGAATTGAAAGATCTTCAGTGC CTAGAAGATGCTCTTGGACCTCTGCGGCATGTTCTGGATTTGACTCAAAGCAAA AGCTTTCAATTGGAAGATGCTGAGAATTTCATCAGCAATATCAGAGTAACTGTT GTAAAACTAAAGGGCTCTGACAACACATTTGAGTGCCAATTCGATGATGAGTCA GCAACTGTGGTGGACTTTCTGAGGAGATGGATAGCCTTCTGTCAAAGCATCATC TCAACAAGCCCTCAA |
| 6 | E76A (amino acid sequence) | APTSSSTSSSTAEAQQQQQQQQQQQQHLEQLLMDLQELLSRMENYRNLKLPRML TFKFYLPKQATELKDLQCLEDALGPLRHVLDLTQSKSFQLEDAENFISNIRVTV VKLKGSDNTFECQFDDESATVVDFLRRWIAFCQSIISTSPQ |
| 7 | E76G (nucleic acid sequence) | GCACCCACTTCAAGCTCCACTTCAAGCTCTACAGCGGAAGCACAGCAGCAGCAG CAGCAGCAGCAGCAGCAGCAGCAGCACCTGGAGCAGCTGTTGATGGACCTACAG GAGCTCCTGAGCAGGATGGAGAATTACAGGAACCTGAAACTCCCCAGGATGCTC ACCTTCAAATTTTACTTGCCCAAGCAGGCCACAGAATTGAAAGATCTTCAGTGC CTAGAAGATGGTCTTGGACCTCTGCGGCATGTTCTGGATTTGACTCAAAGCAAA AGCTTTCAATTGGAAGATGCTGAGAATTTCATCAGCAATATCAGAGTAACTGTT GTAAAACTAAAGGGCTCTGACAACACATTTGAGTGCCAATTCGATGATGAGTCA GCAACTGTGGTGGACTTTCTGAGGAGATGGATAGCCTTCTGTCAAAGCATCATC TCAACAAGCCCTCAA |
| 8 | E76G (amino acid sequence) | APTSSSTSSSTAEAQQQQQQQQQQQQHLEQLLMDLQELLSRMENYRNLKLPRML TFKFYLPKQATELKDLQCLEDGLGPLRHVLDLTQSKSFQLEDAENFISNIRVTV VKLKGSDNTFECQFDDESATVVDFLRRWIAFCQSIISTSPQ |
| 9 | D265A Fc/Flag (nucleic acid sequence) (C-terminal flag tag is underlined) | ATGAGGGTCCCCGCTCAGCTCCTGGGGCTCCTGCTGCTCTGGCTCCCAGGTGCA CGATGTGAGCCCAGAGTGCCCATAACACAGAACCCCTGTCCTCCACTCAAAGAG TGTCCCCCATGCGCAGCTCCAGACCTCTTGGGTGGACCATCCGTCTTCATCTTC CCTCCAAAGATCAAGGATGTACTCATGATCTCCCTGAGCCCCATGGTCACATGT GTGGTGGTGGCCGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAAGAGGAAGTCTTTTC GCCTGCTCAGTGGTCCACGAGGGTCTGCACAATCACCTTACGACTAAGACCATC TCCCGGTCTCTGGGTAAAGGTGGCGGATCTGACTACAAGGACGACGATGACAAG TGATAA |
| 10 | D265A Fc/Flag (amino acid | MRVPAQLLGLLLLWLPGARCEPRVPITQNPCPPLKECPPCAAPDLLGGPSVFIF PPKIKDVLMISLSPMVTCVVVAVSEDDPDVQISWFVNNVEVHTAQTQTHREDYN |

TABLE 5-continued

| SEQ ID NO | DESCRIPTION | SEQUENCE |
|---|---|---|
| | sequence) (C-terminal flag tag is underlined) | STLRVVSALPIQHQDWMSGKEEKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKGGGSDYKDDDDK |
| 11 | D265A Fc/wt mIL-2 (nucleic acid sequence) (C-terminal 6x his tag is underlined) | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC<br>CCTCCAAAGATCAAGGATGTACTCATGATCTCCCTGAGCCCCATGGTCACATGT<br>GTGGTGGTGGCCGTGAGCGAGGATGACCCAGACGTCCAGATCAGCTGGTTTGTG<br>AACAACGTGGAAGTACACACAGCTCAGACACAAACCCATAGAGAGGATTACAAC<br>AGTACTCTCCGGGTGGTCAGTGCCCTCCCCATCCAGCACCAGGACTGGATGAGT<br>GGCAAGGAGTTCAAATGCAAGGTCAACAACAGAGCCCTCCCATCCCCCATCGAG<br>AAAACCATCTCAAAACCCAGAGGGCCAGTAAGAGCTCCACAGGTATATGTCTTG<br>CCTCCACCAGCAGAAGAGATGACTAAGAAAGAGTTCAGTCTGACCTGCATGATC<br>ACAGGCTTCTTACCTGCCGAAATTGCTGTGGACTGGACCAGCAATGGGCGTACA<br>GAGCAAAACTACAAGAACACCGCAACAGTCCTGGACTCTGATGGTTCTTACTTC<br>ATGTACAGCAAGCTCAGAGTACAAAAGAGCACTTGGGAAAGAGGAAGTCTTTTC<br>GCCTGCTCAGTGGTCCACGAGGGTCTGCACAATCACCTTACGACTAAGACCATC<br>TCCCGGTCTCTGGGTAAAGGAGGGGGCTCCGCACCCACTTCAAGCTCCACTTCA<br>AGCTCTACAGCGGAAGCACAGCAGCAGCAGCAGCAGCAGCAGCAGCAGCAGCAG<br>CACCTGGAGCAGCTGTTGATGGACCTACAGGAGCTCCTGAGCAGGATGGAGAAT<br>TACAGGAACCTGAAACTCCCCAGGATGCTCACCTTCAAATTTTACTTGCCCAAG<br>CAGGCCACAGAATTGAAAGATCTTCAGTGCCTAGAAGATGAACTTGGACCTCTG<br>CGGCATGTTCTGGATTTGACTCAAAGCAAAAGCTTTCAATTGGAAGATGCTGAG<br>AATTTCATCAGCAATATCAGAGTAACTGTTGTAAAACTAAAGGGCTCTGACAAC<br>ACATTTGAGTGCCAATTCGATGATGAGTCAGCAACTGTGGTGGACTTTCTGAGG<br>AGATGGATAGCCTTCTGTCAAAGCATCATCTCAACAAGCCCTCAACACCATCAC<br>CACCATCACTGATAA |
| 12 | D265A Fc/wt mIL-2 (amino acid sequence) (C-terminal 6x his tag is underlined) | MRVPAQLLGLLLLWLPGARCEPRVPITQNPCPPLKECPPCAAPDLLGGPSVFIF<br>PPKIKDVLMISLSPMVTCVVVAVSEDDPDVQISWFVNNVEVHTAQTQTHREDYN<br>STLRVVSALPIQHQDWMSGKEEKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKGGGSAPTSSSTS<br>SSTAEAQQQQQQQQQQQQHLEQLLMDLQELLSRMENYRNLKLPRMLTFKFYLPK<br>QATELKDLQCLEDELGPLRHVLDLTQSKSFQLEDAENFISNIRVTVVKLKGSDN<br>TFECQFDDESATVVDFLRRWIAFCQSIISTSPQHHHHHH** |
| 13 | D265A Fc/QQ6210 (nucleic acid sequence) (C-terminal 6x his tag is underlined) | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC<br>CCTCCAAAGATCAAGGATGTACTCATGATCTCCCTGAGCCCCATGGTCACATGT<br>GTGGTGGTGGCCGTGAGCGAGGATGACCCAGACGTCCAGATCAGCTGGTTTGTG<br>AACAACGTGGAAGTACACACAGCTCAGACACAAACCCATAGAGAGGATTACAAC<br>AGTACTCTCCGGGTGGTCAGTGCCCTCCCCATCCAGCACCAGGACTGGATGAGT<br>GGCAAGGAGTTCAAATGCAAGGTCAACAACAGAGCCCTCCCATCCCCCATCGAG<br>AAAACCATCTCAAAACCCAGAGGGCCAGTAAGAGCTCCACAGGTATATGTCTTG<br>CCTCCACCAGCAGAAGAGATGACTAAGAAAGAGTTCAGTCTGACCTGCATGATC<br>ACAGGCTTCTTACCTGCCGAAATTGCTGTGGACTGGACCAGCAATGGGCGTACA<br>GAGCAAAACTACAAGAACACCGCAACAGTCCTGGACTCTGATGGTTCTTACTTC<br>ATGTACAGCAAGCTCAGAGTACAAAAGAGCACTTGGGAAAGAGGAAGTCTTTTC<br>GCCTGCTCAGTGGTCCACGAGGGTCTGCACAATCACCTTACGACTAAGACCATC<br>TCCCGGTCTCTGGGTAAAGGAGGGGGCTCCGCACCCACTTCAAGCTCCACTTCA<br>AGCTCTACAGCGGAAGCACAACAGCAGCAGCAGCAGCAGCAGCAGCAGCAGCAG<br>CACCTGGAGCAGCTGTTGATGGACCTACAGGAACTCCTGAGTAGGATGGAGGAT<br>CACAGGAACCTGAGACTCCCCAGGATGCTCACCTTCAAATTTTACTTGCCCGAG<br>CAGGCCACAGAATTGGAAGATCTTCAGTGCCTAGAAGATGAACTTGAACCACTG<br>CGGCAAGTTCTGGATTTGACTCAAAGCAAAAGCTTTCAATTGGAAGATGCTGAG<br>AATTTCATCAGCAATATCAGAGTAACTGTTGTAAAACTAAAGGGCTCTGACAAC<br>ACATTTGAGTGCCAATTCGACGATGAGCCAGCAACTGTGGTGGACTTTCTGAGG<br>AGATGGATAGCCTTCTGTCAAAGCATCATCTCAACAAGCCCTCAACACCATCAC<br>CACCATCACTGATAA |
| 14 | D265A Fc/QQ6210 (amino acid sequence) (C-terminal 6x his tag is underlined) | MRVPAQLLGLLLLWLPGARCEPRVPITQNPCPPLKECPPCAAPDLLGGPSVFIF<br>PPKIKDVLMISLSPMVTCVVVAVSEDDPDVQISWFVNNVEVHTAQTQTHREDYN<br>STLRVVSALPIQHQDWMSGKEEKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKGGGSAPTSSSTS<br>SSTAEAQQQQQQQQQQQQHLEQLLMDLQELLSRMEDHRNLRLPRMLTFKFYLPE<br>QATELEDLQCLEDELEPLRQVLDLTQSKSFQLEDAENFISNIRVTVVKLKGSDN<br>TFECQFDDEPATVVDFLRRWIAFCQSIIHSTSPQHHHHHH |
| 15 | D265A Fc/E76A (nucleic acid sequence) | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC |

TABLE 5-continued

SEQUENCES

| SEQ ID NO | DESCRIPTION | SEQUENCE |
|---|---|---|
| | (C-terminal 6x his tag is underlined) | CCTCCAAAGATCAAGGATGTACTCATGATCTCCCTGAGCCCCATGGTCACATGT GTGGTGGTGGCCGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAAGAGGAAGTCTTTTC GCCTGCTCAGTGGTCCACGAGGGTCTGCACAATCACCTTACGACTAAGACCATC TCCCGGTCTCTGGGTAAAGGAGGGGGCTCCGCACCCACTTCAAGCTCCACTTCA AGCTCTACAGCGGAAGCACAGCAGCAGCAGCAGCAGCAGCAGCAGCAGCAGCAG CACCTGGAGCAGCTGTTGATGGACCTACAGGAGCTCCTGAGCAGGATGGAGAAT TACAGGAACCTGAAACTCCCCAGGATGCTCACCTTCAAATTTTACTTGCCCAAG CAGGCCACAGAATTGAAAGATCTTCAGTGCCTAGAAGATGCTCTTGGACCTCTG CGGCATGTTCTGGATTTGACTCAAAGCAAAAGCTTTCAATTGGAAGATGCTGAG AATTTCATCAGCAATATCAGAGTAACTGTTGTAAAACTAAAGGGCTCTGACAAC ACATTTGAGTGCCAATTCGATGATGAGTCAGCAACTGTGGTGGACTTTCTGAGG AGATGGATAGCCTTCTGTCAAAGCATCATCTCAACAAGCCCTCAACACCATCAC CACCATCACTGATAA |
| 16 | D265A Fc/E76A (amino acid sequence) (C-terminal 6x his tag is underlined) | MRVPAQLLGLLLLWLPGARCEPRVPITQNPCPPLKECPPCAAPDLLGGPSVFIF PPKIKDVLMISLSPMVTCVVVAVSEDDPDVQISWFVNNVEVHTAQTQTHREDYN STLRVVSALPIQHQDWMSGKEEKCKVNNRALPSPIEKTISKPRGPVRAPQVYVL PPPAEEMTKKEFSLTCMITGFLPAEIAVDWTSNGRTEQNYKNTATVLDSDGSYF MYSKLRVQKSTWERGSLFACSVVHEGLHNHLTTKTISRSLGKGGGSAPTSSSTS SSTAEAQQQQQQQQQQQQHLEQLLMDLQELLSRMENYRNLKLPRMLTFKFYLPK QATELKDLQCLEDALGPLRHVLDLTQSKSFQLEDAENFISNIRVTVVKLKGSDN TFECQFDDESATVVDFLRRWIAFCQSIIHSTSPQHHHHHH |
| 17 | D265A Fc/E76G (nucleic acid sequence) (C-terminal 6x his tag is underlined) | ATGAGGGTCCCCGCTCAGCTCCTGGGGCTCCTGCTGCTCTGGCTCCCAGGTGCA CGATGTGAGCCCAGAGTGCCCATAACACAGAACCCCTGTCCTCCACTCAAAGAG TGTCCCCCATGCGCAGCTCCAGACCTCTTGGGTGGACCATCCGTCTTCATCTTC CCTCCAAAGATCAAGGATGTACTCATGATCTCCCTGAGCCCCATGGTCACATGT GTGGTGGTGGCCGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAAGAGGAAGTCTTTTC GCCTGCTCAGTGGTCCACGAGGGTCTGCACAATCACCTTACGACTAAGACCATC TCCCGGTCTCTGGGTAAAGGAGGGGGCTCCGCACCCACTTCAAGCTCCACTTCA AGCTCTACAGCGGAAGCACAGCAGCAGCAGCAGCAGCAGCAGCAGCAGCAGCAG CACCTGGAGCAGCTGTTGATGGACCTACAGGAGCTCCTGAGCAGGATGGAGAAT TACAGGAACCTGAAACTCCCCAGGATGCTCACCTTCAAATTTTACTTGCCCAAG CAGGCCACAGAATTGAAAGATCTTCAGTGCCTAGAAGATGGTCTTGGACCTCTG CGGCATGTTCTGGATTTGACTCAAAGCAAAAGCTTTCAATTGGAAGATGCTGAG AATTTCATCAGCAATATCAGAGTAACTGTTGTAAAACTAAAGGGCTCTGACAAC ACATTTGAGTGCCAATTCGATGATGAGTCAGCAACTGTGGTGGACTTTCTGAGG AGATGGATAGCCTTCTGTCAAAGCATCATCTCAACAAGCCCTCAACACCATCAC CACCATCACTGATAA |
| 18 | D265A Fc/E76G (amino acid sequence) (C-terminal 6x his tag is underlined) | MRVPAQLLGLLLLWLPGARCEPRVPITQNPCPPLKECPPCAAPDLLGGPSVFIF PPKIKDVLMISLSPMVTCVVVAVSEDDPDVQISWFVNNVEVHTAQTQTHREDYN STLRVVSALPIQHQDWMSGKEEKCKVNNRALPSPIEKTISKPRGPVRAPQVYVL PPPAEEMTKKEFSLTCMITGFLPAEIAVDWTSNGRTEQNYKNTATVLDSDGSYF MYSKLRVQKSTWERGSLFACSVVHEGLHNHLTTKTISRSLGKGGGSAPTSSSTS SSTAEAQQQQQQQQQQQQHLEQLLMDLQELLSRMENYRNLKLPRMLTFKFYLPK QATELKDLQCLEDGLGPLRHVLDLTQSKSFQLEDAENFISNIRVTVVKLKGSDN TFECQFDDESATVVDFLRRWIAFCQSIISTSPQHHHHHH |
| 19 | mIL-2 QQ 6.2-4 (nucleic acid sequence) | GCACCCACCTCAAGCTCCACTTCAAGCTCTACAGCGGAAGCACAACAGCAGCAG CAGCAGCAGCAGCAGCAGCAGCAGCACCTGGAGCAGCTGTTGATGGACCTACAG GAGCTCCTGAGCAGGATGGAGGATTCCAGGAACCTGAGACTCCCCAGGATGCTC ACCTTCAAATTTTACTTGCCCAAGCAGGCCACAGAATTGGAAGATCTTCAGTGC CTAGAAGATGAACTTGAACCTCTGCGGCAAGTTCTGGATTTGACTCAAAGCAAA AGCTTTCAATTGGAAGATGCTGAGAATTTCATCAGCAATATCAGAGTAACTGTT GTAAAACTAAAGGGCTCTGACAACACATTTGAGTGCCAATTCGATGATGAGCCA GCAACTGTGGTGGGCTTTCTGAGGAGATGGATAGCCTTCTGTCAAAGCATCATC TCAACGAGCCCTCAA |

TABLE 5-continued

SEQUENCES

| SEQ ID NO | DESCRIPTION | SEQUENCE |
|---|---|---|
| 20 | mIL-2 QQ 6.2-4 (amino acid sequence) | APTSSSTSSSTAEAQQQQQQQQQQQQHLEQLLMDLQELLSRMEDSRNLRLPRML<br>TFKFYLPKQATELEDLQCLEDELEPLRQVLDLTQSKSFQLEDAENFISNIRVTV<br>VKLKGSDNTFECQFDDEPATVVGFLRRWIAFCQSIISTSPQ |
| 21 | mIL-2 QQ 6.2-8 (nucleic acid sequence) | GCACCCACCTCAAGCTCCACTTCAAGCTCTACAGCGGAAGCACAACAGCAGCAG<br>CAGCAGCAGCAGCACCTGGAGCAGCTGTTGATGGACCTACAGGAGCTCCTGAGT<br>AGGATGGAGGATCACAGGAACCTGAGACTCCCCAGGATGCTCACCTTCAAATTT<br>TACTTGCCCAAGCAGGCCACAGAATTGGAAGATCTTCAGTGCCTAGAAGATGAA<br>CTTGAACCTCTGCGGCAAGTTCTGGATTTGACTCAAAGCAAAAGCTTTCAATTG<br>GAAGATGCTGAGAATTTCATCAGCAATATCAGAGTAACTGTTGTAAAACTAAAG<br>GGCTCTGACAACACATTTGAGTGCCAATTCGATGATGAGCCAGCAACTGTGGTG<br>GACTTTCTGAGGAGATGGATAGCCTTCTGTCAAAGCATCATCTCAACAAGCCCT<br>CGA |
| 22 | mIL-2 QQ 6.2-8 (amino acid sequence) | APTSSSTSSSTAEAQQQQQQQQHLEQLLMDLQELLSRMEDHRNLRLPRMLTFKF<br>YLPKQATELEDLQCLEDELEPLRQVLDLTQSKSFQLEDAENFISNIRVTVVKLK<br>GSDNTFECQFDDEPATVVDFLRRWIAFCQSIISTSPR |
| 23 | mIL-2 QQ 6.2-10 (nucleic acid sequence) | GCACCCACCTCAAGCTCCACTTCAAGCTCTACAGCGGAAGCACAACAGCAGCAG<br>CAGCAGCAGCAGCAGCAGCAGCAGCACCTGGAGCAGCTGTTGATGGACCTACAG<br>GAACTCCTGAGTAGGATGGAGGATCACAGGAACCTGAGACTCCCCAGGATGCTC<br>ACCTTCAAATTTTACTTGCCCGAGCAGGCCACAGAATTGGAAGATCTTCAGTGC<br>CTAGAAGATGAACTTGAACCACTGCGGCAAGTTCTGGATTTGACTCAAAGCAAA<br>AGCTTTCAATTGGAAGATGCTGAGAATTTCATCAGCAATATCAGAGTAACTGTT<br>GTAAAACTAAAGGGCTCTGACAACACATTTGAGTGCCAATTCGACGATGAGCCA<br>GCAACTGTGGTGGACTTTCTGAGGAGATGGATAGCCTTCTGTCAAAGCATCATC<br>TCAACAAGCCCTCAG |
| 24 | mIL-2 QQ 6.2-10 (amino acid sequence) | APTSSSTSSSTAEAQQQQQQQQQQQQHLEQLLMDLQELLSRMEDHRNLRLPRML<br>TFKFYLPEQATELEDLQCLEDELEPLRQVLDLTQSKSFQLEDAENFISNIRVTV<br>VKLKGSDNTFECQFDDEPATVVDFLRRWIAFCQSIISTSPQ |
| 25 | mIL-2 QQ 6.2-11 (nucleic acid sequence) | GCACCCACCTCAAGCTCCACTTCAAGCTCTACAGCGGAAGCACAACAGCAGCAG<br>CAGCAGCAGCAGCAGCACCTGGAGCAGCTGTTGATGGACCTACAGGAGCTCCTG<br>AGCAGGATGGAGGATTCCAGGAACCTGAGACTCCCCAGAATGCTCACCTTCAAA<br>TTTTACTTGCCCGAGCAGGCCACAGAATTGAAAGATCTCCAGTGCCTAGAAGAT<br>GAACTTGAACCTCTGCGGCAAGTTCTGGATTTGACTCAAAGCAAAAGCTTTCAA<br>TTGGAAGATGCTGAGAATTTCATCAGCAATATCAGAGTAACTGTTGTAAAACTA<br>AAGGGCTCTGACAACACATTTGAGTGCCAATTCGACGATGAGCCAGCAACTGTG<br>GTGGACTTTCTGAGGAGATGGATAGCCTTCTGTCAAAGCATCATCTCAACAAGC<br>CCTCAG |
| 26 | mIL-2 QQ 6.2-11 (amino acid sequence) | APTSSSTSSSTAEAQQQQQQQQQHLEQLLMDLQELLSRMEDSRNLRLPRMLTFK<br>FYLPEQATELKDLQCLEDELEPLRQVLDLTQSKSFQLEDAENFISNIRVTVVKL<br>KGSDNTFECQFDDEPATVVDFLRRWIAFCQSIISTSPQ |
| 27 | mIL-2 QQ 6.2-13 (nucleic acid sequence) | GCACCCACCTCAAGCTCCACTTCAAGCTCTACAGCGGAAGCACAACAGCAGCAG<br>CAGCAGCAGCAGCAGCAGCAGCAGCACCTGGAGCAGCTGTTGATGGACCTACAG<br>GAGCTCCTGAGTAGGATGGAGGATCACAGGAACCTGAGACTCCCCAGGATGCTC<br>ACCTTCAAATTTTACTTGCCCGAGCAGGCCACAGAATTGAAAGATCTCCAGTGC<br>CTAGAAGATGAACTTGAACCTCTGCGGCAGGTTCTGGATTTGACTCAAAGCAAA<br>AGCTTTCAATTGGAAGATGCTGAGAATTTCATCAGCAATATCAGAGTAACTGTT<br>GTAAAACTAAAGGGCTCTGACAACACATTTGAGTGCCAATTCGATGATGAGCCA<br>GCAACTGTGGTGGACTTTCTGAGGAGATGGATAGCCTTCTGTCAAAGCATCATC<br>TCAACAAGCCCTCAG |
| 28 | mIL-2 QQ 6.2-13 (amino acid sequence) | APTSSSTSSSTAEAQQQQQQQQQQQQHLEQLLMDLQELLSRMEDHRNLRLPRML<br>TFKFYLPEQATELKDLQCLEDELEPLRQVLDLTQSKSFQLEDAENFISNIRVTV<br>VKLKGSDNTFECQFDDEPATVVDFLRRWIAFCQSIISTSPQ |
| 29 | Full length human IL-2 (nucleic acid sequence) | ATGTACAGGATGCAACTCCTGTCTTGCATTGCACTAAGTCTTGCACTTGTCACA<br>AACAGTGCACCTACTTCAAGTTCTACAAAGAAAACACAGCTACAACTGGAGCAT<br>TTACTGCTGGATTTACAGATGATTTTGAATGGAATTAATAATTACAAGAATCCC<br>AAACTCACCAGGATGCTCACATTTAAGTTTTACATGCCCAAGAAGGCCACAGAA<br>CTGAAACATCTTCAGTGTCTAGAAGAAGAACTCAAACCTCTGGAGGAAGTGCTA<br>AATTTAGCTCAAAGCAAAAACTTTCACTTAAGACCCAGGGACTTAATCAGCAAT<br>ATCAACGTAATAGTTCTGGAACTAAAGGGATCTGAAACAACATTCATGTGTAAT<br>ATGCTGATGAGACAGCAACCATTGTAGAATTTCTGAACAGATGGATTACCTTTT<br>GTCAAAGCATCATCTCAACACTGACTTGA |
| 30 | Full length human IL-2 (amino acid sequence) | MYRMQLLSCIALSLALVTNSAPTSSSTKKTQLQLEHLLLDLQMILNGINNYKNP<br>KLTRMLTEKEYMPKKATELKHLQCLEEELKPLEEVLNLAQSKNEHLRPRDLISN<br>INVIVLELKGSETTFMCEYADETATIVEFLNRWITFCQSIISTLT |

TABLE 5-continued

| SEQ ID NO | DESCRIPTION | SEQUENCE |
|---|---|---|
| 31 | Human IL-2 without signal peptide (nucleic acid sequence) | GCACCTACTTCAAGTTCTACAAAGAAAACACAGCTACAACTGGAGCATTTACTG CTGGATTTACAGATGATTTTGAATGGAATTAATAATTACAAGAATCCCAAACTC ACCAGGATGCTCACATTTAAGTTTTACATGCCCAAGAAGGCCACAGAACTGAAA CATCTTCAGTGTCTAGAAGAAGAACTCAAACCTCTGGAGGAAGTGCTAAATTTA GCTCAAAGCAAAAACTTTCACTTAAGACCCAGGGACTTAATCAGCAATATCAAC GTAATAGTTCTGGAACTAAAGGGATCTGAAACAACATTCATGTGTAATATGCTG ATGAGACAGCAACCATTGTAGAATTTCTGAACAGATGGATTACCTTTTGTCAAA GCATCATCTCAACACTGACTTGA |
| 32 | Human IL-2 without signal peptide (amino acid sequence) | APTSSSTKKTQLQLEHLLLDLQMILNGINNYKNPKLTRMLTFKFYMPKKATELK HLQCLEEELKPLEEVLNLAQSKNFHLRPRDLISNINVIVLELKGSETTFMCEYA DETATIVEFLNRWITFCQSIISTLT |
| 33 | Human IgG1 constant region (amino acid sequence) | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSL SLSPGK |
| 34 | Human IgG1 Fc domain (amino acid sequence) | EPKSCDKTHTCPPCPAPELLGGPSVFLEPPKPKDTLMISRTPEVTCVVVDVSHE DPEVKLNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEA LHNHYTQKSLSLSPGK |

The invention claimed is:

1. A method for treating cancer in a subject in need thereof, comprising administering to the subject an effective amount of a fusion protein consisting of a human IL-2 moiety, an Fc domain and, optionally, a linker; and an effective amount of a therapeutic antibody.

2. The method of claim 1, wherein the Fc domain is mutated to reduce binding to Fcγ receptors, complement proteins, or both.

3. The method of claim 1, wherein the fusion protein comprises a monomer of one IL-2 moiety linked to an Fc domain as a heterodimer.

4. The method of claim 1, wherein the fusion protein comprises a dimer of two IL-2 moieties linked to an Fc domain as a heterodimer.

5. The method of claim 1, wherein the IL-2 is mutated such that it has higher affinity for the IL-2R alpha receptor compared to unmodified IL-2.

6. The method of claim 1, wherein the fusion protein and the therapeutic antibody are administered simultaneously or sequentially.

7. The method of claim 1, wherein the cancer is selected from the group consisting of melanoma, colon cancer, breast cancer, renal cancer, testicular cancer, ovarian cancer, prostate cancer, cancer of the small intestine, cancer of the esophagus, cervical cancer, lung cancer, lymphoma, and leukemia.

8. The method of claim 1, further comprising administering an additional therapeutic agent selected from the group consisting of a cytokine, and a chemotherapeutic agent.

9. A method of inhibiting growth and/or proliferation of tumor cells in a subject comprising administering an effective amount of a fusion protein consisting of a human IL-2 moiety, an Fc domain and, optionally, a linker; and an effective amount of a therapeutic antibody.

10. A method of increasing recruitment of lymphocytes to the periphery of a tumor in a subject comprising administering an effective amount of a fusion protein consisting of a human IL-2 moiety, an Fc domain and, optionally, a linker; and an effective amount of a therapeutic antibody.

11. A method of stimulating T cells and/or NK cells in a subject comprising administering an effective amount of a fusion protein consisting of a human IL-2 moiety, an Fc domain and, optionally, a linker; and an effective amount of a therapeutic antibody.

12. The method of claim 1, wherein the fusion protein and the therapeutic antibody are formulated as separate compositions.

13. The method of claim 1, wherein the therapeutic antibody is selected from the group consisting of trastuzumab, bevacizumab, rituximab, pertuzumab, cetuximab, IMC-1C11, tositumomab, EMD 7200, SGN-30, SGN-15, SGN-33, SGN-40, SGN-35, SGN-70, SGN-75, SGN-17/19, brentuximab vedotin, ipilimumab, ofatumumab, panitumumab, alemtuxumab, gemtuzumab ozogamicin, tremelimumab and daclizumab.

14. The method of claim 9 wherein the Fc domain is mutated to reduce binding to Fcγ receptors, complement proteins, or both.

15. The method of claim 9, wherein the fusion protein comprises a monomer of one IL-2 moiety linked to an Fc domain as a heterodimer.

16. The method of claim 9, wherein the fusion protein comprises a dimer of two IL-2 moieties linked to an Fc domain as a heterodimer.

17. The method of claim 9, wherein the IL-2 is mutated such that it has higher affinity for the IL-2R alpha receptor compared to unmodified IL-2.

18. The method of claim 9, wherein the fusion protein-and the therapeutic antibody are administered simultaneously or sequentially.

19. The method of claim 9, wherein the fusion protein and the therapeutic antibody are formulated as separate compositions.

20. The method of claim 9, further comprising administering an additional therapeutic agent selected from the group consisting of a cytokine, and a chemotherapeutic agent.

21. The method of claim 9, wherein the therapeutic antibody is selected from the group consisting of trastuzumab, bevacizumab, rituximab, pertuzumab, cetuximab, IMC-1C11, tositumomab, EMD 7200, SGN-30, SGN-15, SGN-33, SGN-40, SGN-35, SGN-70, SGN-75, SGN-17/19, brentuximab vedotin, ipilimumab, ofatumumab, panitumumab, alemtuxumab, gemtuzumab ozogamicin, tremelimumab and daclizumab.

22. The method of claim 10 wherein the Fc domain is mutated to reduce binding to Fcγ receptors, complement proteins, or both.

23. The method of claim 10, wherein the fusion protein comprises a monomer of one IL-2 moiety linked to an Fc domain as a heterodimer.

24. The method of claim 10, wherein the fusion protein comprises a dimer of two IL-2 moieties linked to an Fc domain as a heterodimer.

25. The method of claim 10, wherein the IL-2 is mutated such that it has higher affinity for the IL-2R alpha receptor compared to unmodified IL-2.

26. The method of claim 10, wherein the fusion protein-and the therapeutic antibody are administered simultaneously or sequentially.

27. The method of claim 10, wherein the fusion protein and the therapeutic antibody are formulated as separate compositions.

28. The method of claim 10, further comprising administering an additional therapeutic agent selected from the group consisting of a cytokine, and a chemotherapeutic agent.

29. The method of claim 10, wherein the therapeutic antibody is selected from the group consisting of trastuzumab, bevacizumab, rituximab, pertuzumab, cetuximab, IMC-1C11, tositumomab, EMD 7200, SGN-30, SGN-15, SGN-33, SGN-40, SGN-35, SGN-70, SGN-75, SGN-17/19, brentuximab vedotin, ipilimumab, ofatumumab, panitumumab, alemtuxumab, gemtuzumab ozogamicin, tremelimumab and daclizumab.

30. The method of claim 11 wherein the Fc domain is mutated to reduce binding to Fcγ receptors, complement proteins, or both.

31. The method of claim 11, wherein the fusion protein comprises a monomer of one IL-2 moiety linked to an Fc domain as a heterodimer.

32. The method of claim 11, wherein the fusion protein comprises a dimer of two IL-2 moieties linked to an Fc domain as a heterodimer.

33. The method of claim 11, wherein the IL-2 is mutated such that it has higher affinity for the IL-2R alpha receptor compared to unmodified IL-2.

34. The method of claim 11, wherein the fusion protein-and the therapeutic antibody are administered simultaneously or sequentially.

35. The method of claim 11, wherein the fusion protein and the therapeutic antibody are formulated as separate compositions.

36. The method of claim 11, further comprising administering an additional therapeutic agent selected from the group consisting of a cytokine, and a chemotherapeutic agent.

37. The method of claim 11, wherein the therapeutic antibody is selected from the group consisting of trastuzumab, bevacizumab, rituximab, pertuzumab, cetuximab, IMC-1C11, tositumomab, EMD 7200, SGN-30, SGN-15, SGN-33, SGN-40, SGN-35, SGN-70, SGN-75, SGN-17/19, brentuximab vedotin, ipilimumab, ofatumumab, panitumumab, alemtuxumab, gemtuzumab ozogamicin, tremelimumab and daclizumab.

38. The method of claim 1, wherein the therapeutic antibody binds a cancer antigen.

39. The method of claim 9, wherein the therapeutic antibody binds a cancer antigen.

40. The method of claim 10, wherein the therapeutic antibody binds a cancer antigen.

41. The method of claim 11, wherein the therapeutic antibody binds a cancer antigen.

* * * * *

SEQUENCE LISTING

<160> NUMBER OF SEQ ID NOS: 50

<210> SEQ ID NO 1
<211> LENGTH: 447
<212> TYPE: DNA
<213> ORGANISM: Mouse sp.
<220> FEATURE:
<221> NAME/KEY: misc_feature
<223> OTHER INFORMATION: Mouse IL-2 (nucleic acid sequence)

<400> SEQUENCE: 1

```
gcacccactt caagctccac ttcaagctct acagcggaag cacagcagca gcagcagcag     60

cagcagcagc agcagcagca cctggagcag ctgttgatgg acctacagga gctcctgagc    120

aggatggaga attacaggaa cctgaaactc cccaggatgc tcaccttcaa attttacttg    180

cccaagcagg ccacagaatt gaaagatctt cagtgcctag aagatgaact tggacctctg    240

cggcatgttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgatg atgagtcagc aactgtggtg gactttctga ggagatggat agccttctgt    420

caaagcatca tctcaacaag ccctcaa                                         447
```

<210> SEQ ID NO 2
<211> LENGTH: 149
<212> TYPE: PRT
<213> ORGANISM: Mouse sp.
<220> FEATURE:
<221> NAME/KEY: misc_feature
<223> OTHER INFORMATION: Mouse IL-2 (amino acid sequence)

<400> SEQUENCE: 2

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 3
<211> LENGTH: 447
<212> TYPE: DNA
<213> ORGANISM: Artificial Sequence
<220> FEATURE:
<223> OTHER INFORMATION: Synthetic construct: QQ6210 (nucleic acid sequence)

<400> SEQUENCE: 3

```
gcacccactt caagctccac ttcaagctct acagcggaag cacaacagca gcagcagcag     60

cagcagcagc agcagcagca cctggagcag ctgttgatgg acctacagga actcctgagt    120

aggatggagg atcacaggaa cctgagactc cccaggatgc tcaccttcaa attttacttg    180

cccgagcagg ccacagaatt ggaagatctt cagtgcctag aagatgaact tgaaccactg    240

cggcaagttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgacg atgagccagc aactgtggtg gactttctga ggagatggat agccttctgt    420

caaagcatca tctcaacaag ccctcaa                                        447
```

<210> SEQ ID NO 4
<211> LENGTH: 149
<212> TYPE: PRT
<213> ORGANISM: Artificial Sequence
<220> FEATURE:
<223> OTHER INFORMATION: Synthetic construct: QQ6210 (amino acid sequence)

<400> SEQUENCE: 4

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60
```

```
Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 5
<211> LENGTH: 447
<212> TYPE: DNA
<213> ORGANISM: Artificial Sequence
<220> FEATURE:
<223> OTHER INFORMATION: Synthetic construct: E76A (nucleic acid
      sequence)

<400> SEQUENCE: 5

gcacccactt caagctccac ttcaagctct acagcggaag cacagcagca gcagcagcag     60

cagcagcagc agcagcagca cctggagcag ctgttgatgg acctacagga gctcctgagc    120

aggatggaga attacaggaa cctgaaactc cccaggatgc tcaccttcaa attttacttg    180

cccaagcagg ccacagaatt gaaagatctt cagtgcctag aagatgctct tggacctctg    240

cggcatgttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgatg atgagtcagc aactgtggtg gactttctga ggagatggat agccttctgt    420

caaagcatca tctcaacaag ccctcaa                                        447


<210> SEQ ID NO 6
<211> LENGTH: 149
<212> TYPE: PRT
<213> ORGANISM: Artificial Sequence
<220> FEATURE:
<223> OTHER INFORMATION: Synthetic construct: E76A (amino acid sequence)

<400> SEQUENCE: 6

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Ala Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125
```

```
Val Val Asp Phe Leu Arg Arg Trp Ile Ala Phe Cys Gln Ser Ile Ile
    130                 135                 140

Ser Thr Ser Pro Gln
145
```

```
<210> SEQ ID NO 7
<211> LENGTH: 447
<212> TYPE: DNA
<213> ORGANISM: Artificial Sequence
<220> FEATURE:
<223> OTHER INFORMATION: Synthetic construct: E76G (nucleic acid
      sequence)

<400> SEQUENCE: 7

gcacccactt caagctccac ttcaagctct acagcggaag cacagcagca gcagcagcag      60

cagcagcagc agcagcagca cctggagcag ctgttgatgg acctacagga gctcctgagc     120

aggatggaga attacaggaa cctgaaactc cccaggatgc tcaccttcaa attttacttg     180

cccaagcagg ccacagaatt gaaagatctt cagtgcctag aagatggtct tggacctctg     240

cggcatgttc tggatttgac tcaaagcaaa agctttcaat tggaagatgc tgagaatttc     300

atcagcaata tcagagtaac tgttgtaaaa ctaaagggct ctgacaacac atttgagtgc     360

caattcgatg atgagtcagc aactgtggtg gactttctga ggagatggat agccttctgt     420

caaagcatca tctcaacaag ccctcaa                                         447
```

```
<210> SEQ ID NO 8
<211> LENGTH: 149
<212> TYPE: PRT
<213> ORGANISM: Artificial Sequence
<220> FEATURE:
<223> OTHER INFORMATION: Synthetic construct: E76G (amino acid sequence)

<400> SEQUENCE: 8

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Gly Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

```
<210> SEQ ID NO 9
<211> LENGTH: 816
<212> TYPE: DNA
<213> ORGANISM: Artificial Sequence
```

<220> FEATURE:
<223> OTHER INFORMATION: Synthetic construct: D265A Fc/Flag (nucleic acid sequence)

<400> SEQUENCE: 9

```
atgagggtcc ccgctcagct cctggggctc ctgctgctct ggctcccagg tgcacgatgt     60

gagcccagag tgcccataac acagaacccc tgtcctccac tcaaagagtg tcccccatgc    120

gcagctccag acctcttggg tggaccatcc gtcttcatct tccctccaaa gatcaaggat    180

gtactcatga tctccctgag ccccatggtc acatgtgtgg tggtggccgt gagcgaggat    240

gacccagacg tccagatcag ctggtttgtg aacaacgtgg aagtacacac agctcagaca    300

caaacccata gagaggatta caacagtact ctccgggtgg tcagtgccct ccccatccag    360

caccaggact ggatgagtgg caaggagttc aaatgcaagg tcaacaacag agccctccca    420

tcccccatcg agaaaaccat ctcaaaaccc agagggccag taagagctcc acaggtatat    480

gtcttgcctc caccagcaga agagatgact aagaaagagt tcagtctgac ctgcatgatc    540

acaggcttct tacctgccga aattgctgtg gactggacca gcaatgggcg tacagagcaa    600

aactacaaga acaccgcaac agtcctggac tctgatggtt cttacttcat gtacagcaag    660

ctcagagtac aaaagagcac ttgggaaaga ggaagtcttt tcgcctgctc agtggtccac    720

gagggtctgc acaatcacct tacgactaag accatctccc ggtctctggg taaaggtggc    780

ggatctgact acaaggacga cgatgacaag tgataa                              816
```

<210> SEQ ID NO 10
<211> LENGTH: 270
<212> TYPE: PRT
<213> ORGANISM: Artificial Sequence
<220> FEATURE:
<223> OTHER INFORMATION: Synthetic construct: D265A Fc/Flag (amino acid sequence)

<400> SEQUENCE: 10

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
```

```
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Asp Tyr Lys Asp Asp Asp Asp Lys
            260                 265                 270
```

```
<210> SEQ ID NO 11
<211> LENGTH: 1257
<212> TYPE: DNA
<213> ORGANISM: Artificial Sequence
<220> FEATURE:
<223> OTHER INFORMATION: Synthetic construct: D265A Fc/wt mIL-2 (nucleic
      acid sequence)

<400> SEQUENCE: 11

atgagggtcc ccgctcagct cctggggctc ctgctgctct ggctcccagg tgcacgatgt      60

gagcccagag tgcccataac acagaacccc tgtcctccac tcaaagagtg tcccccatgc     120

gcagctccag acctcttggg tggaccatcc gtcttcatct tccctccaaa gatcaaggat     180

gtactcatga tctccctgag ccccatggtc acatgtgtgg tggtggccgt gagcgaggat     240

gacccagacg tccagatcag ctggtttgtg aacaacgtgg aagtacacac agctcagaca     300

caaacccata gagaggatta caacagtact ctccgggtgg tcagtgccct ccccatccag     360

caccaggact ggatgagtgg caaggagttc aaatgcaagg tcaacaacag agccctccca     420

tcccccatcg agaaaaccat ctcaaaaccc agagggccag taagagctcc acaggtatat     480

gtcttgcctc caccagcaga agagatgact aagaaagagt tcagtctgac ctgcatgatc     540

acaggcttct tacctgccga aattgctgtg gactggacca gcaatgggcg tacagagcaa     600

aactacaaga acaccgcaac agtcctggac tctgatggtt cttacttcat gtacagcaag     660

ctcagagtac aaaagagcac ttgggaaaga ggaagtcttt tcgcctgctc agtggtccac     720

gagggtctgc acaatcacct tacgactaag accatctccc ggtctctggg taaaggaggg     780

ggctccgcac ccacttcaag ctccacttca agctctacag cggaagcaca gcagcagcag     840

cagcagcagc agcagcagca gcagcacctg gagcagctgt tgatggacct acaggagctc     900

ctgagcagga tggagaatta caggaacctg aaactcccca ggatgctcac cttcaaattt     960

tacttgccca agcaggccac agaattgaaa gatcttcagt gcctagaaga tgaacttgga    1020

cctctgcggc atgttctgga tttgactcaa agcaaaagct ttcaattgga agatgctgag    1080

aatttcatca gcaatatcag agtaactgtt gtaaaactaa agggctctga caacacattt    1140

gagtgccaat tcgatgatga gtcagcaact gtggtggact ttctgaggag atggatagcc    1200

ttctgtcaaa gcatcatctc aacaagccct caacaccatc accaccatca ctgataa       1257
```

```
<210> SEQ ID NO 12
<211> LENGTH: 417
<212> TYPE: PRT
<213> ORGANISM: Artificial Sequence
<220> FEATURE:
<223> OTHER INFORMATION: Synthetic construct: D265A Fc/wt mIL-2 (amino
      acid sequence)
```

<400> SEQUENCE: 12

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Glu Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415
```

His

<210> SEQ ID NO 13
<211> LENGTH: 1257
<212> TYPE: DNA
<213> ORGANISM: Artificial Sequence
<220> FEATURE:
<223> OTHER INFORMATION: Synthetic construct: D265A Fc /QQ6210 (nucleic acid sequence)

<400> SEQUENCE: 13

```
atgagggtcc ccgctcagct cctggggctc ctgctgctct ggctcccagg tgcacgatgt      60

gagcccagag tgcccataac acagaacccc tgtcctccac tcaaagagtg tccccccatgc    120

gcagctccag acctcttggg tggaccatcc gtcttcatct tccctccaaa gatcaaggat    180

gtactcatga tctccctgag ccccatggtc acatgtgtgg tggtggccgt gagcgaggat    240

gacccagacg tccagatcag ctggtttgtg aacaacgtgg aagtacacac agctcagaca    300

caaacccata gagaggatta caacagtact ctccgggtgg tcagtgccct ccccatccag    360

caccaggact ggatgagtgg caaggagttc aaatgcaagg tcaacaacag agccctccca    420

tcccccatcg agaaaaccat ctcaaaaccc agagggccag taagagctcc acaggtatat    480

gtcttgcctc caccagcaga agagatgact aagaaagagt tcagtctgac ctgcatgatc    540

acaggcttct tacctgccga aattgctgtg gactggacca gcaatgggcg tacagagcaa    600

aactacaaga acaccgcaac agtcctggac tctgatggtt cttacttcat gtacagcaag    660

ctcagagtac aaaagagcac ttgggaaaga ggaagtcttt tcgcctgctc agtggtccac    720

gagggtctgc acaatcacct tacgactaag accatctccc ggtctctggg taaaggaggg    780

ggctccgcac ccacttcaag ctccacttca agctctacag cggaagcaca acagcagcag    840

cagcagcagc agcagcagca gcagcacctg gagcagctgt tgatggacct acaggaactc    900

ctgagtagga tggaggatca caggaacctg agactcccca ggatgctcac cttcaaattt    960

tacttgcccg agcaggccac agaattggaa gatcttcagt gcctagaaga tgaacttgaa   1020

ccactgcggc aagttctgga tttgactcaa agcaaaagct ttcaattgga agatgctgag   1080

aatttcatca gcaatatcag agtaactgtt gtaaaactaa agggctctga caacacattt   1140

gagtgccaat tcgacgatga gccagcaact gtggtggact ttctgaggag atggatagcc   1200

ttctgtcaaa gcatcatctc aacaagccct caacaccatc accaccatca ctgataa      1257
```

<210> SEQ ID NO 14
<211> LENGTH: 417
<212> TYPE: PRT
<213> ORGANISM: Artificial Sequence
<220> FEATURE:
<223> OTHER INFORMATION: Synthetic construct: D265A Fc /QQ6210 (amino acid sequence)

<400> SEQUENCE: 14

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60
```

```
Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asp His Arg Asn Leu Arg Leu Pro Arg Met Leu Thr Phe Lys Phe
305                 310                 315                 320

Tyr Leu Pro Glu Gln Ala Thr Glu Leu Glu Asp Leu Gln Cys Leu Glu
                325                 330                 335

Asp Glu Leu Glu Pro Leu Arg Gln Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Pro Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

```
<210> SEQ ID NO 15
<211> LENGTH: 1257
<212> TYPE: DNA
<213> ORGANISM: Artificial Sequence
<220> FEATURE:
<223> OTHER INFORMATION: Synthetic construct: D265A Fc / E76A (nucleic
      acid sequence)

<400> SEQUENCE: 15
```

```
atgagggtcc ccgctcagct cctggggctc ctgctgctct ggctcccagg tgcacgatgt     60

gagcccagag tgcccataac acagaacccc tgtcctccac tcaaagagtg tcccccatgc    120

gcagctccag acctcttggg tggaccatcc gtcttcatct tccctccaaa gatcaaggat    180

gtactcatga tctccctgag ccccatggtc acatgtgtgg tggtggccgt gagcgaggat    240

gacccagacg tccagatcag ctggtttgtg aacaacgtgg aagtacacac agctcagaca    300

caaacccata gagaggatta caacagtact ctccgggtgg tcagtgccct ccccatccag    360

caccaggact ggatgagtgg caaggagttc aaatgcaagg tcaacaacag agccctccca    420

tcccccatcg agaaaaccat ctcaaaaccc agagggccag taagagctcc acaggtatat    480

gtcttgcctc caccagcaga agagatgact aagaaagagt tcagtctgac ctgcatgatc    540

acaggcttct tacctgccga aattgctgtg gactggacca gcaatgggcg tacagagcaa    600

aactacaaga acaccgcaac agtcctggac tctgatggtt cttacttcat gtacagcaag    660

ctcagagtac aaaagagcac ttgggaaaga ggaagtcttt tcgcctgctc agtggtccac    720

gagggtctgc acaatcacct tacgactaag accatctccc ggtctctggg taaaggaggg    780

ggctccgcac ccacttcaag ctccacttca agctctacag cggaagcaca gcagcagcag    840

cagcagcagc agcagcagca gcagcacctg gagcagctgt tgatggacct acaggagctc    900

ctgagcagga tggagaatta caggaacctg aaactcccca ggatgctcac cttcaaattt    960

tacttgccca agcaggccac agaattgaaa gatcttcagt gcctagaaga tgctcttgga   1020

cctctgcggc atgttctgga tttgactcaa agcaaaagct ttcaattgga agatgctgag   1080

aatttcatca gcaatatcag agtaactgtt gtaaaactaa agggctctga caacacattt   1140

gagtgccaat tcgatgatga gtcagcaact gtggtggact ttctgaggag atggatagcc   1200

ttctgtcaaa gcatcatctc aacaagccct caacaccatc accaccatca ctgataa      1257
```

<210> SEQ ID NO 16
<211> LENGTH: 417
<212> TYPE: PRT
<213> ORGANISM: Artificial Sequence
<220> FEATURE:
<223> OTHER INFORMATION: Synthetic construct: D265A Fc / E76A (amino acid sequence)

<400> SEQUENCE: 16

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140
```

```
Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Ala Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

<210> SEQ ID NO 17
<211> LENGTH: 1257
<212> TYPE: DNA
<213> ORGANISM: Artificial Sequence
<220> FEATURE:
<223> OTHER INFORMATION: Synthetic construct: D265A Fc / E76G (nucleic acid sequence)

<400> SEQUENCE: 17

```
atgagggtcc ccgctcagct cctggggctc ctgctgctct ggctcccagg tgcacgatgt      60

gagcccagag tgcccataac acagaacccc tgtcctccac tcaaagagtg tccccccatgc    120

gcagctccag acctcttggg tggaccatcc gtcttcatct tccctccaaa gatcaaggat    180

gtactcatga tctccctgag ccccatggtc acatgtgtgg tggtggccgt gagcgaggat    240

gacccagacg tccagatcag ctggtttgtg aacaacgtgg aagtacacac agctcagaca    300

caaacccata gagaggatta caacagtact ctccgggtgg tcagtgccct ccccatccag    360

caccaggact ggatgagtgg caaggagttc aaatgcaagg tcaacaacag agccctccca    420
```

```
tcccccatcg agaaaaccat ctcaaaaccc agagggccag taagagctcc acaggtatat    480

gtcttgcctc caccagcaga agagatgact aagaaagagt tcagtctgac ctgcatgatc    540

acaggcttct tacctgccga aattgctgtg gactggacca gcaatgggcg tacagagcaa    600

aactacaaga acaccgcaac agtcctggac tctgatggtt cttacttcat gtacagcaag    660

ctcagagtac aaaagagcac ttgggaaaga ggaagtcttt tcgcctgctc agtggtccac    720

gagggtctgc acaatcacct tacgactaag accatctccc ggtctctggg taaaggaggg    780

ggctccgcac ccacttcaag ctccacttca agctctacag cggaagcaca gcagcagcag    840

cagcagcagc agcagcagca gcagcacctg gagcagctgt tgatggacct acaggagctc    900

ctgagcagga tggagaatta caggaacctg aaactcccca ggatgctcac cttcaaattt    960

tacttgccca agcaggccac agaattgaaa gatcttcagt gcctagaaga tggtcttgga   1020

cctctgcggc atgttctgga tttgactcaa agcaaaagct ttcaattgga agatgctgag   1080

aatttcatca gcaatatcag agtaactgtt gtaaaactaa agggctctga caacacattt   1140

gagtgccaat tcgatgatga gtcagcaact gtggtggact ttctgaggag atggatagcc   1200

ttctgtcaaa gcatcatctc aacaagccct caacaccatc accaccatca ctgataa      1257
```

<210> SEQ ID NO 18
<211> LENGTH: 417
<212> TYPE: PRT
<213> ORGANISM: Artificial Sequence
<220> FEATURE:
<223> OTHER INFORMATION: Synthetic construct: D265A Fc / E76G (amino acid sequence)

<400> SEQUENCE: 18

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
```

```
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Gly Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

<210> SEQ ID NO 19
<211> LENGTH: 447
<212> TYPE: DNA
<213> ORGANISM: Artificial Sequence
<220> FEATURE:
<223> OTHER INFORMATION: Synthetic construct: mIL-2 QQ 6.2-4 (nucleic acid sequence)

<400> SEQUENCE: 19

```
gcacccacct caagctccac ttcaagctct acagcggaag cacaacagca gcagcagcag     60

cagcagcagc agcagcagca cctggagcag ctgttgatgg acctacagga gctcctgagc    120

aggatggagg attccaggaa cctgagactc cccaggatgc tcaccttcaa attttacttg    180

cccaagcagg ccacagaatt ggaagatctt cagtgcctag aagatgaact tgaacctctg    240

cggcaagttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgatg atgagccagc aactgtggtg ggctttctga ggagatggat agccttctgt    420

caaagcatca tctcaacgag ccctcaa                                        447
```

<210> SEQ ID NO 20
<211> LENGTH: 149
<212> TYPE: PRT
<213> ORGANISM: Artificial Sequence
<220> FEATURE:
<223> OTHER INFORMATION: Synthetic construct: mIL-2 QQ 6.2-4 (amino acid sequence)

<400> SEQUENCE: 20

```
Ala Pro Thr Ser Ser Ser Thr Ser Ser Ser Thr Ala Glu Ala Gln Gln
```

-continued

```
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145
```

<210> SEQ ID NO 21
<211> LENGTH: 435
<212> TYPE: DNA
<213> ORGANISM: Artificial Sequence
<220> FEATURE:
<223> OTHER INFORMATION: Synthetic construct: mIL-2 QQ 6.2-8 (nucleic acid sequence)

<400> SEQUENCE: 21

```
gcacccacct caagctccac ttcaagctct acagcggaag cacaacagca gcagcagcag     60

cagcagcacc tggagcagct gttgatggac ctacaggagc tcctgagtag gatggaggat    120

cacaggaacc tgagactccc caggatgctc accttcaaat tttacttgcc caagcaggcc    180

acagaattgg aagatcttca gtgcctagaa gatgaacttg aacctctgcg gcaagttctg    240

gatttgactc aaagcaaaag ctttcaattg gaagatgctg agaatttcat cagcaatatc    300

agagtaactg ttgtaaaact aaagggctct gacaacacat ttgagtgcca attcgatgat    360

gagccagcaa ctgtggtgga ctttctgagg agatggatag ccttctgtca aagcatcatc    420

tcaacaagcc ctcga                                                     435
```

<210> SEQ ID NO 22
<211> LENGTH: 145
<212> TYPE: PRT
<213> ORGANISM: Artificial Sequence
<220> FEATURE:
<223> OTHER INFORMATION: Synthetic construct: mIL-2 QQ 6.2-8 (amino acid sequence)

<400> SEQUENCE: 22

```
Ala Pro Thr Ser Ser Ser Thr Ser Ser Ser Thr Ala Glu Ala Gln Gln
1               5                   10                  15

Gln Gln Gln Gln Gln Gln His Leu Glu Gln Leu Leu Met Asp Leu Gln
            20                  25                  30

Glu Leu Leu Ser Arg Met Glu Asp His Arg Asn Leu Arg Leu Pro Arg
        35                  40                  45

Met Leu Thr Phe Lys Phe Tyr Leu Pro Lys Gln Ala Thr Glu Leu Glu
    50                  55                  60
```

```
Asp Leu Gln Cys Leu Glu Asp Glu Leu Glu Pro Leu Arg Gln Val Leu
65                  70                  75                  80

Asp Leu Thr Gln Ser Lys Ser Phe Gln Leu Glu Asp Ala Glu Asn Phe
                85                  90                  95

Ile Ser Asn Ile Arg Val Thr Val Val Lys Leu Lys Gly Ser Asp Asn
            100                 105                 110

Thr Phe Glu Cys Gln Phe Asp Asp Glu Pro Ala Thr Val Val Asp Phe
        115                 120                 125

Leu Arg Arg Trp Ile Ala Phe Cys Gln Ser Ile Ile Ser Thr Ser Pro
    130                 135                 140

Arg
145
```

<210> SEQ ID NO 23
<211> LENGTH: 447
<212> TYPE: DNA
<213> ORGANISM: Artificial Sequence
<220> FEATURE:
<223> OTHER INFORMATION: Synthetic construct: mIL-2 QQ 6.2-10 (nucleic acid sequence)

<400> SEQUENCE: 23

```
gcacccacct caagctccac ttcaagctct acagcggaag cacaacagca gcagcagcag     60

cagcagcagc agcagcagca cctggagcag ctgttgatgg acctacagga actcctgagt    120

aggatggagg atcacaggaa cctgagactc cccaggatgc tcaccttcaa attttacttg    180

cccgagcagg ccacagaatt ggaagatctt cagtgcctag aagatgaact tgaaccactg    240

cggcaagttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgacg atgagccagc aactgtggtg gactttctga ggagatggat agccttctgt    420

caaagcatca tctcaacaag ccctcag                                        447
```

<210> SEQ ID NO 24
<211> LENGTH: 149
<212> TYPE: PRT
<213> ORGANISM: Artificial Sequence
<220> FEATURE:
<223> OTHER INFORMATION: Synthetic construct: mIL-2 QQ 6.2-10 (amino acid sequence)

<400> SEQUENCE: 24

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125
```

```
Val Val Asp Phe Leu Arg Arg Trp Ile Ala Phe Cys Gln Ser Ile Ile
    130                 135                 140

Ser Thr Ser Pro Gln
145


<210> SEQ ID NO 25
<211> LENGTH: 438
<212> TYPE: DNA
<213> ORGANISM: Artificial Sequence
<220> FEATURE:
<223> OTHER INFORMATION: Synthetic construct: mIL-2 QQ 6.2-11 (nucleic
      acid sequence)

<400> SEQUENCE: 25

gcacccacct caagctccac ttcaagctct acagcggaag cacaacagca gcagcagcag      60

cagcagcagc acctggagca gctgttgatg gacctacagg agctcctgag caggatggag     120

gattccagga acctgagact ccccagaatg ctcaccttca aattttactt gcccgagcag     180

gccacagaat tgaaagatct ccagtgccta gaagatgaac ttgaacctct gcggcaagtt     240

ctggatttga ctcaaagcaa aagctttcaa ttggaagatg ctgagaattt catcagcaat     300

atcagagtaa ctgttgtaaa actaaagggc tctgacaaca catttgagtg ccaattcgac     360

gatgagccag caactgtggt ggactttctg aggagatgga tagccttctg tcaaagcatc     420

atctcaacaa gccctcag                                                   438


<210> SEQ ID NO 26
<211> LENGTH: 146
<212> TYPE: PRT
<213> ORGANISM: Artificial Sequence
<220> FEATURE:
<223> OTHER INFORMATION: Synthetic construct: mIL-2 QQ 6.2-11 (amino
      acid sequence)

<400> SEQUENCE: 26

Ala Pro Thr Ser Ser Ser Thr Ser Ser Ser Thr Ala Glu Ala Gln Gln
1               5                   10                  15

Gln Gln Gln Gln Gln Gln Gln His Leu Glu Gln Leu Leu Met Asp Leu
            20                  25                  30

Gln Glu Leu Leu Ser Arg Met Glu Asp Ser Arg Asn Leu Arg Leu Pro
        35                  40                  45

Arg Met Leu Thr Phe Lys Phe Tyr Leu Pro Glu Gln Ala Thr Glu Leu
    50                  55                  60

Lys Asp Leu Gln Cys Leu Glu Asp Glu Leu Glu Pro Leu Arg Gln Val
65                  70                  75                  80

Leu Asp Leu Thr Gln Ser Lys Ser Phe Gln Leu Glu Asp Ala Glu Asn
                85                  90                  95

Phe Ile Ser Asn Ile Arg Val Thr Val Val Lys Leu Lys Gly Ser Asp
            100                 105                 110

Asn Thr Phe Glu Cys Gln Phe Asp Asp Glu Pro Ala Thr Val Val Asp
        115                 120                 125

Phe Leu Arg Arg Trp Ile Ala Phe Cys Gln Ser Ile Ile Ser Thr Ser
    130                 135                 140

Pro Gln
145


<210> SEQ ID NO 27
<211> LENGTH: 447
<212> TYPE: DNA
```

<213> ORGANISM: Artificial Sequence
<220> FEATURE:
<223> OTHER INFORMATION: Synthetic construct: mIL-2 QQ 6.2-13 (nucleic acid sequence)

<400> SEQUENCE: 27

```
gcacccacct caagctccac ttcaagctct acagcggaag cacaacagca gcagcagcag     60

cagcagcagc agcagcagca cctggagcag ctgttgatgg acctacagga gctcctgagt    120

aggatggagg atcacaggaa cctgagactc cccaggatgc tcaccttcaa attttacttg    180

cccgagcagg ccacagaatt gaaagatctc cagtgcctag aagatgaact tgaacctctg    240

cggcaggttc tggatttgac tcaaagcaaa agctttcaat tggaagatgc tgagaatttc    300

atcagcaata tcagagtaac tgttgtaaaa ctaaagggct ctgacaacac atttgagtgc    360

caattcgatg atgagccagc aactgtggtg gactttctga ggagatggat agccttctgt    420

caaagcatca tctcaacaag ccctcag                                        447
```

<210> SEQ ID NO 28
<211> LENGTH: 149
<212> TYPE: PRT
<213> ORGANISM: Artificial Sequence
<220> FEATURE:
<223> OTHER INFORMATION: Synthetic construct: mIL-2 QQ 6.2-13 (amino acid sequence)

<400> SEQUENCE: 28

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 29
<211> LENGTH: 461
<212> TYPE: DNA
<213> ORGANISM: Homo sapiens
<220> FEATURE:
<221> NAME/KEY: misc_feature
<223> OTHER INFORMATION: Full length human IL-2 (nucleic acid sequence)

<400> SEQUENCE: 29

```
atgtacagga tgcaactcct gtcttgcatt gcactaagtc ttgcacttgt cacaaacagt     60

gcacctactt caagttctac aaagaaaaca cagctacaac tggagcattt actgctggat    120
```

```
ttacagatga ttttgaatgg aattaataat tacaagaatc ccaaactcac caggatgctc    180

acatttaagt tttacatgcc caagaaggcc acagaactga aacatcttca gtgtctagaa    240

gaagaactca aacctctgga ggaagtgcta aatttagctc aaagcaaaaa ctttcactta    300

agacccaggg acttaatcag caatatcaac gtaatagttc tggaactaaa gggatctgaa    360

acaacattca tgtgtaatat gctgatgaga cagcaaccat tgtagaattt ctgaacagat    420

ggattacctt ttgtcaaagc atcatctcaa cactgacttg a                        461
```

<210> SEQ ID NO 30
<211> LENGTH: 153
<212> TYPE: PRT
<213> ORGANISM: Homo sapiens
<220> FEATURE:
<221> NAME/KEY: misc_feature
<223> OTHER INFORMATION: Full length human IL-2 (amino acid sequence)

<400> SEQUENCE: 30

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 31
<211> LENGTH: 401
<212> TYPE: DNA
<213> ORGANISM: Homo sapiens
<220> FEATURE:
<221> NAME/KEY: misc_feature
<223> OTHER INFORMATION: Human IL-2 without signal peptide (nucleic acid sequence)

<400> SEQUENCE: 31

```
gcacctactt caagttctac aaagaaaaca cagctacaac tggagcattt actgctggat     60

ttacagatga ttttgaatgg aattaataat tacaagaatc ccaaactcac caggatgctc    120

acatttaagt tttacatgcc caagaaggcc acagaactga aacatcttca gtgtctagaa    180

gaagaactca aacctctgga ggaagtgcta aatttagctc aaagcaaaaa ctttcactta    240

agacccaggg acttaatcag caatatcaac gtaatagttc tggaactaaa gggatctgaa    300

acaacattca tgtgtaatat gctgatgaga cagcaaccat tgtagaattt ctgaacagat    360

ggattacctt ttgtcaaagc atcatctcaa cactgacttg a                        401
```

<210> SEQ ID NO 32
<211> LENGTH: 133
<212> TYPE: PRT
<213> ORGANISM: Homo sapiens
<220> FEATURE:
<221> NAME/KEY: misc_feature
<223> OTHER INFORMATION: Human IL-2 without signal peptide (amino acid sequence)

<400> SEQUENCE: 32

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 33
<211> LENGTH: 330
<212> TYPE: PRT
<213> ORGANISM: Homo sapiens
<220> FEATURE:
<221> NAME/KEY: misc_feature
<223> OTHER INFORMATION: Human IgG1 constant region (amino acid sequence)

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 34
<211> LENGTH: 232
<212> TYPE: PRT
<213> ORGANISM: Homo sapiens
<220> FEATURE:
<221> NAME/KEY: misc_feature
<223> OTHER INFORMATION: Human IgG1 Fc domain (amino acid sequence)

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 35
<211> LENGTH: 149
<212> TYPE: PRT
<213> ORGANISM: Artificial Sequence
<220> FEATURE:
<223> OTHER INFORMATION: Synthetic construct 6.2-6

<400> SEQUENCE: 35

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asp Phe Ile Ser Asn Ile Arg Val Thr Val Ala Lys Leu Arg
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 36
<211> LENGTH: 148
<212> TYPE: PRT
<213> ORGANISM: Artificial Sequence
<220> FEATURE:
<223> OTHER INFORMATION: Synthetic construct 6.2-9

<400> SEQUENCE: 36

Ala Pro Thr Ser Ser Ser Thr Ser Ser Ser Thr Ala Glu Ala Gln Gln
1               5                   10                  15

Gln Gln Gln Gln Gln Gln Gln Gln Arg His Leu Glu Gln Leu Ser Met
            20                  25                  30

Asp Leu Gln Glu Leu Leu Ser Arg Met Glu Asp Ser Arg Asn Leu Arg
        35                  40                  45

Leu Pro Arg Met Leu Thr Phe Lys Phe Tyr Leu Pro Glu Gln Ala Thr
    50                  55                  60

Glu Leu Lys Asp Leu Gln Cys Leu Glu Asp Glu Leu Glu Pro Leu Arg
65                  70                  75                  80

Gln Val Leu Asp Leu Thr Gln Ser Lys Ser Phe Gln Leu Glu Asp Ala
                85                  90                  95
```

```
Glu Asp Phe Ile Ser Asn Ile Arg Val Thr Val Ala Lys Leu Lys Gly
            100                 105                 110

Ser Asp Asn Thr Phe Glu Cys Gln Phe Asp Asp Glu Pro Ala Thr Val
        115                 120                 125

Val Asp Phe Leu Arg Arg Trp Ile Ala Phe Cys Gln Ser Ile Ile Ser
    130                 135                 140

Thr Ser Pro Gln
145


<210> SEQ ID NO 37
<211> LENGTH: 149
<212> TYPE: PRT
<213> ORGANISM: Artificial Sequence
<220> FEATURE:
<223> OTHER INFORMATION: Synthetic construct 6.2-11

<400> SEQUENCE: 37

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asp Phe Ile Ser Asn Ile Arg Val Thr Val Ala Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 38
<211> LENGTH: 149
<212> TYPE: PRT
<213> ORGANISM: Artificial Sequence
<220> FEATURE:
<223> OTHER INFORMATION: Synthetic construct 6.2-12

<400> SEQUENCE: 38

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Val Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
```

```
                85                  90                  95

Ala Glu Asn Phe Ile Ser Asn Ile Arg Val Thr Val Ala Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 39
<211> LENGTH: 144
<212> TYPE: PRT
<213> ORGANISM: Artificial Sequence
<220> FEATURE:
<223> OTHER INFORMATION: Synthetic construct 6.2-2

<400> SEQUENCE: 39

Ala Pro Thr Ser Ser Ser Thr Ser Ser Ser Thr Ala Glu Ala Gln Gln
1               5                   10                  15

Gln Gln Gln Gln Gln His Leu Glu Gln Leu Ser Met Asp Leu Gln Glu
            20                  25                  30

Leu Leu Ser Arg Met Glu Asp His Arg Asn Leu Arg Leu Pro Arg Met
        35                  40                  45

Leu Thr Phe Lys Phe Tyr Leu Pro Glu Gln Ala Thr Glu Leu Lys Asp
    50                  55                  60

Leu Gln Cys Leu Glu Asp Glu Leu Glu Pro Leu Arg Gln Val Leu Asp
65                  70                  75                  80

Leu Thr Gln Ser Lys Ser Phe Gln Leu Glu Gly Ala Glu Asn Phe Ile
                85                  90                  95

Ser Asn Ile Arg Ala Thr Val Val Lys Leu Lys Gly Ser Asp Asn Thr
            100                 105                 110

Phe Glu Cys Gln Phe Asp Asp Glu Pro Ala Thr Val Val Asp Phe Leu
        115                 120                 125

Arg Arg Trp Ile Ala Phe Cys Gln Ser Ile Ile Ser Thr Ser Pro Gln
    130                 135                 140


<210> SEQ ID NO 40
<211> LENGTH: 149
<212> TYPE: PRT
<213> ORGANISM: Artificial Sequence
<220> FEATURE:
<223> OTHER INFORMATION: Synthetic construct 6.2-13

<400> SEQUENCE: 40

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
                85                  90                  95
```

```
Ala Glu Asn Phe Ile Ser Asn Ile Arg Ala Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 41
<211> LENGTH: 149
<212> TYPE: PRT
<213> ORGANISM: Artificial Sequence
<220> FEATURE:
<223> OTHER INFORMATION: Synthetic construct 6.2-7

<400> SEQUENCE: 41

Ala Pro Thr Ser Ser Ser Thr Ser Ser Ser Thr Ala Glu Ala Gln Gln
1               5                   10                  15

Gln Gln Gln Gln Gln Gln Gln Gln Arg Arg His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
                85                  90                  95

Ala Glu Asn Phe Ile Ser Asn Ile Arg Ala Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 42
<211> LENGTH: 149
<212> TYPE: PRT
<213> ORGANISM: Artificial Sequence
<220> FEATURE:
<223> OTHER INFORMATION: Synthetic construct 6.2-1

<400> SEQUENCE: 42

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
                85                  90                  95
```

```
Ala Glu Asn Phe Ile Ser Asn Ile Arg Val Thr Val Ala Lys Leu Lys
            100                 105                 110

Gly Ser Asp Ser Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145


<210> SEQ ID NO 43
<211> LENGTH: 149
<212> TYPE: PRT
<213> ORGANISM: Artificial Sequence
<220> FEATURE:
<223> OTHER INFORMATION: Synthetic construct 6.2-10

<400> SEQUENCE: 43

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asp Phe Ile Ser Asn Ile Arg Val Thr Val Ala Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 44
<211> LENGTH: 148
<212> TYPE: PRT
<213> ORGANISM: Artificial Sequence
<220> FEATURE:
<223> OTHER INFORMATION: Synthetic construct 6.2-8

<400> SEQUENCE: 44

Ala Pro Thr Ser Ser Ser Thr Ser Ser Ser Thr Ala Glu Ala Gln Gln
1               5                   10                  15

Gln Gln Gln Gln Gln Gln Gln Gln Arg His Leu Glu Gln Leu Leu Met
            20                  25                  30

Asp Leu Gln Glu Leu Leu Ser Arg Met Glu Asp His Arg Asn Leu Arg
        35                  40                  45

Leu Pro Arg Met Leu Thr Phe Lys Phe Tyr Leu Pro Lys Gln Ala Thr
    50                  55                  60

Glu Leu Glu Asp Leu Gln Cys Leu Glu Asp Glu Leu Glu Pro Leu Arg
65                  70                  75                  80

Gln Val Leu Asp Leu Thr Gln Ser Lys Ser Phe Gln Leu Glu Gly Ala
```

```
                85                  90                  95

Glu Asn Phe Ile Ser Asn Ile Arg Ala Thr Val Val Lys Leu Lys Gly
            100                 105                 110

Ser Asp Asn Thr Phe Glu Cys Gln Phe Asp Asp Glu Pro Ala Thr Val
        115                 120                 125

Val Asp Phe Leu Arg Arg Trp Ile Ala Phe Cys Gln Ser Ile Ile Ser
    130                 135                 140

Thr Ser Pro Arg
145


<210> SEQ ID NO 45
<211> LENGTH: 148
<212> TYPE: PRT
<213> ORGANISM: Artificial Sequence
<220> FEATURE:
<223> OTHER INFORMATION: Synthetic construct 6.2-15

<400> SEQUENCE: 45

Ala Pro Thr Ser Ser Ser Thr Ser Ser Ser Thr Ala Glu Ala Gln Gln
1               5                   10                  15

Gln Gln Gln Gln Gln Gln Gln Gln Arg His Leu Glu Gln Leu Leu Met
            20                  25                  30

Asp Leu Gln Glu Leu Leu Ser Arg Met Glu Asp His Arg Asn Leu Arg
        35                  40                  45

Leu Pro Arg Met Leu Thr Phe Lys Phe Tyr Leu Pro Lys Gln Ala Thr
    50                  55                  60

Glu Leu Glu Asp Leu Gln Cys Leu Glu Asp Glu Leu Glu Pro Leu Arg
65                  70                  75                  80

Gln Val Leu Asp Leu Thr Gln Ser Lys Ser Phe Gln Leu Glu Gly Ala
                85                  90                  95

Glu Asn Phe Ile Ser Asn Ile Arg Val Thr Val Ala Lys Leu Lys Gly
            100                 105                 110

Ser Asp Ser Thr Phe Glu Cys Gln Phe Asp Asp Glu Pro Ala Thr Val
        115                 120                 125

Val Gly Phe Leu Arg Arg Trp Ile Ala Phe Cys Gln Ser Ile Ile Ser
    130                 135                 140

Thr Ser Pro Gln
145


<210> SEQ ID NO 46
<211> LENGTH: 149
<212> TYPE: PRT
<213> ORGANISM: Artificial Sequence
<220> FEATURE:
<223> OTHER INFORMATION: Synthetic construct 6.2-16

<400> SEQUENCE: 46

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80
```

```
Arg Gln Val Leu Asp Leu Thr Gln Ser Lys Ser Phe Gln Leu Glu Gly
                85                  90                  95

Ala Glu Asn Phe Ile Ser Asn Ile Arg Ala Thr Val Val Lys Leu Lys
            100                 105                 110

Gly Ser Asp Ser Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145


<210> SEQ ID NO 47
<211> LENGTH: 149
<212> TYPE: PRT
<213> ORGANISM: Artificial Sequence
<220> FEATURE:
<223> OTHER INFORMATION: Synthetic construct 6.2-3

<400> SEQUENCE: 47

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
                85                  90                  95

Ala Glu Asn Phe Ile Ser Asn Ile Arg Ala Thr Val Val Lys Leu Lys
            100                 105                 110

Gly Ser Asp Ser Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145


<210> SEQ ID NO 48
<211> LENGTH: 145
<212> TYPE: PRT
<213> ORGANISM: Artificial Sequence
<220> FEATURE:
<223> OTHER INFORMATION: Synthetic construct 6.2-5

<400> SEQUENCE: 48

Ala Pro Thr Ser Ser Ser Thr Ser Ser Ser Thr Ala Glu Ala Gln Gln
1               5                   10                  15

Gln Gln Gln Gln Gln Arg His Leu Glu Gln Leu Ser Met Asp Leu Gln
            20                  25                  30

Glu Leu Leu Ser Arg Met Glu Asp Ser Arg Asn Leu Arg Leu Pro Arg
        35                  40                  45

Met Leu Thr Phe Lys Phe Tyr Leu Pro Lys Gln Ala Thr Glu Leu Glu
    50                  55                  60

Asp Leu Gln Cys Leu Glu Asp Glu Leu Glu Pro Leu Arg Gln Val Leu
65                  70                  75                  80
```

```
Asp Leu Thr Gln Ser Lys Ser Phe Gln Leu Glu Gly Ala Glu Asn Phe
                85                  90                  95

Ile Ser Asp Ile Arg Val Ala Val Ala Lys Leu Lys Gly Ser Asp Asn
            100                 105                 110

Thr Phe Glu Cys Gln Phe Asp Asp Glu Pro Ala Thr Val Val Asp Phe
        115                 120                 125

Leu Arg Arg Trp Ile Ala Phe Cys Gln Ser Ile Ile Ser Thr Ser Pro
    130                 135                 140

Gln
145


<210> SEQ ID NO 49
<211> LENGTH: 149
<212> TYPE: PRT
<213> ORGANISM: Artificial Sequence
<220> FEATURE:
<223> OTHER INFORMATION: Synthetic construct 6.2-14

<400> SEQUENCE: 49

Ala Pro Thr Ser Ser Ser Thr Ser Ser Ser Thr Ala Glu Ala Gln Gln
1               5                   10                  15

Gln Gln Gln Gln Gln Gln Gln Gln Gln Arg His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Gly
                85                  90                  95

Ala Glu Asn Phe Ile Ser Asp Ile Arg Val Ala Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145


<210> SEQ ID NO 50
<211> LENGTH: 149
<212> TYPE: PRT
<213> ORGANISM: Artificial Sequence
<220> FEATURE:
<223> OTHER INFORMATION: Synthetic construct 6.2-4

<400> SEQUENCE: 50

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Ser
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
```

-continued

```
65                  70                  75                  80

Arg Gln Val Leu Asp Leu Thr Gln Ser Lys Ser Phe Gln Leu Glu Asp
                85                  90                  95

Ala Glu Asp Phe Ile Ser Asn Ile Arg Val Thr Val Ala Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145
```